(12) United States Patent
Duran et al.

(10) Patent No.: US 8,242,177 B2
(45) Date of Patent: Aug. 14, 2012

(54) DERIVATIVES OF 4-(2-AMINO-1-HYDROXYETHYL)PHENOL AS AGONISTS OF THE β2 ADRENERGIC RECEPTOR

(75) Inventors: Carlos Puig Duran, Barcelona (ES); Maria Isabel Crespo Crespo, Barcelona (ES); Julio Cesar Castro Palomino Laria, Premia de Mar (ES); Silvia Gual Roig, Cabrera de Mar (ES); Eloisa Navarro Romero, Barcelona (ES)

(73) Assignee: Almirall, S.A., Barcelona (ES)

( * ) Notice: Subject to any disclaimer, the term of this patent is extended or adjusted under 35 U.S.C. 154(b) by 0 days.

(21) Appl. No.: 13/094,156

(22) Filed: Apr. 26, 2011

(65) Prior Publication Data

US 2011/0251165 A1 Oct. 13, 2011
US 2012/0101075 A2 Apr. 26, 2012

Related U.S. Application Data

(62) Division of application No. 11/920,561, filed as application No. PCT/EP2006/004680 on May 17, 2006, now Pat. No. 7,964,615.

(30) Foreign Application Priority Data

May 20, 2005 (ES) ................... 200501229

(51) Int. Cl.
*A61K 31/135* (2006.01)
*C07C 213/00* (2006.01)
(52) U.S. Cl. ...................... 514/652; 564/346
(58) Field of Classification Search .......... 564/346; 514/312, 652
See application file for complete search history.

(56) References Cited

U.S. PATENT DOCUMENTS

| | | | |
|---|---|---|---|
| 3,007,923 A | 11/1961 | Muller et al. |
| 3,053,865 A | 9/1962 | Metuchen et al. |
| 3,104,246 A | 9/1963 | Amiard et al. |
| 3,678,137 A | 7/1972 | Pfeiffer et al. |
| 3,929,768 A | 12/1975 | Brattsand et al. |

(Continued)

FOREIGN PATENT DOCUMENTS

DE 2 236 272 2/1973

(Continued)

OTHER PUBLICATIONS

Han, J. "Advances in Characterization of Pharmaceutical Hydrates," Trends in Bio/Pharmaceutical Industry, 3:25-29 (2006).

(Continued)

*Primary Examiner* — Taylor Victor Oh
(74) *Attorney, Agent, or Firm* — Finnegan, Henderson, Farabow, Garrett & Dunner, LLP

(57) ABSTRACT

The present disclosure relates to 4-(2-amino-1-hydroxyethyl) phenol derivatives of formula (I) as well as pharmaceutical compositions comprising them, and their use in therapy as agonists of the BETA2 adrenergic receptor.

19 Claims, 1 Drawing Sheet

U.S. PATENT DOCUMENTS

| | | | |
|---|---|---|---|
| 3,970,677 | A | 7/1976 | Nishimura et al. |
| 3,975,391 | A | 8/1976 | Nakagawa et al. |
| 3,994,901 | A | 11/1976 | Nakagawa et al. |
| 4,022,776 | A | 5/1977 | Nakagawa et al. |
| 4,022,784 | A | 5/1977 | Nakagawa et al. |
| 4,026,897 | A | 5/1977 | Nakagawa et al. |
| 4,068,076 | A | 1/1978 | Nakagawa et al. |
| 4,145,542 | A | 3/1979 | Nakagawa et al. |
| 4,753,962 | A | 6/1988 | Ainsworth et al. |
| 4,992,474 | A | 2/1991 | Skidmore et al. |
| 4,997,986 | A | 3/1991 | Mitchell et al. |
| 5,099,068 | A | 3/1992 | Mitchell et al. |
| 5,109,023 | A | 4/1992 | Mitchell et al. |
| 5,201,308 | A | 4/1993 | Newhouse |
| 5,263,475 | A | 11/1993 | Altermatt et al. |
| 5,283,262 | A | 2/1994 | Mitchell et al. |
| 5,435,301 | A | 7/1995 | Herold et al. |
| 5,482,934 | A | 1/1996 | Calatayud et al. |
| 5,507,281 | A | 4/1996 | Kuhnel et al. |
| 5,617,845 | A | 4/1997 | Poss et al. |
| 5,685,294 | A | 11/1997 | Gupte et al. |
| 6,541,669 | B1 | 4/2003 | Moran et al. |
| 7,498,321 | B2 | 3/2009 | Biggadike et al. |
| 7,964,615 | B2 | 6/2011 | Puig Duran et al. |
| 2002/0055651 | A1 | 5/2002 | Moran et al. |
| 2003/0136405 | A1 | 7/2003 | Goede et al. |
| 2003/0153597 | A1 | 8/2003 | Moran et al. |
| 2004/0059116 | A1 | 3/2004 | Moran et al. |
| 2004/0167167 | A1 | 8/2004 | Mammen et al. |
| 2005/0043337 | A1 | 2/2005 | Rito et al. |
| 2005/0159448 | A1 | 7/2005 | McKinnell et al. |
| 2005/0192316 | A1 | 9/2005 | Moran et al. |
| 2005/0215590 | A1 | 9/2005 | Brown et al. |
| 2005/0272769 | A1 | 12/2005 | Linsell |
| 2006/0019991 | A1 | 1/2006 | McKinnell et al. |
| 2006/0035931 | A1 | 2/2006 | Chao et al. |
| 2006/0081246 | A1 | 4/2006 | Goede et al. |
| 2006/0178410 | A1 | 8/2006 | Moran et al. |
| 2006/0205949 | A1 | 9/2006 | Dalziel et al. |
| 2007/0197536 | A1 | 8/2007 | Dal Piaz et al. |
| 2009/0042933 | A1 | 2/2009 | Puig Duran et al. |
| 2009/0082378 | A1 | 3/2009 | Puig Duran et al. |
| 2010/0093681 | A1 | 4/2010 | Puig Duran et al. |
| 2010/0168161 | A1 | 7/2010 | Tanã et al. |
| 2010/0324000 | A1 | 12/2010 | Giulio Matassa et al. |
| 2011/0028442 | A1 | 2/2011 | Puig Duran et al. |
| 2011/0251166 | A1 | 10/2011 | Puig Duran et al. |
| 2011/0251234 | A1 | 10/2011 | Carrera Carrera et al. |

FOREIGN PATENT DOCUMENTS

| | | |
|---|---|---|
| DE | 2 310 140 | 9/1974 |
| DE | 2 461 861 | 8/1975 |
| DE | 4 239 402 | 5/1994 |
| EP | 0 069 715 | 1/1983 |
| EP | 0 147 719 | 7/1985 |
| EP | 0 166 294 | 1/1986 |
| EP | 0 286 242 | 10/1988 |
| EP | 0 317 206 | 5/1989 |
| EP | 0 424 790 | 5/1991 |
| EP | 0 505 321 | 9/1992 |
| EP | 0 674 533 | 10/1995 |
| EP | 1 078 629 | 2/2001 |
| EP | 1 235 787 | 9/2002 |
| EP | 1 577 291 | 9/2005 |
| ES | 2 232 306 | 5/2005 |
| GB | 0 869 511 | 5/1961 |
| GB | 1 200 886 | 8/1970 |
| GB | 1 247 370 | 9/1971 |
| GB | 1 458 251 | 12/1976 |
| GB | 1 468 156 | 3/1977 |
| GB | 2 041 763 | 9/1980 |
| GB | 2 140 800 | 12/1984 |
| GB | 2 165 159 | 12/1984 |
| GB | 2 160 863 | 1/1986 |
| GB | 2 242 134 | 9/1991 |
| JP | 51 149 282 | 12/1976 |
| JP | 59 093 051 | 5/1984 |
| WO | WO 91/02558 | 3/1991 |
| WO | WO 91/14468 | 10/1991 |
| WO | WO 92/00771 | 1/1992 |
| WO | WO 92/03175 | 3/1992 |
| WO | WO 92/04068 | 3/1992 |
| WO | WO 92/04928 | 4/1992 |
| WO | WO 92/09322 | 6/1992 |
| WO | WO 96/32150 | 10/1996 |
| WO | WO 97/00703 | 1/1997 |
| WO | WO 97/12687 | 4/1997 |
| WO | WO 98/09632 | 3/1998 |
| WO | WO 99/30703 | 6/1999 |
| WO | WO 99/64035 | 12/1999 |
| WO | WO 01/36375 | 5/2001 |
| WO | WO 01/42193 | 6/2001 |
| WO | WO 02/066422 | 8/2002 |
| WO | WO 02/070490 | 9/2002 |
| WO | WO 02/092606 | 11/2002 |
| WO | WO 03/000325 | 1/2003 |
| WO | WO 03/042160 | 5/2003 |
| WO | WO 03/061742 | 7/2003 |
| WO | WO 03/072539 | 9/2003 |
| WO | WO 03/091204 | 11/2003 |
| WO | WO 03/097613 | 11/2003 |
| WO | WO 03/099764 | 12/2003 |
| WO | WO 2004/011416 | 2/2004 |
| WO | WO 2004/016578 | 2/2004 |
| WO | WO 2004/058729 | 7/2004 |
| WO | WO 2004/089892 | 10/2004 |
| WO | WO 2004/106279 | 12/2004 |
| WO | WO 2005/030678 | 4/2005 |
| WO | WO 2005/049581 | 6/2005 |
| WO | WO 2005/121065 | 12/2005 |
| WO | WO 2005/123692 | 12/2005 |
| WO | WO 2005/123693 | 12/2005 |
| WO | WO 2006/023457 | 3/2006 |
| WO | WO 2006/051375 | 5/2006 |
| WO | WO 2006/122788 | 11/2006 |
| WO | WO 2007/124898 | 11/2007 |
| WO | WO 2008/046598 | 4/2008 |
| WO | WO 2008/095720 | 8/2008 |
| WO | WO 2009/068177 | 6/2009 |
| WO | WO 2009/106351 | 9/2009 |
| WO | WO 2010/072354 | 7/2010 |
| WO | WO 2010/094483 | 8/2010 |
| WO | WO 2010/094484 | 8/2010 |
| WO | WO 2010/102831 | 9/2010 |

OTHER PUBLICATIONS

International Search Report mailed Mar. 2, 2010, for International Application No. PCT/EP2009/008970 (WO 2010/072354).

International Search Report mailed May 25, 2010, for International Application No. PCT/EP2010/001027 (WO 2010/094484).

International Search Report mailed May 27, 2010, for International Application No. PCT/EP2010/001026 (WO 2010/094483).

Johnson, M. "Salmeterol," Medicinal Research Reviews, 15(3): 225-257 (1995).

Kikkawa, H. et al. "Differential contribution of two serine residues of wild type and constitutively active $\beta_2$-adrenoreceptors to the interaction with $\beta_2$-selective agonists," British Journal of Pharmacology, 121: 1059-1064 (1997).

Morissette, SL et al. "High-Throughput Crystallization: Polymorphs, Salts, Co-Crystals and Solvates of Pharmaceutical Solids," Advanced Drug Delivery Reviews, 56: 275-300 (2004).

U.S. Appl. No. 13/141,156, filed Jun. 21, 2011, Carrera Carrera et al.

U.S. Appl. No. 13/202,020, filed Aug. 17, 2011, Ruf et al.

U.S. Appl. No. 13/202,025, filed Aug. 17, 2011, Ruf et al.

Office Action dated Apr. 25, 2011 in U.S. Appl. No. 12/298,131.

Office Action dated Jul. 15, 2011 in U.S. Appl. No. 12/745,195.

Office Action dated Jul. 7, 2011 in U.S. Appl. No. 12/444,935.

Office Action dated Oct. 14, 2011 in U.S. Appl. No. 12/526,090.

Patani, GA et al. "Bioisosterism: A Rational Approach in Drug Design," Chem. Rev. 96: 314-3176 (1996).

Restriction Requirement dated May 13, 2011 in U.S. Appl. No. 12/444,935.

Restriction Requirement dated Jul. 20, 2011 in U.S. Appl. No. 12/526,090.
STN Search Report, Accession No. 2003:875242, CAS RN 620599-83-9 (2011).
Williams, DA et al. Foye's Principles of Medicinal Chemistry, 5th Edition, pp. 59-63 (2002).
Dexamethasone, Merck Index, Monograph No. 02943 (2011).
International Search Report mailed Sep. 16, 2010, for International Application No. PCT/EP2010/001582 (WO 2010/102832).
Notice of Allowance dated Dec. 28, 2011 in U.S. Appl. No. 12/745,195.
U.S. Appl. No. 13/255,621, filed Sep. 9, 2011, Marchueta Hereu et al.
U.S. Appl. No. 11/920,561, filed Feb. 11, 2008, Puig Duran et al.
U.S. Appl. No. 12/298,131, filed Oct. 22, 2008, Puig Duran et al.
U.S. Appl. No. 12/444,935, filed Apr. 9, 2009, Bach Tana et al.
U.S. Appl. No. 12/526,090, filed Aug. 6, 2009, Puig Duran et al.
U.S. Appl. No. 12/745,195, filed May 27, 2010, Giulio Matassa et al.
U.S. Appl. No. 12/919,134, filed Aug. 24, 2010, Puig Duran et al.
Bastin, RD et al. "Salt Selection and Optimisation for Pharmaceutical New Chemical Entities," Organic Process Research and Development, 4(5): 427-435 (2000).
CAPLUS English Abstract of DE 2 236 272, Accession No. 1973:405128.
CAPLUS English Abstract of DE 2 310 140, Accession No. 1975:31115.
CAPLUS English Abstract of JP 51 149 282, Accession No. 1977:468184.
CAPLUS English Abstract of JP 59 093 051, Accession No. 1985:45790.
CAPLUS English Abstract of journal article by Meglio, P. et al. Accession No. 1980:426036.
Coleman, R.A. et al. "Novel and Versatile Superfusion System," Journal of Pharmacological Methods, 21: 71-86 (1989).
Cortijo, J. et al. "Effects of dantrolene on the responses to methylxanthines in the isolated guinea-pig trachea," European Journal of Pharmacology 198: 171-176 (1991).
Curran, P.K. et al. "Endogenous β3-But Not β1-Adrenergic Receptors Are Resistant to Agonist-Mediated Regulation in Human SK-N-MC Neurotumor Cells," Cell. Signal., 8(5): 355-364 (1996).
Deyrup, M.D. et al. "Structure-affinity profile of 8-hydroxycarbostyril-based agonists that dissociate slowly from the β2-adrenoceptor," Naunyn-Schmiedeberg's Archives of Pharmacology, 359: 168-177(1999).
English Abstract of WO 2002/92606, dated Nov. 21, 2002.
Furuie, H. et al., "Suppressive effect of novel phosphodiesterase4 (PDE4) inhibitor ONO-6126 on TNF-α release was increased after repeated oral administration in healthy Japanese subjects," Eur. Resp. Journal, 22(Supp. 45):Abstract 2557 (2003).
Ismail, FMD. "Important fluorinated drugs in experimental and clinical use," Journal of Fluorine Chemistry 118:27-33 (2002).
Hart, D.J. "A Synthesis of (±)-Gephyrotoxin," Journal of Organic Chemistry, 46:3576-3578 (1981).
Hart, D.J. et al. "Total Synthesis of dl-Gephyrotoxin and dl-Dihydrogephyrotoxin," J. American Chem. Society, 105(5): 1255-1263 (1983).
Hashima, H. et al. "Synthesis and Biological Activities of the Marine Byrozoan Alkaloids Convolutamines A, C and F, and Lutamides A and C," Bioorganic & Medicinal Chemistry, 8: 1757-1766 (2000).
Hett, R. et al. "Enantioselective Synthesis of Salmeterol via Asymmetric Borane Reduction," Tetrahedron Letters, 35(50): 9375-9378 (1994).
Hett, R. et al. "Large-Scale Synthesis of Enantio- and Diastereomerically Pure (R,R)-Formoterol," Organic Process Research & Development, 2(2): 96-99 (1998).
International Search Report mailed Sep. 12, 2006, for International Application No. PCT/EP2006/004680 (WO 2006/122788 A1).
International Search Report mailed Jun. 21, 2007, for International Application No. PCT/EP2007/003601 (WO 2007/124898 A1).
International Search Report mailed Mar. 19, 2008, for International Application No. PCT/EP2007/008992 (WO 2008/046598 A1).
International Search Report mailed May 28, 2008, for International Application No. PCT/EP2008/000975 (WO 2008/095720).
International Search Report mailed May 7, 2009, for International Application No. PCT/EP2008/009469 (WO 2009/068177).
International Search Report mailed Apr. 21, 2009, for International Application No. PCT/EP2009/001431 (WO 2009/106351).
Interview Summary dated Jun. 11, 2010 for U.S. Appl. No. 11/920,561.
Kaiser, C. et al. "Adrenergic Agents. 1. Synthesis and Potential β-Adrenergic Agonist Activity of Some Catecholamine Analogs Bearing a Substituted Amino Functionality in the Meta Position," Journal of Medicinal Chemistry, 17(1): 49-57 (1974).
Meglio, P. et al. "Synthesis and pharmacological study of orciprenaline and salbutamol derivatives," Farmaco, Edizione Scientifica, 35(3): 203-230 (1980).
Meyers, A.I. et al. "Oxazolines. XI. Synthesis of Functionalized Aromatic and Aliphatic Acids. A Useful Protecting Group for Carboxylic Acids against Grignard and Hydride Reagents," Journal of Organic Chemistry, 39(18): 2787-2793 (1974).
Meyers, A.I. et al. "Substitutions on I-Methoxynaphthalenes via their Oxazoline Derivatives: A Convenient Route to 1-Substituted Naphthoic Acids," Synthesis Communications, 2:105-107 (1983).
Murase, K. et al. "New β-Adrenoreceptor Stimulants. Studies on 3-Acylamino-4-hydroxy-α-(N-substituted aminomethyl)benzyl Alcohols," Chem. Pharm. Bull., 25(6): 1368-1377 (1977).
Nielsen, K.G. et al. "Flow-dependent effect of formoterol dry-powder inhaled from the Aerolizer®," Eur. Respir. Journal, 10: 2105-2109 (1997).
Notice of Allowanced dated Jan. 26, 2011 in U.S. Appl. No. 11/920,561.
Office Action dated Jun. 2, 2010 in U.S. Appl. No. 11/920,561.
Office Action (Quayle Action) dated Nov. 9, 2010 in U.S. Appl. No. 11/920,561.
Office Action dated Mar. 9, 2011 in U.S. Appl. No. 12/745,195.
Portoghese, P.S. "Stereochemical Studies on Medicinal Agents. 19. X-Ray Crystal Structures of Two (±)-Allylprodine Diastereomers. The Role of the Allyl Group in Conferring High Stereoselectivity and Potency at Analgetic Receptors," Journal of Medicinal Chemistry, 19(1): 55-57 (1976).
Restriction Requirement dated Mar. 16, 2010 in U.S. Appl. No. 11/920,561.
Restriction Requirement dated Jan. 5, 2011 in U.S. Appl. No. 12/745,195.
Silverman, RB "The Organic Chemistry of Drug Design and Drug Action," Academic Press, Chapter 2, pp. 10-23 (1992).
Smart, BE. "Fluorine substituent effects (on bioactivity)," Journal of Fluorine Chemistry 109:3-11 (2001).
Sterling, J. et al. "Novel Dual Inhibitors of AChE and MAO Derived from Hydroxy Aminoindan and Phenethylamine as Potential Treatment of Alzheimer's Disease," J. Med. Chem. 45(24): 5260-5279 (2002).
Svenson, R. et al. "On the Hydrozirconation of Some Long-Chain Unsaturated Fatty Acid Oxazolines," Chemica Scripta., 19: 149-153 (1982).
Vippagunta, SR et al. "Crystalline Solids," Advanced Drug Delivery Reviews, 48: 3-26 (2001).
Yang, Z. et al. "A Novel and Practical Method for the Preparation of α,α-Difluoro Functionalized Esters," J. Chem. Soc., Chem. Commun., 3:233-234 (1992).
Yang, Z. "Synthesis of new α,α,β,β-tetrafluoroesters," Journal of Fluorine Chemistry, 125: 763-765 (2004).
Yoshizaki, S. et al. "Sympathomimetic Amines having a 3,4-Dihydrocarbostyril Nucleus," Chemical and Pharmaceutical Bulletin, 26(5): 1611-1614 (1978).
Yoshizaki, S. et al. "Sympathomimetic Amines Having a Carbostyril Nucleus," Journal of Medicinal Chemistry, 19(9): 1138-1142 (1976).
Interview Summary dated Feb. 22, 2012, for U.S. Appl. No. 12/745,195.
Notice of Allowability dated Feb. 24, 2012 in U.S. Appl. No. 12/745,195.
Office Action dated Jan. 26, 2012 in U.S. Appl. No. 12/298,131.
Office Action dated Jan. 30, 2012 in U.S. Appl. No. 12/444,935.
Office Action dated Apr. 24, 2012, in U.S. Appl. No. 12/526,090.
Office Action (Advisory Action) dated Jun. 4, 2012, in U.S. Appl. No. 12/444,935.

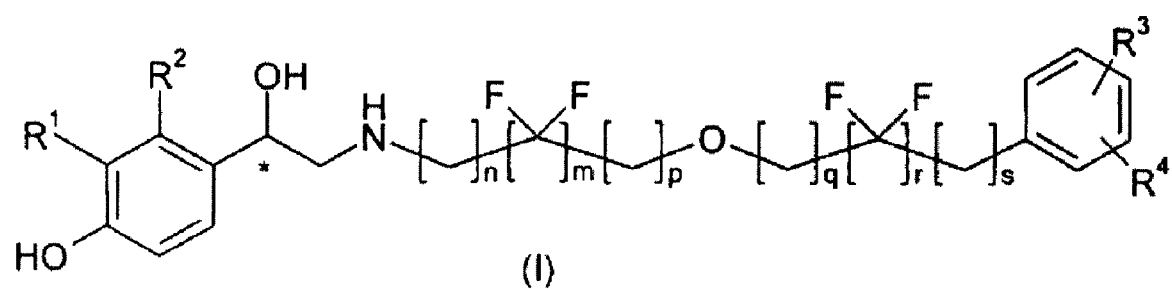
(I)

DERIVATIVES OF 4-(2-AMINO-1-HYDROXYETHYL)PHENOL AS AGONISTS OF THE β2 ADRENERGIC RECEPTOR

This application is a divisional of application Ser. No. 11/920,561, which has a §371 date of Feb. 11, 2008 now U.S. Pat. No. 7,964,615, and which is the U.S. national stage application of International Application No. PCT/EP2006/004680 filed on May 17, 2006, which claims the benefit of priority from Spanish Patent Application No. P200501229, filed on May 20, 2005. Both of these applications are herein incorporated by reference.

FIELD OF THE INVENTION

The present invention is directed to novel β2 adrenergic receptor agonists. The invention is also directed to pharmaceutical compositions comprising such compounds, methods of using such compounds to treat diseases associated with β2 adrenergic receptor activity, and processes and intermediates useful for preparing such compounds.

BACKGROUND OF THE INVENTION

β2 adrenergic receptor agonists are recognized as effective drugs for the treatment of pulmonary diseases such as asthma and chronic obstructive pulmonary disease (including chronic bronchitis and emphysema). β2 adrenergic receptor agonists are also useful for treating pre-term labor, glaucoma and are potentially useful for treating neurological disorders and cardiac disorders.

In spite of the success that has been achieved with certain β2 adrenergic receptor agonists, current agents possess less than desirable potency, selectivity, onset, and/or duration of action. Thus, there is a need for additional β2 adrenergic receptor agonists having improved properties. Preferred agents may possess, among other properties, improved potency, selectivity, onset, improved safety margins, improved therapeutic window and/or duration of action.

BRIEF DESCRIPTION OF THE DRAWING

FIG. 1 shows compounds of formula (I) in accordance with embodiments described in this application.

SUMMARY OF THE INVENTION

The invention provides novel compounds that possess β2 adrenergic receptor agonist activity. Accordingly, there is provided a compound of the invention which is a compound of formula (I):

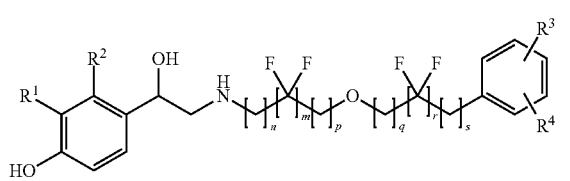

(I)

wherein:
$R^1$ is a group selected from —$CH_2OH$, —NHC(O)H and $R^2$ is a hydrogen atom; or $R^1$ together with $R^2$ form the group —NH—C(O)—CH=CH— wherein the nitrogen atom is bound to the carbon atom in the phenyl ring holding $R^1$ and the carbon atom is bound to the carbon atom in the phenyl ring holding $R^2$ $R^3$ is selected from hydrogen and halogen atoms or groups selected from —SO—$R^5$, —$SO_2$—$R^5$, —NH—CO—$NH_2$, —$CONH_2$, hydantoino, $C_{1-4}$alkyl, $C_{1-4}$alkoxy and —$SO_2NR^5R^6$ $R^4$ is selected from hydrogen atoms, halogen atoms and $C_{1-4}$alkyl groups $R^5$ is a $C_{1-4}$alkyl group or $C_{3-8}$cycloalkyl group $R^6$ is independently selected from hydrogen atoms and $C_{1-4}$alkyl groups n, p and q are independently 0, 1, 2, 3 or 4
m and s are independently 0, 1, 2 or 3
r is 0, 1 or 2
  with the provisos that:
    at least one of m and r is not 0
    the sum n+m+p+q+r+s is 7, 8, 9, 10, 11, 12 or 13
    the sum q+r+s is 2, 3, 4, 5 or 6
or a pharmaceutically-acceptable salt or solvate or stereoisomer thereof.

The invention also provides a pharmaceutical composition comprising a compound of the invention and a pharmaceutically-acceptable carrier. The invention further provides combinations comprising a compound of the invention and one or more other therapeutic agents and pharmaceutical compositions comprising such combinations.

The invention also provides a method of treating a disease or condition associated with β2 adrenergic receptor activity (e.g. a pulmonary disease, such as asthma or chronic obstructive pulmonary disease, pre-term labor, glaucoma, a neurological disorder, a cardiac disorder, or inflammation) in a mammal, comprising administering to the mammal, a therapeutically effective amount of a compound of the invention. The invention further provides a method of treatment comprising administering a therapeutically effective amount of a combination of a compound of the invention together with one or more other therapeutic agents.

In separate and distinct aspects, the invention also provides synthetic processes and intermediates described herein, which are useful for preparing compounds of the invention.

The invention also provides a compound of the invention as described herein for use in medical therapy, as well as the use of a compound of the invention in the manufacture of a formulation or medicament for treating a disease or condition associated with β2 adrenergic receptor activity (e.g. a pulmonary disease, such as asthma or chronic obstructive pulmonary disease, pre-term labor, glaucoma, a neurological disorder, a cardiac disorder, or inflammation) in a mammal.

DETAILED DESCRIPTION OF THE INVENTION

When describing the compounds, compositions and methods of the invention, the following terms have the following meanings, unless otherwise indicated.

The term "therapeutically effective amount" refers to an amount sufficient to effect treatment when administered to a patient in need of treatment.

The term "treatment" as used herein refers to the treatment of a disease or medical condition in a human patient which includes:
(a) preventing the disease or medical condition from occurring, i.e., prophylactic treatment of a patient;
(b) ameliorating the disease or medical condition, i.e., causing regression of the disease or medical condition in a patient;

(c) suppressing the disease or medical condition, i.e., slowing the development of the disease or medical condition in a patient; or (d) alleviating the symptoms of the disease or medical condition in a patient.

The phrase "disease or condition associated with β2 adrenergic receptor activity" includes all disease states and/or conditions that are acknowledged now, or that are found in the future, to be associated with β2 adrenergic receptor activity. Such disease states include, but are not limited to, pulmonary diseases, such as asthma and chronic obstructive pulmonary disease (including chronic bronchitis and emphysema), as well as neurological disorders and cardiac disorders. β2 adrenergic receptor activity is also known to be associated with pre-term labor (see International Patent Application Publication Number WO 98/09632), glaucoma and some types of inflammation (see International Patent Application Publication Number WO 99/30703 and Patent Application Publication Number EP 1 078 629).

The term "pharmaceutically-acceptable salt" refers to a salt prepared from a base or acid which is acceptable for administration to a patient, such as a mammal. Such salts can be derived from pharmaceutically-acceptable inorganic or organic bases and from pharmaceutically-acceptable inorganic or organic acids.

Salts derived from pharmaceutically-acceptable acids include acetic, benzenesulfonic, benzoic, camphosulfonic, citric, ethanesulfonic, fumaric, gluconic, glutamic, hydrobromic, hydrochloric, lactic, maleic, malic, mandelic, methanesulfonic, mucic, nitric, pantothenic, phosphoric, succinic, sulfuric, tartaric, p-toluenesulfonic, xinafoic (1-hydroxy-2-naphthoic acid) and the like. Particularly preferred are salts derived from fumaric, hydrobromic, hydrochloric, acetic, sulfuric, methanesulfonic, xinafoic, and tartaric acids.

Salts derived from pharmaceutically-acceptable inorganic bases include aluminum, ammonium, calcium, copper, ferric, ferrous, lithium, magnesium, manganic, manganous, potassium, sodium, zinc and the like. Particularly preferred are ammonium, calcium, magnesium, potassium and sodium salts.

Salts derived from pharmaceutically-acceptable organic bases include salts of primary, secondary and tertiary amines, including substituted amines, cyclic amines, naturally-occurring amines and the like, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like.

The term "solvate" refers to a complex or aggregate formed by one or more molecules of a solute, i.e. a compound of the invention or a pharmaceutically-acceptable salt thereof, and one or more molecules of a solvent. Such solvates are typically crystalline solids having a substantially fixed molar ratio of solute and solvent. Representative solvents include by way of example, water, methanol, ethanol, isopropanol, acetic acid, and the like. When the solvent is water, the solvate formed is a hydrate.

It will be appreciated that the term "or a pharmaceutically-acceptable salt or solvate of stereoisomer thereof" is intended to include all permutations of salts, solvates and stereoisomers, such as a solvate of a pharmaceutically-acceptable salt of a stereoisomer of a compound of formula (I).

The term "amino-protecting group" refers to a protecting group suitable for preventing undesired reactions at an amino nitrogen. Representative amino-protecting groups include, but are not limited to, formyl; acyl groups, for example alkanoyl groups, such as acetyl; alkoxycarbonyl groups, such as tert-butoxycarbonyl (Boc); arylmethoxycarbonyl groups, such as benzyloxycarbonyl (Cbz) and 9-fluorenylmethoxycarbonyl (Fmoc); arylmethyl groups, such as benzyl (Bn), trityl (Tr), and 1,1-di-(4'-methoxyphenyl)methyl; silyl groups, such as trimethylsilyl (TMS) and tert-butyldimethylsilyl (TBS); and the like.

The term "hydroxy-protecting group" refers to a protecting group suitable for preventing undesired reactions at a hydroxy group. Representative hydroxy-protecting groups include, but are not limited to, alkyl groups, such as methyl, ethyl, and tert-butyl; acyl groups, for example alkanoyl groups, such as acetyl; arylmethyl groups, such as benzyl (Bn), p-methoxybenzyl (PMB), 9-fluorenylmethyl (Fm), and diphenylmethyl (benzhydryl, DPM); silyl groups, such as trimethylsilyl (TMS) and tert-butyldimethylsilyl (TBS); and the like.

The compounds of the invention contain at least a chiral center. Accordingly, the invention includes racemic mixtures, enantiomers, and mixtures enriched in one or more stereoisomer. The scope of the invention as described and claimed encompasses the racemic forms of the compounds as well as the individual enantiomers, diastereomers, and stereoisomer-enriched mixtures.

In an embodiment the compounds of the present invention have at least one of m and r with a value of 1.

In another embodiment the compounds of the present invention have the sum m+r with a value of 1.

In still another embodiment the compounds of the present invention have the sum n+m+p+q+r+s with a value of 8, 9 or 10.

In still another embodiment the compounds of the present invention have the sum q+r+s with a value of 2, 3 or 4.

In still another embodiment the compounds of he present invention have s with a value of 0 or 1.

In still another embodiment the compounds of the present invention have the sum n+p with a value of 4, 5 or 6.

In still another embodiment the compounds of the present invention have the sum q+s with a value of 1, 2, 3 or 4.

In still another embodiment the compounds of the present invention have $R^3$ selected from the group consisting of a hydrogen atom, an halogen atom or a methyl group.

In still another embodiment the compounds of the present invention have $R^3$ selected from the group consisting of chlorine or fluorine atom.

In still another embodiment the compounds of the present invention have $R^3$ being a methyl group.

In still another embodiment the compounds of the present invention have $R^4$ being a hydrogen atom.

In still another embodiment the compounds of the present invention have $R^4$ being a chlorine atom.

In still another embodiment the compounds of the present invention have m and s with a value of 0, r and q with a value of 1, the sum of n and p with a value of 6 and $R^5$ and $R^6$ being both hydrogen atoms Of particular interest are the compounds:
(R,S)-4-(2-{[6-(2,2-Difluoro-4-phenylbutoxy)hexyl] amino}-1-hydroxy-ethyl)-2-(hydroxymethyl)phenol
(R,S)-4-(2-{[6-(2,2-Difluoro-2-phenylethoxy)hexyl] amino}-1-hydroxy-ethyl)-2-(hydroxymethyl)phenol
(R,S)-4-(2-{[4,4-Difluoro-6-(4-phenylbutoxy)hexyl] amino}-1-hydroxy-ethyl)-2-(hydroxymethyl)phenol (R,S)-4-(2-{[6-(4,4-Difluoro-4-phenylbutoxy)hexyl]
    amino}-1-hydroxy-ethyl)-2-(hydroxymethyl)phenol
(R,S)-5-(2-{[6-(2,2-Difluoro-2-phenylethoxy)hexyl]
    amino}-1-hydroxy-ethyl)-8-hydroxyquinolin-2(1H)-one
(R,S)-4-[2-({6-[2,2-Difluoro-2-(3-methylphenyl)ethoxy]
    hexyl}amino)-1-hydroxyethyl]-2-(hydroxymethyl)phenol
4-(1R)-2-{[6-(2,2-Difluoro-2-phenylethoxy)hexyl]amino}-
    1-hydroxyethyl)-2-(hydroxymethyl)phenol
(R,S)-2-(Hydroxymethyl)-4-(1-hydroxy-2-{[4,4,5,5-tet-
    rafluoro-6-(3-phenylpropoxy)hexyl]amino}ethyl)phenol
(R,S)-[5-(2-{[6-(2,2-Difluoro-2-phenylethoxy)hexyl]
    amino}-1-hydroxy-ethyl)-2-hydroxyphenyl]formamide
(R,S)-4-[2-({6-[2-(3-Bromophenyl)-2,2-difluoroethoxy]
    hexyl}amino)-1-hydroxyethyl]-2-(hydroxymethyl)phenol
(R,S)-N-[3-(1,1-Difluoro-2-{[5-({2-hydroxy-2-[4-hydroxy-
    3-(hydroxymethyl)phenyl]ethyl}amino)hexyl]oxy}ethyl)
    phenyl]urea
(R,S)-3-[3-(1,1-difluoro-2-{[6-({2-hydroxy-2-[4-hydroxy-
    3-(hydroxymethyl)phenyl]ethyl}amino)hexyl]oxy}ethyl)
    phenyl]imidazolidine-2,4-dione
(R,S)-4-[2-({6-[2,2-difluoro-2-(3-methoxyphenyl)ethoxy]
    hexyl}amino)-1-hydroxyethyl]-2-(hydroxymethyl)phenol
5-((1R)-2-{[6-(2,2-difluoro-2-phenylethoxy)hexyl]amino}-
    1-hydroxyethyl)-8-hydroxyquinolin-2(1H)-one
4-((1R)-2-{[4,4-Difluoro-6-(4-phenylbutoxy)hexyl]amino}-
    1-hydroxy-ethyl)-2-(hydroxymethyl)phenol
(R,S)-4-(2-{[6-(3,3-Difluoro-3-phenylpropoxy)hexyl]
    amino}-1-hydroxy ethyl)-2-(hydroxymethyl)phenol
(R)-4-(2-{[6-(2,2-Difluoro-2-phenylethoxy)-4,4-difluoro-
    hexyl]amino}-1-hydroxyethyl)-2-(hydroxymethyl)phenol
(R,S)-4-(2-{[5-(2,2-difluoro-3-phenylpropoxy)hexyl]
    amino}-1-hydroxy    ethyl}-2-(hydroxymethyl)phenol,
    hydrochloride
and pharmaceutically-acceptable salts and solvates thereof.

The invention comprises also pharmaceutical compositions comprising a therapeutically effective amount of a compound as hereinabove defined and a pharmaceutically acceptable carrier.

In an embodiment of the present invention the pharmaceutical composition further comprises a therapeutically effective amount of one or more other therapeutic agents.

It is also an embodiment of the present invention that the pharmaceutical composition is formulated for administration by inhalation.

The compounds of the present invention as hereinabove defined may also be combined with one or more other therapeutic agents, in particular one or more drugs selected from the group consisting of corticosteroids, an antichlolinergic agents and PDE4 inhibitors.

In a preferred embodiment of the present invention the combination comprises a compound of formula (I) as hereinabove defined and a drug selected from the group consisting of fluticasone propionate, 6α,9α-difluoro-17α-[-(2-furanyl-carbonyl)oxy]-11β-hydroxy-16α-methyl-3-oxo-androsta-1, 4-diene-17β-carbothioic acid S-fluoromethyl ester, and 6α,9α-difluoro-11β-hydroxy-16α-methyl-3-oxo-17.alpha.-propionyloxy-androsta-1,4-diene-17β-carbothioic acid S-(2-oxo-tetrahydro-furan-3S-yl) ester.

The invention is also directed to a method of treating a disease or condition in a mammal associated with β2 adrenergic receptor activity, the method comprising administering to the mammal, a therapeutically effective amount of a pharmaceutical composition comprising a β2 adrenergic receptor agonist according to the present invention. It is of particular relevance the method applied to the treatment of a disease or condition which is a pulmonary disease, preferably asthma or chronic obstructive pulmonary disease.

The method of treating a disease can also be applied within the scope of the present invention to the treatment of a disease or condition selected from the group consisting of pre-term labor, glaucoma, neurological disorders, cardiac disorders, and inflammation.

General Synthetic Procedures

The compounds of the invention can be prepared using the methods and procedures described herein, or using similar methods and procedures. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. The choice of a suitable protecting group for a particular functional group, as well as suitable conditions for protection and deprotection, are well known in the art. For example, numerous protecting groups, and their introduction and removal, are described in T. W. Greene and G. M. Wuts, Protecting Groups in Organic Synthesis, Third Edition, Wiley, New York, 1999, and references cited therein.

Processes for preparing compounds of the invention are provided as further embodiments of the invention and are illustrated by the procedures below.

In general the compounds of formula (I) are obtained reacting a compound of formula (II):

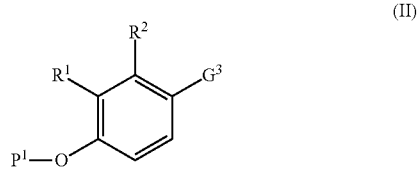

(II)

wherein $R^1$ and $R^2$ are as hereinabove defined, $P^1$ is a conventional hydroxy protecting group such as benzyl group; with a compound of formula (III):

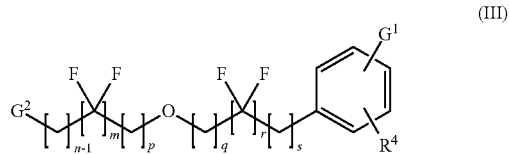

(III)

wherein n, m p, q, r and s are as hereinabove defined and $G^1$ is a group selected from:

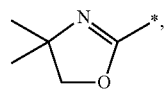

hydrogen or halogen atoms or groups selected from $C_{1-4}$ alkyl, $C_{1-4}$ alkoxy, S—$R^5$, SO—$R^5$ and $SO_2$—$R^5$ wherein $R^5$ is a $C_{1-4}$ alkyl and $C_{3-6}$ cycloalkyl and $R^4$ is selected from hydrogen atom, halogen atoms and $C_{1-4}$ alkyl groups.

The nature of the reacting groups $G^3$ and $G^2$ depends on the coupling reaction that is employed to obtain the compounds of formula (I). The different coupling reactions between compound (II) (the phenylethanolamine moiety) and the corresponding compound (III) (the fluorinated moeity) are summarised in Scheme 1 and described below.
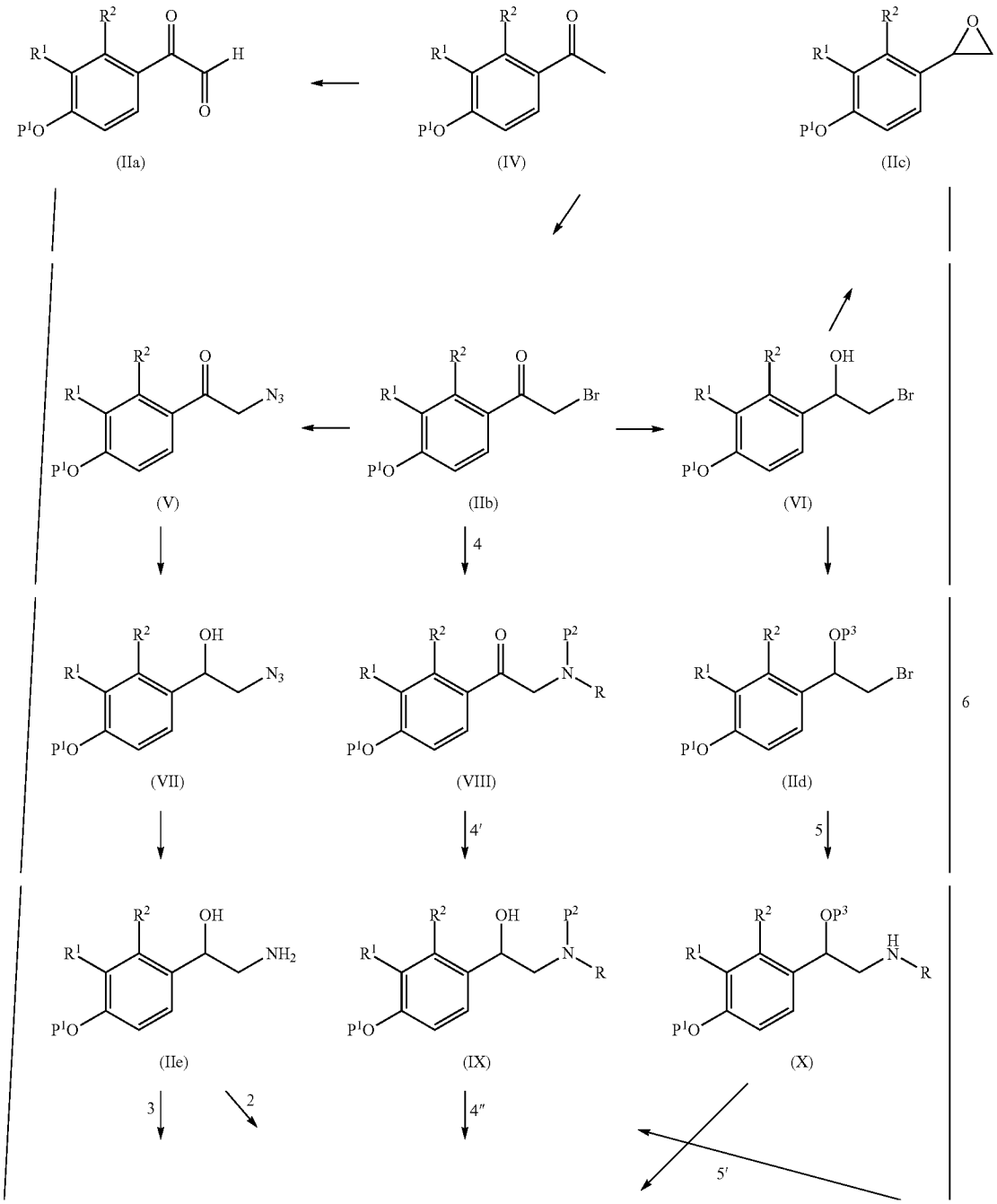

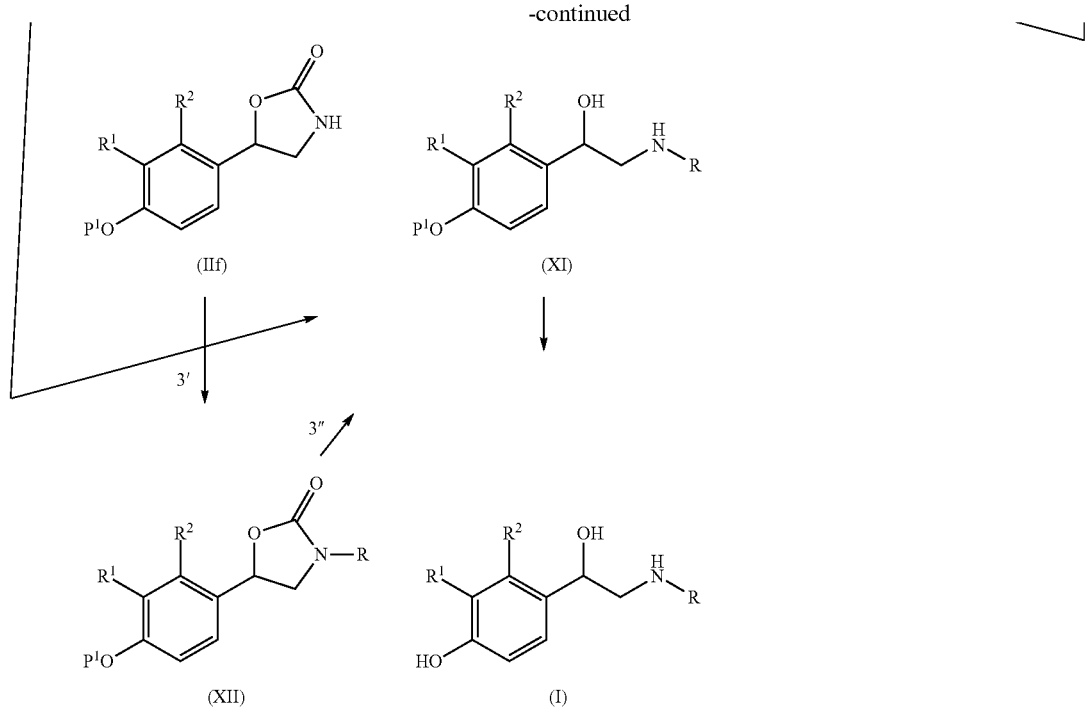

wherein R represents a group of formula:

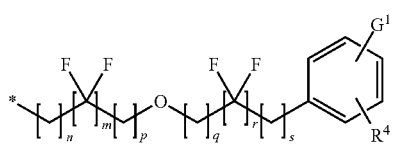

In a first alternative phenylglyoxals of formula (IIa) (corresponding to compounds of general formula (II) wherein $G^3$ is a —CO—CHO group) can react with a compound of formula (IIIf) (corresponding to compounds of general formula (III) wherein $G^2$ is a group —CH$_2$NH$_2$) to give, in a reductive alkylation step, intermediates of formula (XI). This step can be achieved in a variety of solvents, like tetrahydrofuran, alcohols as methanol, ethanol or isopropyl alcohol, as well as a mixture of solvents such as methanol/tetrahydrofuran or dimethylsulfoxide/methanol, the temperature range being between 5° and 100° C.; more specifically between 15° and 70° C. The reducing agent may be a hydride like sodium borohydride or sodium cyanoborohydride as well as hydrogen plus a hydrogenation catalyst like palladium on charcoal.

In a second alternative aminoalcohols of formula (IIe) (corresponding to compounds of general formula (II) wherein $G^3$ is a —CH(OH)—CH$_2$NH$_2$ group) can react with an aldehyde compound of formula (IIIc) (corresponding to compounds of general formula (III) wherein $G^2$ is a group —CHO) to give, in an analogous reductive alkylation process the same intermediates of formula (XI). This step is carried out under similar conditions and solvents as the previously described.

In a third alternative compounds of formula (IIe) (corresponding to compounds of general formula (II) wherein $G^3$ is a —CH(OH)—CH$_2$NH$_2$ group) are converted to the corresponding oxazolidinones derivatives of formula (IIf) (corresponding to compounds of general formula (II) wherein $G^3$ is an oxazolidinone group) by means of a carbonylation reagent like biscarbonyldiimidazole or a two-step process involving firstly treatment with di-terbutyldicarbonate to give the corresponding N—BOC derivative and subsequent cyclization with a base like sodium hydride. The resulting oxazolidinones of formula (IIf) can react with an alkylating agent of formula (IIId) or (IIIb) (corresponding to compounds of general formula (III) wherein $G^2$ is a group —CH$_2$Br or a group —CH$_2$OMs (Ms standing for a mesylate group)) in the presence of a base like sodium hydride to give intermediates of formula (XII). Subsequent hydrolysis of the oxazolidinone moiety by means of a basic reagent such as an alkaline hydroxide or alkoxide like potassium trimethylsilanolate yields the compound of formula (XI) (corresponding to compounds of general formula (II) wherein $G^2$ is a —CH(OH)—CH$_2$—NH—R).

In a fourth alternative the phenacyl bromides of formula (IIb) (wherein $G^3$ is a —CO—CH$_2$—Br group) can react with protected amines of formula (IIIe) (corresponding to compounds of general formula (III) wherein $G^2$ is a group —CH$_2$—NH—P$^2$ being P$^2$ a conventional amine protecting group such as a benzyl group), to give ketoamines of formula (VIII). This process can be carried out in many solvents like tetrahydrofuran or dichloromethane in the presence of an acid scavenger like a tertiary amine as triethylamine, and at temperatures between 5 and 60° C. The compounds of formula (VIII) can then be reduced to yield the aminoalcohols of formula (IX). This step can be achieved in a variety of solvents, like tetrahydrofuran, alcohols as methanol, ethanol or isopropyl alcohol, as well as a mixture of solvents such as methanol/tetrahydrofuran or dimethylsulfoxide/methanol, the temperature range being between 5° and 100° C.; more specifically between 15° and 70° C. The reducing agent may be a hydride like sodium borohydride or sodium cyanoborohydride as well as hydrogen plus a hydrogenation catalyst like palladium on charcoal. Finally the protecting group—usually being a benzyl group—can be removed by means of hydrogenation with the same catalysts and conditions described above to yield the compounds of formula (XI).

In a fifth alternative protected bromohydrins of formula (IId) (corresponding to compounds of general formula (II) wherein $G^3$ is a group —CH(OP$^3$)—CH$_2$—Br (P$^3$ being a conventional hydroxy protecting group such as a silyl ether)) can alkylate primary amines of formula (IIIf) (corresponding to compounds of general formula (III) wherein $G^2$ is a group —CH$_2$NH$_2$) to give intermediates of formula (X). This reaction is carried out in the presence of an acid scavenger, such as a tertiary amine or sodium bicarbonate, in a variety of solvents like dioxane, dimethylsulfoxide or also without solvent, in a range of temperatures between 60° and 140° C. The removal of the protecting group PG, usually a silyl ether, is achieved by means of the fluoride anion, for example in the form of a quaternary ammonium salt like tetrabutylammonium fluoride, to give intermediates of formula (XI).

In a sixth alternative epoxides of formula (IIc) (corresponding to compounds of general formula (II) wherein $G^3$ is an oxyran group) can also react with protected amines of formula (IIIe) (corresponding to compounds of general formula (III) wherein $G^2$ is a group —CH$_2$—NH—P$^2$ being P$^2$ a conventional amine protecting group such as a benzyl group), to give intermediates of formula (IX). This process can be carried out in many solvents like alcohols, tetrahydrofuran or without solvents at all, in a range of temperatures between 20° and 140° C.

As a final step the compounds of formula (XI) are deprotected to the target compounds of formula (I) by conventional methods. When the protecting group $P^1$ is a benzyl group the debenzylation is carried out with hydrogen and a hydrogenation catalyst like palladium on charcoal. This step is achieved using a variety of solvents like alcohols, tetrahydrofuran or mixtures of them, and in neutral or slightly acidic media. The pressure of hydrogen lies between $6.90 \cdot 10^4$ Pa and $2.76 \cdot 10^5$ Pa and the temperature between 10° and 30° C.

The intermediates of formulae (IIa), (IIb), (IIc), (IId), (IIe) and (IIf) may be obtained by methods well known in the literature starting from the phenylglyoxals of formula (IIa) or the corresponding hydrates—prepared from the corresponding acetophenones of formula (IV) (for ex., see EP 85166454, example 2; U.S. Pat. No. 4,753,962 description 54 or GB 1247370, example 1).

For example the phenylethanolamines of formula (IIe) may be obtained following methods described in J. Med. Chem., 1976, 19(9), 1138, compound 19; DE 2461861, example 24. The phenacyl bromides of formula (IIb) may be obtained following methods described in Chem. Pharm. Bull., 1977, 25(6), 1368, compound II; J. Med. Chem., 1974, 17(1), 49; EP 85166454, example 1). The protected bromohydrines of formula (IId) may be obtained following methods described in US2004059116 example 9C, WO 2004/011416 example 2 and WO 2004/016578 Example 1ii, The oxyranes of formula (IIc) may be obtained following methods described in WO 01036375, preparation 12; J. Med. Chem., 1974, 17(1), 55).

Many of these intermediates may also exist in an enantiomerically pure form (see, for ex., Organic Process Research & Development 1998, 2, 96; Tetrahedron Lett., 1994, 35(50), 9375; WO 02070490 example 1/X; EP 0147719).

As it has been explained before, the nature of the $G^2$ group in the compounds of formula (III) depends on the coupling reaction followed to obtain compounds (I) of the present invention. Schema 2 illustrates the interconversion of compounds of formula (III) having different $G^2$ groups.

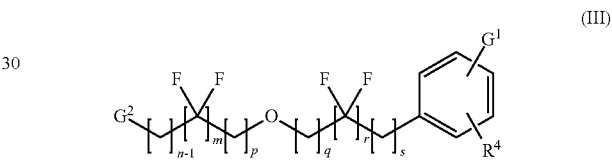

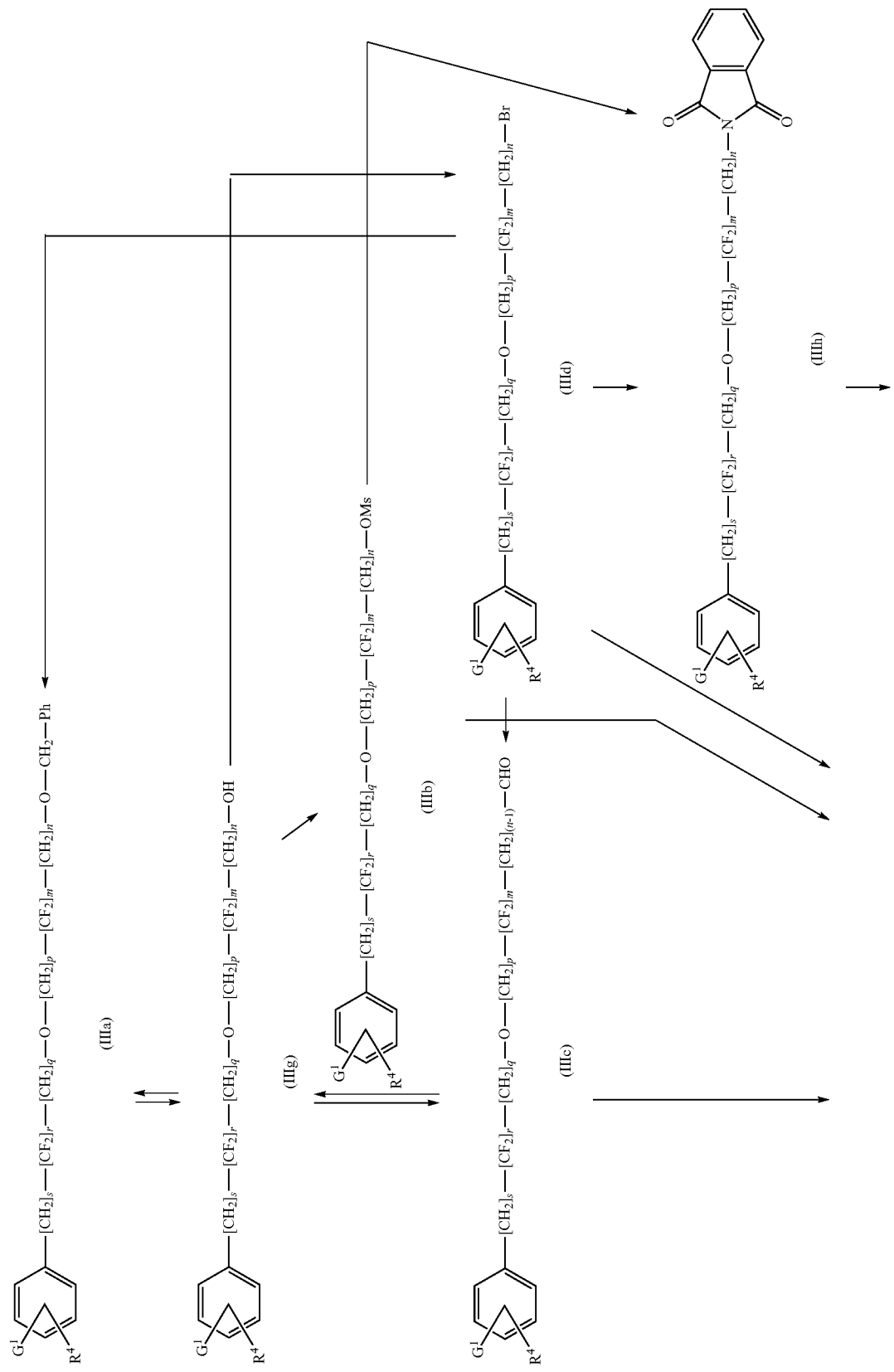

-continued
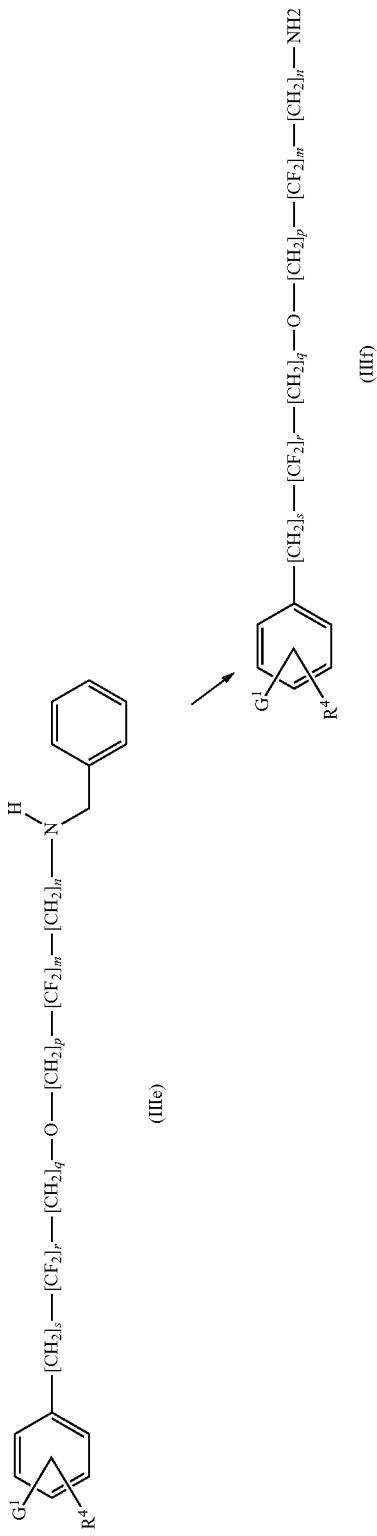
(IIIe)
(IIIf)

Wherein $G^1$, $R^4$, n, m, p, q, r, and s are as defined above.

Hydrogenation of compounds of formula (IIIa) (corresponding to compounds of general formula (III) wherein $G^2$ is a group —$CH_2$—OBz) yields alcohols of formula (IIIg) (corresponding to compounds of general formula (III) wherein $G^2$ is a group —$CH_2$—OH). The reaction can be carried out with a catalyst such as palladium on charcoal or platinum dioxide, in a solvent such as ethanol, methanol, ethyl acetate or dimethylformamide, at a temperature from room temperature to 70° C., and at a pressure from $1.38 \cdot 10^5$ Pa to $2.76 \cdot 10^5$ Pa.

Alcohols of formula (IIIg) (corresponding to compounds of general formula (III) wherein $G^2$ is a group —$CH_2$—OH) can react with benzyl bromide or benzyl chloride to give compounds of formula (IIIa) (corresponding to compounds of general formula (III) wherein $G^2$ is a group —$CH_2$—OBz). The reaction can be carried out with a base such as sodium hydroxide, potassium hydroxide or sodium hydride, optionally in the presence of a base transfer catalyst such as tetrabutylammonium bromide, with a solvent such as water, dimethylformamide, dimethylsulfoxide or diethylene glycol dimethyl ether, and at a temperature from 20° to 100° C.

Bromoderivatives of formula (IIId) (corresponding to compounds of general formula (III) wherein $G^2$ is a group —$CH_2$—Br) can be obtained from alcohols of formula (IIIg) (corresponding to compounds of general formula (III) wherein $G^2$ is a group —$CH_2$—OH) by reaction with lithium bromide, phosphorus tribromide, hydrobromic acid, carbon tetrabromide or thionyl bromide, optionally with a catalyst such as triphenylphosphine, with a solvent such as pyridine, benzene, toluene, methylene chloride, chloroform, acetonitrile, ethyl ether, tetrahydrofuran or acetone, and at temperature from 0° C. to the boiling point of the solvent.

Compounds of formula (IIIa) (corresponding to compounds of general formula (III) wherein $G^2$ is a group —$CH_2$—OBz) can also be obtained from bromoderivatives of formula (IIId) (corresponding to compounds of general formula (III) wherein $G^2$ is a group —$CH_2$—Br) and benzyl alcohol. The reaction can be carried out following the same experimental procedures described for the reaction of alcohols of formula (IIIg) and benzyl bromide or benzyl chloride.

Alcohols of formula (IIIg) (corresponding to compounds of general formula (III) wherein $G^2$ is a group —$CH_2$—OH) can be converted to compounds of formula (IIIb) (corresponding to compounds of general formula (III) wherein $G^2$ is a group —$CH_2$—OMs) by reaction with methanesulfonyl chloride, in the presence of a base such as triethylamine, diisopropylethylamine or pyridine, with a solvent such as methylene chloride, chloroform or tetrahydrofuran, and at a temperature from 0° C. to the boiling point of the solvent.

Oxidation of bromoderivatives of formula (IIId) (corresponding to compounds of general formula (III) wherein $G^2$ is a group —$CH_2$—Br) with an oxidant such as N-methylmorfoline N-oxide, 2-dimethylamino-N,N-dimethylaniline N-oxide, pyridine N-oxide or trimethylamine N-oxide gives compounds of formula (IIIc) (corresponding to compounds of general formula (III) wherein $G^2$ is a group —COH). The reaction is carried out in a solvent such as dimethylformamide, dimethylsulfoxide or acetonitrile, and at a temperature from room temperature to the boiling point of the solvent.

Aldehydes of formula (IIIc) (corresponding to compounds of general formula (III) wherein $G^2$ is a group —COH) can also be obtained by oxidation of alcohols of formula (IIIg) (corresponding to compounds of general formula (III) wherein $G^2$ is a group —$CH_2$—OH) by reaction with chromium trioxide, manganese dioxide, potassium dichromate, pyridinium chlorochromate, oxalyl chloride in dimethylsulfoxide or Dess-Martin reagent in a solvent such as pyridine, methylene chloride, chloroform, dimethylsulfoxide or acetonitrile, and at a temperature from −78° to 130° C.

Alcohols of formula (IIIg) (corresponding to compounds of general formula (III) wherein $G^2$ is a group —$CH_2$—OH) can also be synthesized by reduction of aldehydes of formula (IIIc) (corresponding to compounds of general formula (III) wherein $G^2$ is a group —COH). The reaction can be carried out with a hydride such as lithium aluminum hydride, sodium borohydride or diisobutylaluminum hydride in a solvent such as ethyl ether, diisopropyl ether, tetrahydrofuran or methanol, and at a temperature from room temperature to the boiling point of the solvent.

Bromoderivatives of formula (IIId) (corresponding to compounds of general formula (III) wherein $G^2$ is a group —$CH_2$—Br) and compounds of formula (IIIb) (corresponding to compounds of general formula (III) wherein $G^2$ is a group —$CH_2$—OMs) can react with potassium phtalimide to give compounds of formula (XIV). The reaction can be carried out in a solvent such as dimethylformamide, dimethylsulfoxide, acetonitrile or tetrahydrofuran, optionally with a catalyst such as (n-hexadecyl)tri-n-butylphosphonium bromide, and at a temperature from room temperature to the boiling point of the solvent.

The reaction of compounds of formula (IIIh) (corresponding to compounds of general formula (III) wherein $G^2$ is a group phthalimidomethyl) with hydrazine in a solvent such as methanol, ethanol, isopropyl alcohol or tetrahydrofuran, and at a temperature from 50 to 90° C. gives amines of formula (IIIf) (corresponding to compounds of general formula (III) wherein $G^2$ is a group —$CH_2$—$NH_2$).

Amines of formula (IIIf) (corresponding to compounds of general formula (III) wherein $G^2$ is a group —$CH_2$—$NH_2$) can also be obtained by alkylation of benzyl amine with bromoderivatives of formula (IIId) (corresponding to compounds of general formula (III) wherein $G^2$ is a group —$CH_2$—Br) or with compounds of formula (IIIb) (corresponding to compounds of general formula (III) wherein $G^2$ is a group —$CH_2$—OMs), followed by a debenzylation process.

Alkylation of benzyl amine with compounds of formula (IIIb) (corresponding to compounds of general formula (III) wherein $G^2$ is a group —$CH_2$—OMs) or with compounds of formula (IIId) (corresponding to compounds of general formula (III) wherein $G^2$ is a group —$CH_2$—Br) yields compounds of formula (IIIe) (corresponding to compounds of general formula (III) wherein $G^2$ is a group —$CH_2$—NH-Bz). The reaction can be carried out in the presence of a base such as benzyl amine, triethylamine, diisopropylethylamine or potassium carbonate, without solvent or in a solvent such as dimethylformamide, acetone, tetrahydrofuran or dioxane, and at temperature from 0° C. to the boiling point of the solvent. The debenzylation process to give amines of formula (IIIf) can be carried out with a catalyst such as palladium on charcoal or platinum dioxide, in a solvent such as ethanol, methanol, ethyl acetate, acetic acid or dimethylformamide, at a temperature from room temperature to 70° C., and at a pressure from $1.38 \cdot 10^5$ Pa to $2.76 \cdot 10^5$ Pa.

Amines of formula (IIIe) (corresponding to compounds of general formula (III) wherein $G^2$ is a group —$CH_2$—NH-Bz) can also be obtained from aldehydes of formula (IIIc) (corresponding to compounds of general formula (III) wherein $G^2$ is a group —COH) and benzyl amine. The reaction can be carried out with a hydride such as sodium borohydride or sodium cyanoborohydride in a solvent such as ethyl ether, diisopropyl ether, tetrahydrofuran or methanol or a mixture of them, and at a temperature from room temperature to the boiling point of the solvent.

In one alternative the compounds of formula (III)

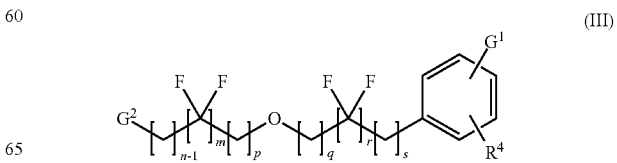

(III)

are obtained starting from compounds of formula (XV)
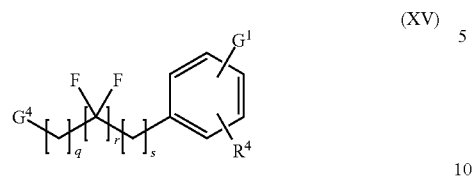
(XV)
wherein $G^1$, $G^2$, $R^4$, q, r, s are as hereinabove defined and $G^4$ is an halogen atom, preferably a bromine atom or a hydroxyl group through a variety of synthetic methods which are described below:

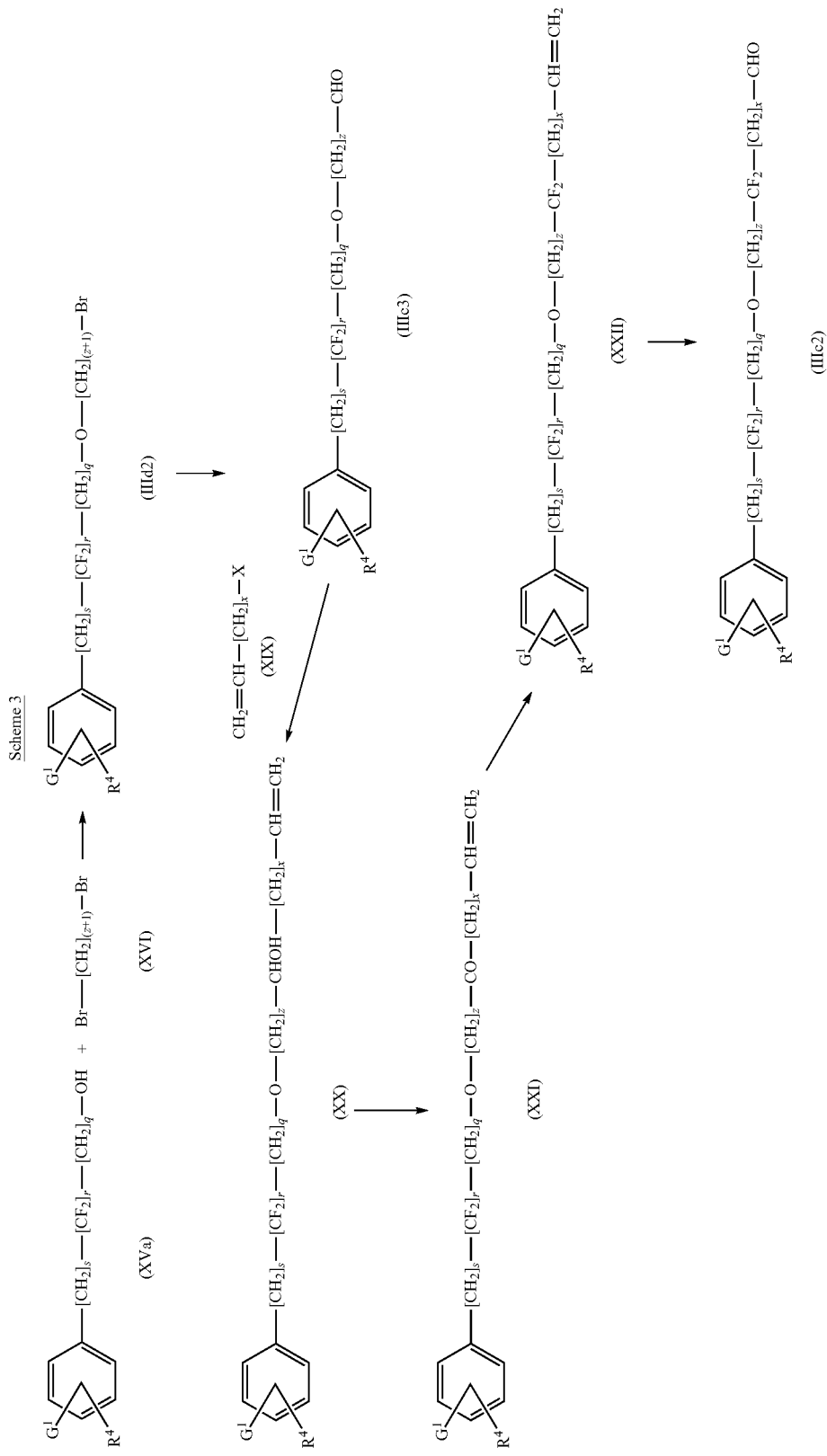

wherein $G^1$, $R^4$, s, r and q are as hereinabove defined; x is equal to n−1 and;

z is either equal to p when (IIIc2) is used as a product of formula (III) to be condensed with the adrenergic moiety or equal to p+n−1 when product (XVIII) is used to be condensed with the adrenergic moiety to obtain a product of formula (I) wherein m is zero.

Compounds of formula (IIId) (corresponding to compounds of general formula (III) wherein $G^2$ is a group —$CH_2$—Br) can be obtained by reaction of alcohols of formula (XVa) with dibromoderivatives of formula (XVI). The reaction can be carried out with a base such as sodium hydroxide, potassium hydroxide or sodium hydride, optionally in the presence of a base transfer catalyst such as tetrabutylammonium bromide, with a solvent such as water, dimethylformamide, dimethylsulfoxide or diethylene glycol dimethyl ether, and at a temperature from 20° to 100° C.

Bromoderivatives of formula (IIId) (corresponding to compounds of general formula (III) wherein $G^2$ is a group —$CH_2$—Br) can be converted to aldehydes of formula (IIIc3) (corresponding to compounds of general formula (III) wherein $G^2$ is a group —COH) by oxidation with an oxidant such as N-methylmorfoline N-oxide, 2-dimethylamino-N,N-dimethylaniline N-oxide, pyridine N-oxide or trimethylamine N-oxide. The reaction is carried out in a solvent such as dimethylformamide, dimethylsulfoxide or acetonitrile, and at a temperature from room temperature to the boiling point of the solvent.

The reaction of aldehydes of formula (IIIc3) (corresponding to compounds of general formula (III) wherein $G^2$ is a group —COH) with haloderivatives of formula (XIX) wherein X represents a halogen atom, such as chlorine, bromine or iodine, and magnesium gives alcohols of formula (XX). The reaction can be carried out with a solvent such as ethyl ether or tetrahydrofuran, and at a temperature from −78° to 80° C.

The reaction of alcohols of formula (XX) to yield ketones of formula (XXI) can be achieved by reaction with chromium trioxide, manganese dioxide, potassium dichromate, pyridinium chlorochromate, oxalyl chloride in dimethylsulfoxide or Dess-Martin reagent in a solvent such as pyridine, methylene chloride, chloroform, dimethylsulfoxide or acetonitrile, and at a temperature from −78° to 130° C.

Ketones of formula (XXI) can be transformed to compounds of formula (XXII) by reaction with a fluorinated agent such as (diethylamino) sulfur trifluoride (DAST) or [di(methoxyethyl)amino]sulfur trifluoride, optionally in the presence of a solvent such as methylene chloride, chloroform, methanol, ethanol or tetrahydrofuran, and at a temperature from room temperature to the boiling point of the solvent.

Alkenes of formula (XXX) can be converted to aldehydes of formula (IIIc2) (corresponding to compounds of general formula (III) wherein $G^2$ is a group —COH) by oxidation with sodium periodate or potassium periodate with a catalytic amount of osmium tetroxide. The reaction can be carried out in a solvent such as dioxane, tetrahydrofuran, methanol, ethanol, acetonitrile or water, or a mixture of them, and at a temperature from −78° C. to 100° C.

In another alternative the compounds of formula (III) wherein $G^1$, $R^4$, s, r and q are as hereinabove defined may be obtained following the method depicted in Scheme 4.

Scheme 4

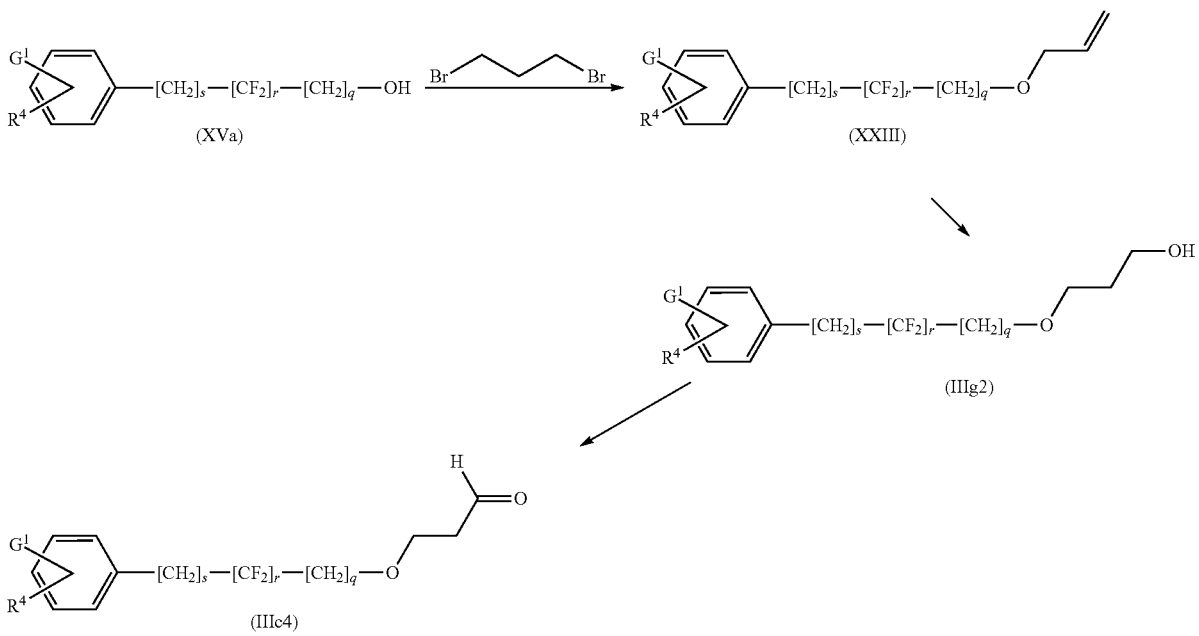

The reaction of alcohols of formula (XVa) (corresponding to compounds of general formula (XV) wherein $G^4$ is a group —OH) with 1,3-dibromopropane gives alkenes of formula (XXIII). The reaction can be carried out following the same experimental procedure described for the synthesis of compounds of formula (IIId2).

Alcohols of formula (IIIg2) (corresponding to compounds of general formula (III) wherein $G^2$ is a group —$CH_2$—OH, m is 0 and p+n is 2) can be obtained from alkenes of formula (XXIII) by successive reaction with borane tetrahydrofuran complex or borane-methyl sulfide complex and hydrogen peroxide, in the presence of a base such as sodium hydroxide or potassium hydroxide in a solvent such as tetrahydrofuran, dioxane, water or diethylene glycol dimethyl ether, and at a temperature from −78° C. to 100° C.

The conversion of compounds of formula (IIIg2) (corresponding to compounds of general formula (III) wherein $G^2$ is a group —$CH_2$—OH, m is 0 and p+n is 2) to aldehydes of formula (IIIc4) (corresponding to compounds of general formula (III) wherein $G^2$ is a group —COH, m is 0 and p+n is 2) can be achieved following by reaction with chromium trioxide, manganese dioxide, potassium dichromate, pyridinium chlorochromate, oxalyl chloride in dimethylsulfoxide or Dess-Martin reagent in a solvent such as pyridine, methylene chloride, chloroform, dimethylsulfoxide or acetonitrile, and at a temperature from −78° to 130° C.

In still another alternative the compounds of formula (IIIi) (corresponding to compounds of general formula (III) wherein $G^2$ is a group —OH, $G^1$, $R^4$, s, r, q and p are as hereinabove defined and m and n are both 1) may be obtained following the method depicted in Scheme 5.

general formula (III) wherein $G^2$ is a group —$CH_2$—OH, m is 0) with 2-nitrophenyl selenocyanate and tributylphosphine, with a solvent such as tetrahydrofuran, ethyl ether or dioxane, and at a temperature from room temperature to the boiling point of the solvent (see references Hart, D. J.; Kenai, K.-I.; *J. Am. Chem. Soc.* 1983, 105, 1255, Hart, D. J.; *J. Org. Chem.* 1981, 46, 3575). Alcohols of formula (XVIIb) can also react with p-toluensulfonyl chloride or methylsulfonyl chloride, in a solvent such as tetrahydrofuran, ethyl ether, dioxane or methylene chloride, and at a temperature from room temperature to the boiling point of the solvent. The resulting intermediate reacts with a base such as potassium hydroxide, sodium hydroxide, triethylamine or diisopropylethylamine to give compounds of formula (XXXI). The reaction can be carried out without solvent or with a solvent such as tetrahydrofuran, ethyl ether, dioxane or methylene chloride, and at a temperature from 20 to 250° C.

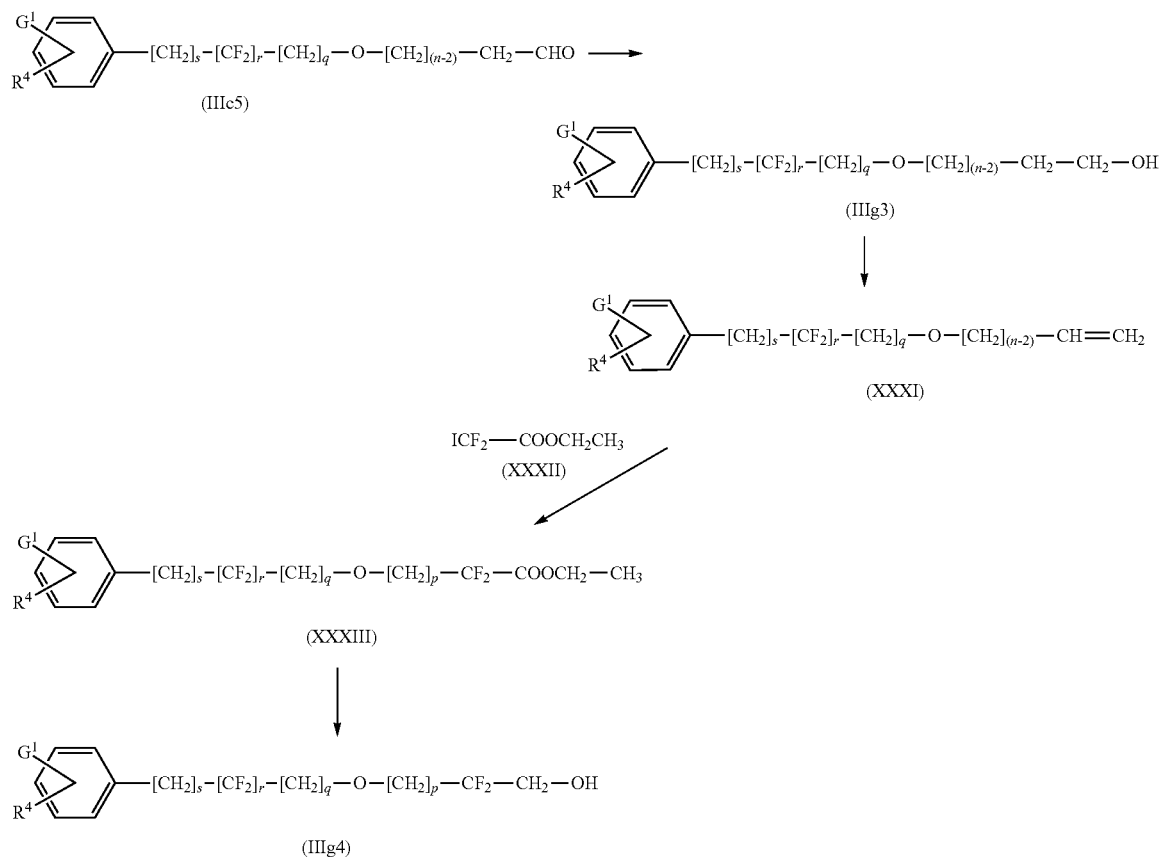

Scheme 5

Compounds of formula (IIIc5) (corresponding to compounds of general formula (III) wherein $G^2$ is a group —CHO and m is 0) can be converted to alcohols (IIIg3) (corresponding to compounds of general formula (III) wherein $G^2$ is a group —$CH_2$—OH, m is 0) by reaction with a hydride such as lithium aluminum hydride, sodium borohydride or diisobutylaluminum hydride in a solvent such as ethyl ether, diisopropyl ether, tetrahydrofuran or methanol, and at a temperature from room temperature to the boiling point of the solvent.

Alkenes of formula (XXXI) can be obtained by reaction of alcohols of formula (IIIg3) (corresponding to compounds of Esters of formula (XXXIII) can be obtained by reaction of alkenes of formula (XXXI) with ethyl iododifluoroacetate in the presence of a metal such as zinc or copper optionally with a catalyst such as nickel chloride hexahydrate and water, in a solvent such as dimethylformamide, tetrahydrofuran, dimethylsulfoxide or dioxane, and a temperature from 20 to 60° C. (see ref. *J. Chem. Soc. Chem. Comm.*, 1992, 233).

The synthesis of alcohols of formula (IIIg4) (corresponding to compounds of general formula (III) wherein $G^2$ is a group —$CH_2$—OH, m is 1 and n is 1) from esters of formula (XXXIII) can be achieved by treatment with a hydride such as lithium aluminum hydride, sodium borohydride or diisobutylaluminum hydride in a solvent such as ethyl ether, diisopropyl ether, tetrahydrofuran or methanol, and at a temperature from room temperature to the boiling point of the solvent.

Scheme 6

In another alternative method the compounds of formula (IIIg6) (corresponding to compounds of general formula (III) wherein $G^1$, $R^4$, s, r, q and m are as hereinabove defined, p is 1 m is 2 and n is 3 may be obtained following the method depicted in Scheme 6.

wherein $G^4$ is a Br atom). The reaction can be carried out with a base such as sodium hydroxide, potassium hydroxide or sodium hydride, optionally in the presence of a base transfer catalyst such as tetrabutylammonium bromide, with a solvent such as water, dimethylformamide, dimethylsulfoxide or diethylene glycol dimethyl ether, and at a temperature from 20° to 100° C.

Aldehydes of formula (IIIc3) can be obtained from alcohols of formula (XXXV) by reaction with chromium trioxide,

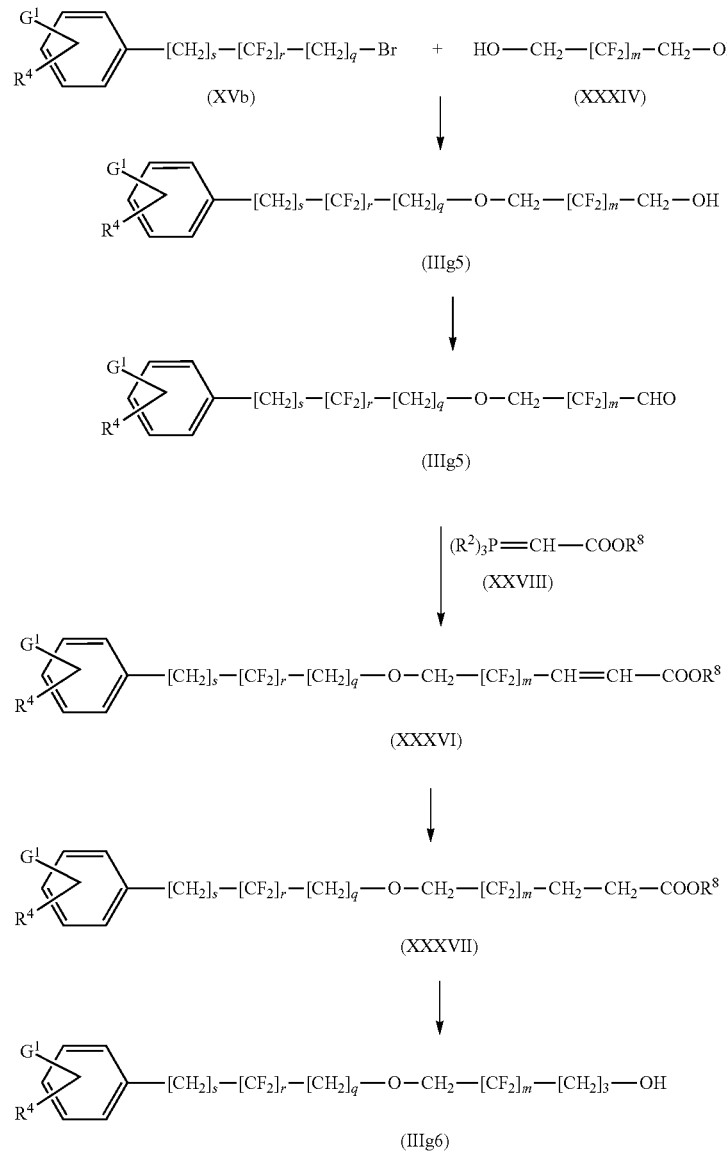

In another alternative method the compounds of formula (IIIg6) (corresponding to compounds of general formula (III) wherein $G^1$, $R^4$, s, r, q and m are as hereinabove defined, p is 1 m is 2 and n is 3 may be obtained following the method depicted in Scheme 6.

Alcohols of formula (IIIg5) (corresponding to compounds of general formula (III) wherein $G^2$ is a group —$CH_2$—OH and p and q are 1) can be obtained by reaction of alcohols of formula (XXXIV) with bromoderivatives of formula (XVg) (corresponding to the compounds of general formula (XV)

manganese dioxide, potassium dichromate, pyridinium chlorochromate, oxalyl chloride in dimethylsulfoxide or Dess-Martin reagent in a solvent such as pyridine, methylene chloride, chloroform, dimethylsulfoxide or acetonitrile, and at a temperature from −78° to 130° C.

Aldehydes of formula (IIIc6) (corresponding to compounds of general formula (III) wherein $G^2$ is a —COH group, p is 1 and n is 1) can react with a phosphorane of formula (XXVIII) wherein $R^8$ represents a $C_{1-4}$ alkyl group and $R^9$ represents a $C_{1-4}$ alkyl or a phenyl group to give esters of formula (XXXVI). The reaction can be carried out in a solvent such as methylene chloride, tetrahydrofuran, ethyl ether or toluene, and at a temperature from room temperature to the boiling point of the solvent.

Hydrogenation of the compounds of formula (XXXVI) gives esters of formula (XXXVII). The reaction can be carried out with a catalyst such as palladium on charcoal or platinum dioxide, in a solvent such as ethanol, methanol, ethyl acetate or dimethylformamide, at a temperature from room temperature to 70° C., and at a pressure from $1.38 \cdot 10^8$ Pa to $2.76 \cdot 10^5$ Pa.

Alcohols of formula (IIIg6) (corresponding to compounds of general formula (III) wherein $G^2$ is a group —CH$_2$—OH, p is 1 and n is 3) can be obtained by treatment of esters of formula (XXXVII) with a hydride such as lithium aluminum hydride, sodium borohydride or diisobutylaluminum hydride in a solvent such as ethyl ether, diisopropyl ether, tetrahydrofuran or methanol, and at a temperature from room temperature to the boiling point of the solvent.

In another alternative method the compounds of formula (III) wherein $G^1$ and $R^4$ are as hereinabove defined, p is 1, r is zero, n is 3, q+s is 3 and $G^2$ is a group —CH$_2$—OH may be obtained following the method depicted in Scheme 7.

manganese dioxide, potassium dichromate, pyridinium chlorochromate, oxalyl chloride in dimethylsulfoxide or Dess-Martin reagent in a solvent such as pyridine, methylene chloride, chloroform, dimethylsulfoxide or acetonitrile, and at a temperature from −78° to 130° C.

Aldehydes of formula (XL) can react with a phosphorane of formula (XXVIII) to give esters of formula (XLI). The reaction can be carried out in a solvent such as methylene chloride, tetrahydrofuran, ethyl ether or toluene, and at a temperature from room temperature to the boiling point of the solvent.

Hydrogenation of the compounds of formula (XLI) gives esters of formula (XLII). The reaction can be carried out with a catalyst such as palladium on charcoal or platinum dioxide, in a solvent such as ethanol, methanol, ethyl acetate or dimethylformamide, at a temperature from room temperature to 70° C., and at a pressure from $1.38 \cdot 10^5$ Pa to $2.76 \cdot 10^5$ Pa.

Alcohols of formula (IIIg7) (corresponding to compounds of general formula (III) wherein $G^2$ is a group —CH$_2$—OH, q+s is 3, r is 0, p is 1 and n is 3) can be obtained by treatment of esters of formula (XLII) with a hydride such as lithium aluminum hydride, sodium borohydride or diisobutylaluminum hydride in a solvent such as ethyl ether, diisopropyl ether, tetrahydrofuran or methanol, and at a temperature from room temperature to the boiling point of the solvent.

Scheme 7

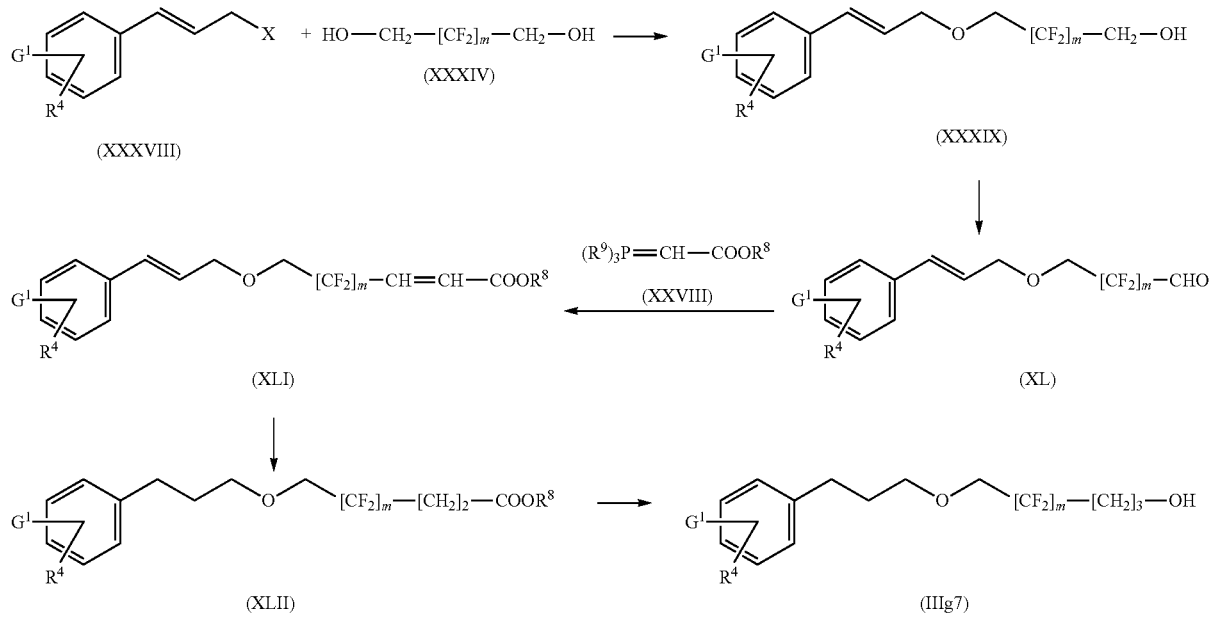

wherein X represents a halogen atom, $R^8$ represents a $C_{1-4}$ alkyl group and $R^9$ represents a $C_{1-4}$ alkyl or a phenyl group.

Alcohols of formula (XXXIX) can be obtained by reaction of alcohols of formula (XXXIV) with haloderivatives of formula (XXXVIII). The reaction can be carried out with a base such as sodium hydroxide, potassium hydroxide or sodium hydride, optionally in the presence of a base transfer catalyst such as tetrabutylammonium bromide, with a solvent such as water, dimethylformamide, dimethylsulfoxide or diethylene glycol dimethyl ether, and at a temperature from 20° to 100° C.

Aldehydes of formula (XL) can be obtained from alcohols of formula (XXXIX) by reaction with chromium trioxide, In another alternative the compounds of formula (IIIa)

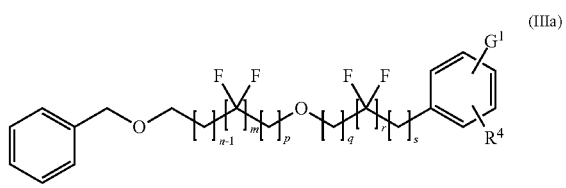

(IIIa)

wherein $G^1$, $R^4$, n, m, p, q, r and s are as hereinabove defined (corresponding to compounds of general formula (III)

wherein G2 is a group —CH$_2$—O-Bz), are obtained starting from compounds of formula (XLIII)

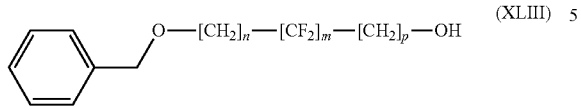

following the method described in Scheme 8 hydride, sodium borohydride or diisobutylaluminum hydride in a solvent such as ethyl ether, diisopropyl ether, tetrahydrofuran or methanol, and at a temperature from room temperature to the boiling point of the solvent.

Alkenes of formula (XLVII) can be obtained by reaction of alcohols of formula (XLVI) with 2-nitrophenyl selenocyanate and tributylphosphine, with a solvent such as tetrahydrofuran, ethyl ether or dioxane, and at a temperature from room temperature to the boiling point of the solvent (see references Hart, D. J.; Kenai, K.-I.; *J. Am. Chem. Soc.* 1993, 105, 1255; Hart, D. J.; *J. Org. Chem* 1981, 46, 3576).

Scheme 8

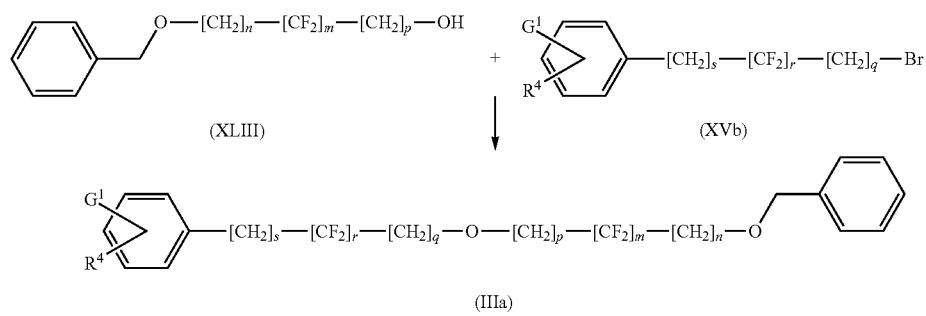

Alcohols of formula (XLIII) can be converted to compounds of formula (IIIa) (corresponding to compounds of general formula (III) wherein G2 is a group —CH$_2$—O-Bz) by reaction with bromoderivatives of formula (XVb) in the presence of a base such as sodium hydroxide, potassium hydroxide or sodium hydride, optionally in the presence of a base transfer catalyst such as tetrabutylammonium bromide, with a solvent such as water, dimethylformamide, dimethylsulfoxide or diethylene glycol dimethyl ether, and at a temperature from 20° to 100° C.

The compounds of formula (XLIII) may be obtained following the synthetic methods of schemes 9 to 10 which are described below:

In one alternative the compounds of formula (XLIIIa) wherein n and m are both 1 may be obtained following the method depicted in Scheme 9.

Alcohols of formula (XLVI) can also react with p-toluensulfonyl chloride or methylsulfonyl chloride, in a solvent such as tetrahydrofuran, ethyl ether, dioxane or methylene chloride, and at a temperature from room temperature to the boiling point of the solvent. The resulting intermediate reacts with a base such as potassium hydroxide, sodium hydroxide, triethylamine or diisopropylethylamine to give compounds of formula (XLVII). The reaction can be carried out without solvent or with a solvent such as tetrahydrofuran, ethyl ether, dioxane or methylene chloride, and at a temperature from 20 to 250° C.

Esters of formula (XLVIII) can be obtained by reaction of alkenes of formula (XLVII) with ethyl iododifluoroacetate (XXXII) in the presence of a metal such as zinc or copper optionally with a catalyst such as nickel chloride hexahydrate and water, in a solvent such as dimethylformamide, tetrahydrofuran, dimethylsulfaxide or dioxane, and a temperature

Scheme 9

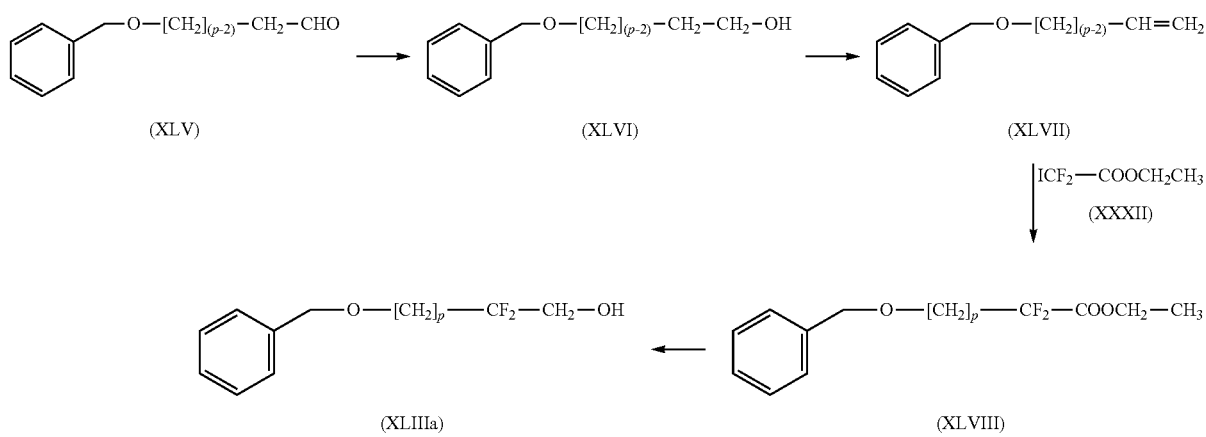

Compounds of formula (XLV) can be converted to alcohols (XLVI) by reaction with a hydride such as lithium aluminum from 20 to 60° C. (see ref. *J. Chem. Soc. Chem. Comm.,* 1992, 233).

The synthesis of alcohols of formula (XLIIIa) from esters of formula (XLVIII) can be achieved by treatment with a hydride such as lithium aluminum hydride, sodium borohydride or diisobutylaluminum hydride in a solvent such as ethyl ether, diisopropyl ether, tetrahydrofuran or methanol, and at a temperature from room temperature to the boiling point of the solvent.

In another alternative method the compounds of formula (XLIIIc) wherein m is as hereinabove defined and $R^5$ represents a $C_{1-4}$ alkyl group or a phenyl group, may be obtained following the method depicted in Scheme 10.

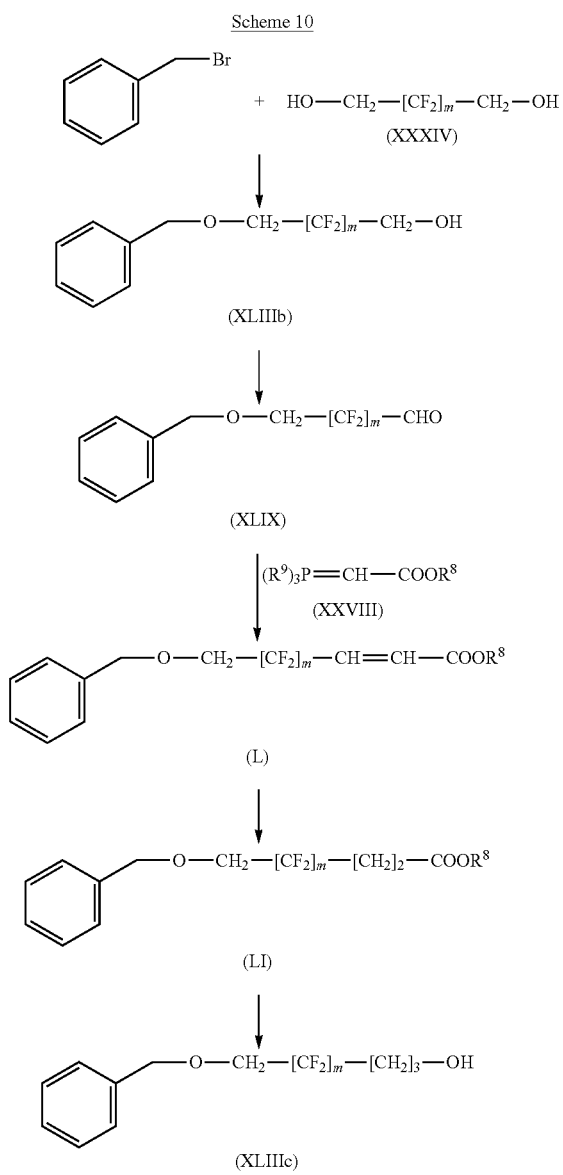

Alcohols of formula (XLIIIb) can be obtained by reaction of alcohols of formula (XXXIV) with benzyl bromide. The reaction can be carried out with a base such as sodium hydroxide, potassium hydroxide or sodium hydride, optionally in the presence of a base transfer catalyst such as tetrabutylammonium bromide, with a solvent such as water, dimethylformamide, dimethylsulfoxide or diethylene glycol dimethyl ether, and at a temperature from 20° to 100° C.

Aldehydes of formula (XLIX) can be obtained from alcohols of formula (XLIIIb) by reaction with chromium trioxide, manganese dioxide, potassium dichromate, pyridinium chlorochromate, oxalyl chloride in dimethylsulfoxide or Dess-Martin reagent in a solvent such as pyridine, methylene chloride, chloroform, dimethylsulfoxide or acetonitrile, and at a temperature from −78° to 130° C.

Aldehydes of formula (XLIX) can react with a phosphorane of formula (XXVIII) to give esters of formula (L). The reaction can be carried out in a solvent such as methylene chloride, tetrahydrofuran, ethyl ether or toluene, and at a temperature from room temperature to the boiling point of the solvent.

Hydrogenation of the compounds of formula (L) gives esters of formula (LI). The reaction can be carried out with a catalyst such as palladium on charcoal or platinum dioxide, in a solvent such as ethanol, methanol, ethyl acetate or dimethylformamide, at a temperature from room temperature to 70° C., and at a pressure from $1.38 \cdot 10^5$ Pa to $2.76 \cdot 10^5$ Pa.

Alcohols of formula (XLIIIc) can be obtained by treatment of esters of formula (LI) with a hydride such as lithium aluminum hydride, sodium borohydride or diisobutylaluminum hydride in a solvent such as ethyl ether, diisopropyl ether, tetrahydrofuran or methanol, and at a temperature from room temperature to the boiling point of the solvent.

The compounds of formula (XV) may be obtained following the synthetic methods of schemes 11 to 13 which are described below:

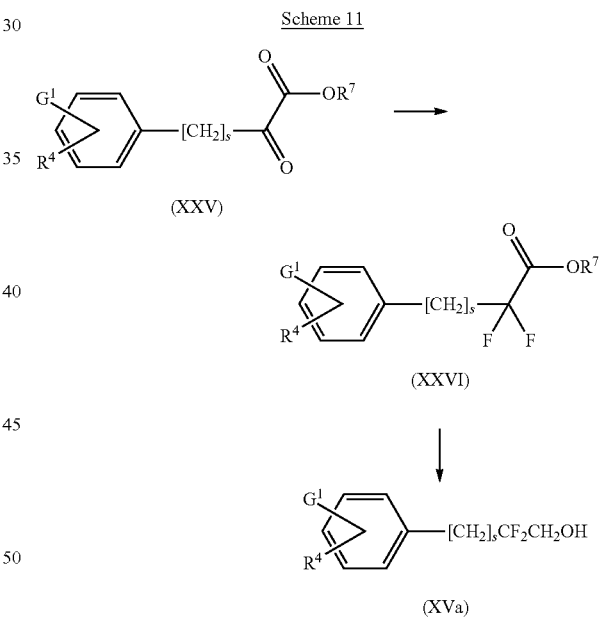

wherein s and $R^4$ are as hereinabove defined, $G^1$ is selected from

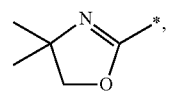

hydrogen or halogen atoms or groups selected from $C_{1-4}$ alkyl, $C_{1-4}$ alkoxy, S—$R^5$, SO—$R^5$ and $SO_2$—$R^5$ wherein $R^5$ is a $C_{1-4}$ alkyl or $C_{3-6}$ cycloalkyl; $R^4$ is selected from hydrogen atom, halogen atoms and $C_{1-4}$ alkyl groups and $R^7$ is a $C_{1-4}$ alkyl group.

Compounds of formula (XXV) can be transformed to compounds of formula (XXVI) by reaction with a fluorinated agent such as (diethylamino) sulfur trifluoride (DAST) or [di(methoxyethyl)amino]sulfur trifluoride, optionally in the presence of a solvent such as methylene chloride, chloroform, methanol, ethanol or tetrahydrofuran, and at a temperature from room temperature to the boiling point of the solvent.

Alcohols of formula (XVa) can be obtained by treatment of esters of formula (XXVI) with a hydride such as lithium aluminum hydride, sodium borohydride or diisobutylaluminum hydride in a solvent such as ethyl ether, diisopropyl ether, tetrahydrofuran or methanol, and at a temperature from room temperature to the boiling point of the solvent.

tetrahydrofuran, dioxane, methylene chloride or dimethylsulfoxide, and at a temperature from −78° C. to 80° C.

Alcohols of formula (XVa3) can be obtained from alkenes of formula (XXVII) by reaction with borane tetrahydrofuran complex or borane-methyl sulfide complex with hydrogen peroxide, in the presence of a base such as sodium hydroxide or potassium hydroxide in a solvent such as tetrahydrofuran, dioxane, water or diethylene glycol dimethyl ether, and at a temperature from −78° C. to 100° C.

Alcohols of formula (XVa3) can be converted to aldehydes of formula (XVc3) by reaction with chromium trioxide, manganese dioxide, potassium dichromate, pyridinium chlorochromate, oxalyl chloride in dimethylsulfoxide or Dess-Mar-

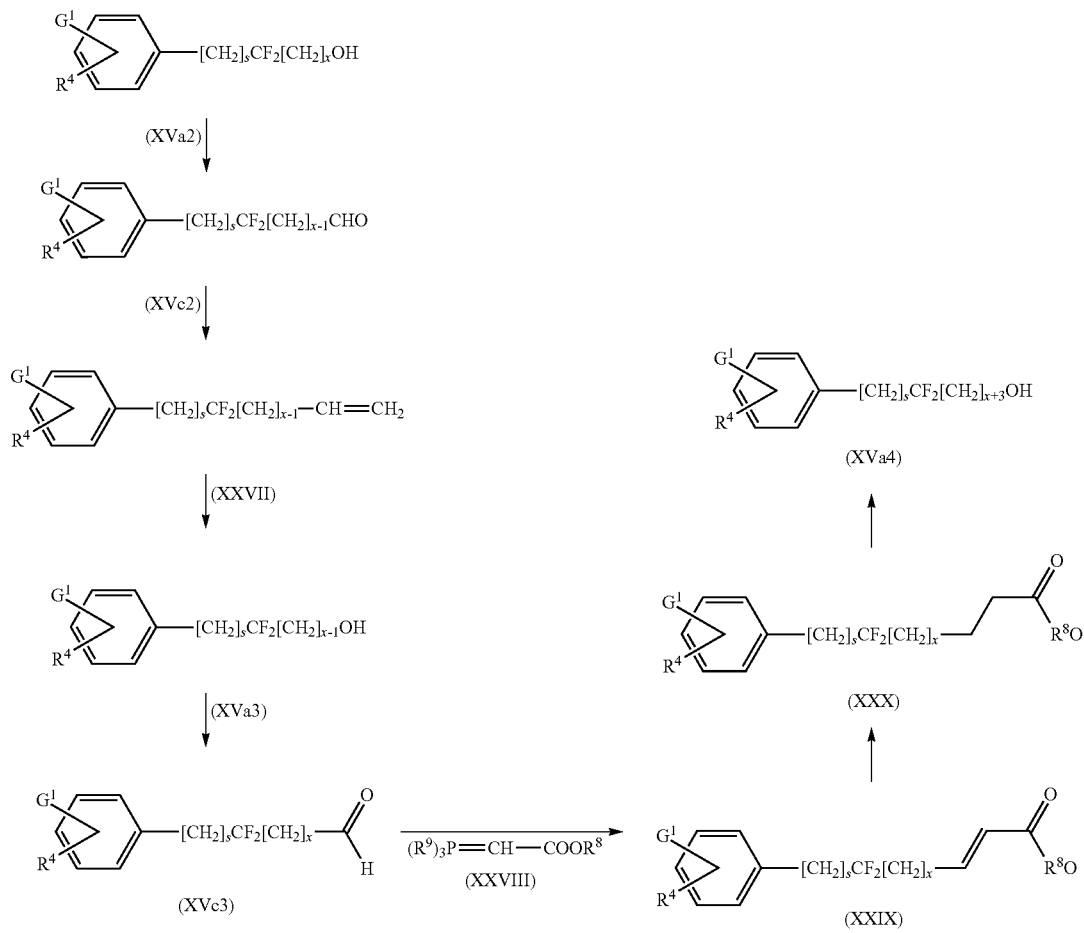

Scheme 12

The alcohols of formula (XVc4) (corresponding to compounds of general formula (XV) wherein x is n-4 and $G^2$ is a group —COH) can be obtained following scheme 12 wherein s, $G^1$ and $R^4$ are as hereinabove defined and x is either an integer from 1 to 3 when the reaction is stopped at product (XVa3) or x is 1 when the scheme is followed until the obtention of product (XVa4).

Alcohols of formula (XVa2) wherein x is at least 1 can be converted to aldehydes of formula (XVc2) by reaction with chromium trioxide, manganese dioxide, potassium dichromate, pyridinium chlorochromate, oxalyl chloride in dimethylsulfoxide or Dess-Martin reagent in a solvent such as pyridine, methylene chloride, chloroform, dimethylsulfoxide or acetonitrile, and at a temperature from −78° to 130° C.

Aldehydes of formula (XVc2) can be transformed to alkenes of formula (XXVII) with Tebbe reagent or methyltriphenylphosphonium bromide in the presence of a base such as sodium hydride or sodium amide with a solvent such as tin reagent in a solvent such as pyridine, methylene chloride, chloroform, dimethylsulfoxide or acetonitrile, and at a temperature from −78° to 130° C.

Aldehydes of formula (XVc3) can react with a phosphorane of formula (XXVIII) wherein $R^8$ is a $C_{1-4}$ alkyl group and $R^9$ is $C_{1-4}$ alkyl or phenyl group to give esters of formula (XXIX). The reaction can be carried out in a solvent such as methylene chloride, tetrahydrofuran, ethyl ether or toluene, and at a temperature from room temperature to the boiling point of the solvent.

Hydrogenation of the compounds of formula (XXIX) gives esters of formula (XXX). The reaction can be carried out with a catalyst such as palladium on charcoal or platinum dioxide, in a solvent such as ethanol, methanol, ethyl acetate or dimethylformamide, at a temperature from room temperature to 70° C., and at a pressure from $1.38 \cdot 10^5$ Pa to $2.76 \cdot 10^5$ Pa.

Alcohols of formula (XVa4) can be obtained by treatment of esters of formula (XXI) with a hydride such as lithium aluminum hydride, sodium borohydride or diisobutylaluminum hydride in a solvent such as ethyl ether, diisopropyl ether, tetrahydrofuran or methanol, and at a temperature from room temperature to the boiling point of the solvent.

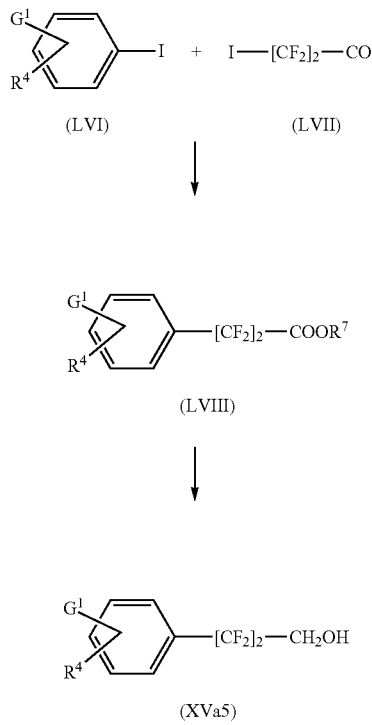

The alcohols of formula (XVa5) wherein s is zero and $G^1$ and $R^4$ are as hereinabove defined may be obtained following scheme 13.

Esters of formula (LVIII) can be obtained by reaction of phenyliodides of formula (LVI) with alkyl iodotetrafluoropropionate (LVII) wherein $R^7$ is a $C_{1-4}$ alkyl group in the presence of copper optionally with a catalyst such as a palladium complex, in a solvent such as dimethylformamide, tetrahydrofuran, dimethylsulfoxide or dioxane, and a temperature from 20 to 60° C. (see ref. Journal of Fluorine Chemistry, 2004, 125 (5), 763-765).

Alcohols of formula (XVa5) can be obtained by treatment of esters of formula (LVIII) with a hydride such as lithium aluminum hydride, sodium borohydride or diisobutylaluminum hydride in a solvent such as ethyl ether, diisopropyl ether, tetrahydrofuran or methanol, and at a temperature from room temperature to the boiling point of the solvent.

The alcohols of formula (XVa6) (corresponding to compounds of general formula (XV) wherein s is 0, r is 1, q is 2, and $G^4$ is a group —OH) and $G^1$ and $R^4$ are as hereinabove defined, can be obtained following scheme 14.

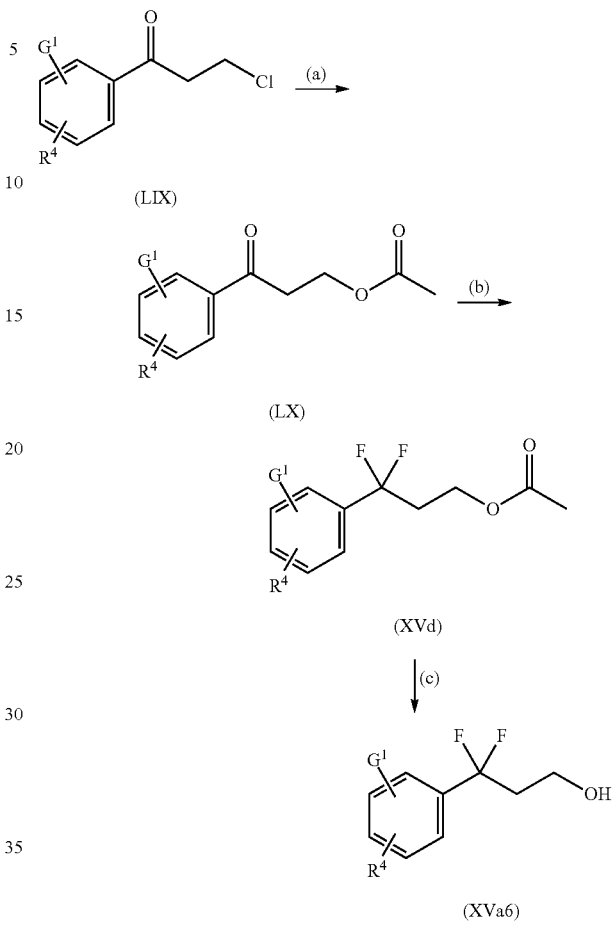

The 3-chloro-1-phenylpropan-1-ones (LIX) are reacted with sodium or potassium acetate and sodium or potassium iodide in a solvent such as glacial acetic acid and a temperature from room temperature to the boiling point of the solvent to yield the compounds of formula (LX).

Subsequent reaction of the compounds of formula (LX) with a fluorinating agent such as (diethylamino) sulfur trifluoride (DAST) or [di(methoxyethyl)amino]sulfur trifluoride (DEOXOFLUOR®), optionally in the presence of a solvent such as methylene chloride, chloroform, methanol, ethanol or tetrahydrofuran, and at a temperature from room temperature to the boiling point of the solvent yields the compounds of formula (XVd).

The hydrolysis of the ester group in the compounds of formula (XVd) in an aqueous solution of sodium hydroxide, potassium hydroxide or sodium carbonate, optionally in the presence of a solvent such as ethanol, methanol or isopropyl alcohol, and at a temperature from room temperature to the boiling point of the solvent, yields the alcohols of formula (XVa6).

The alcohols of formula (XVa7) (corresponding to compounds of general formula (XV) wherein q, r and s have all the value of 1, and $G^4$ is a group —OH) and $G^1$ and $R^4$ are as hereinabove defined, can be obtained following scheme 15.

Scheme 15

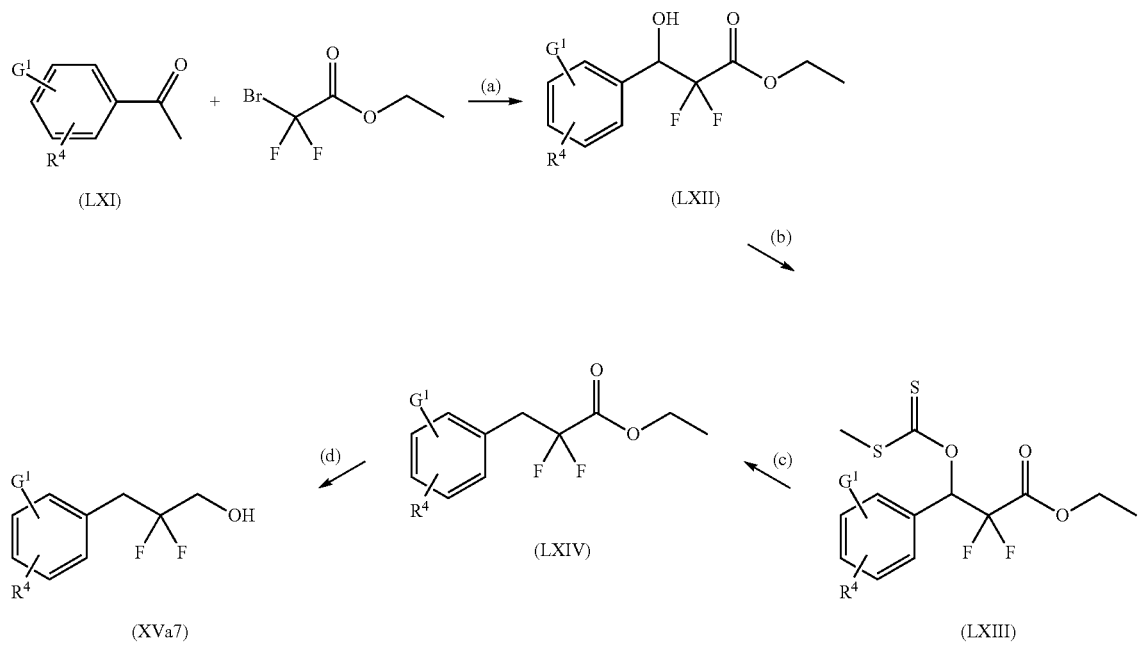

The 1-phenylethanones (LXI) are reacted with bromo(difluoro)acetate in the presence of Zn in a solvent such as tetrahydrofuran, dioxane or ethyl ether and at temperature from room temperature to the boiling point of the solvent.

The resulting compounds (LXII) are then reacted with $CS_2$ in a solvent such as DMSO, DMF, tetrahydrofuran or dioxane and a temperature from room temperature to 60° C. and inert atmosphere to yield a thioacid (not shown) which upon reaction with methyl iodide or dimethylsulfate at room temperature yields the compounds of formula (LXIII).

In a subsequent step the compounds of formula (LXIII) are reacted with a diphenylphosphine oxide and tBuOOtBu (di-tertbutyl peroxide) in a solvent such as tetrahydrofuran, dioxane or ethyl ether and at temperature from room temperature to the boiling point of the solvent to yield the compounds of formula (LXIV).

In a final step the compounds of formula (LXIV) are reacted with a hydride such as lithium aluminum hydride, sodium borohydride or diisobutylaluminum hydride in a solvent such as ethyl ether, diisopropyl ether, tetrahydrofuran or methanol, and at a temperature from room temperature to the boiling point of the solvent to yield the alcohols (XVa7).

Compounds of formula (IIIb) wherein m, n, p, q, r and s are as hereinabove defined, $R^3$ is a hydantoino group and $R^4$=hydrogen atom or $C_{1-4}$ alkyl, can be obtained as shown in Scheme 16.

Scheme 16

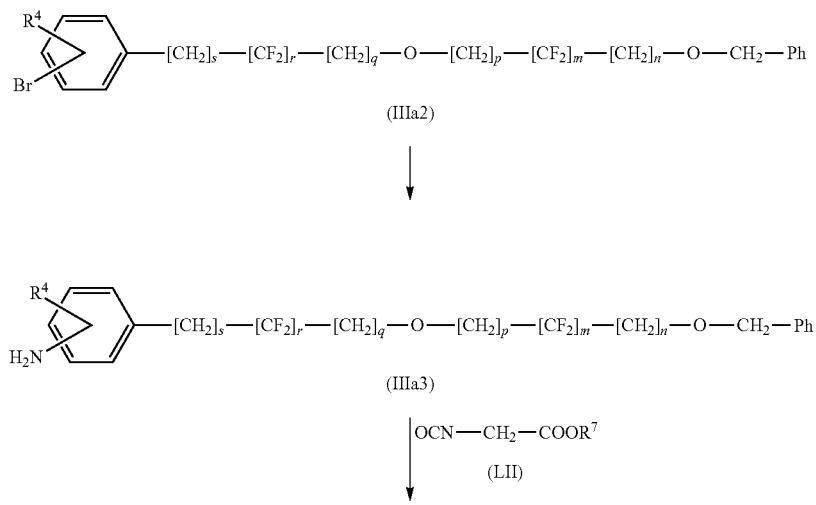

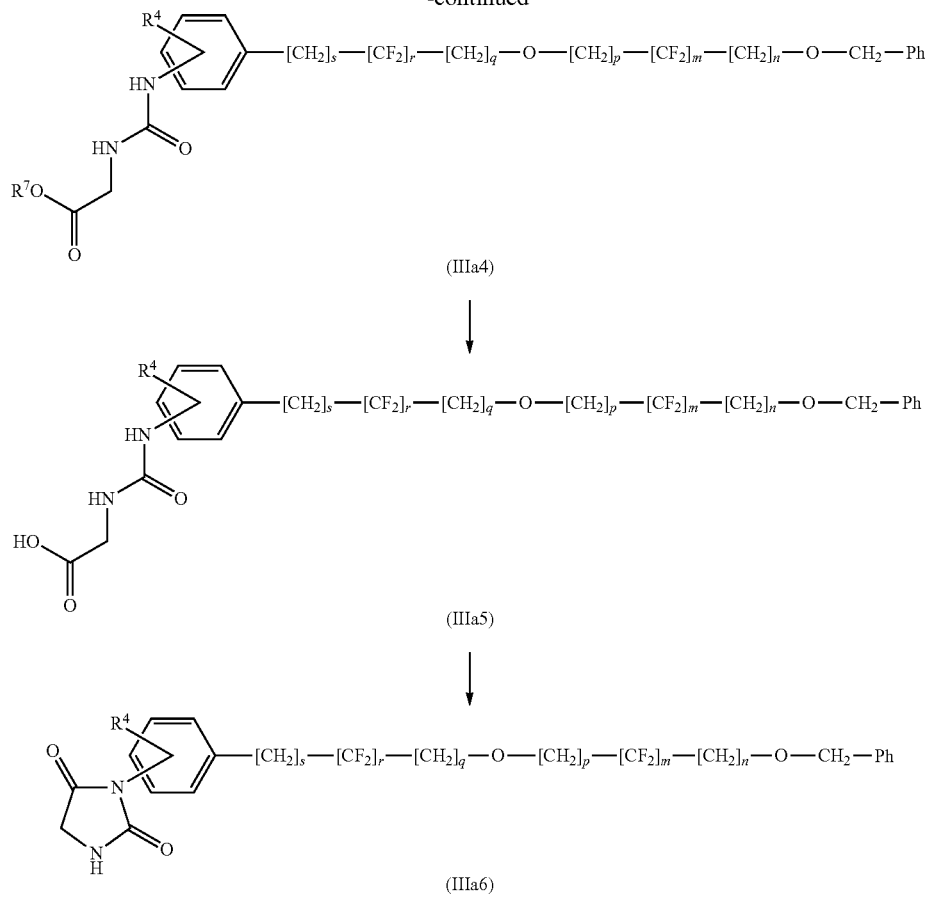

Amines of formula (IIIa3) can be obtained from compounds of formula (IIIa2) by reaction with lithium bis(trimethylsilyl)amide, sodium bis(trimethylsilyl)amide or tert-butyl carbamate. The reaction can be carried out with a base such as sodium ethoxide, potassium carbonate or sodium phenoxide, with a catalytic amount of a phosphine such as ditert-butylphosphine, tri-o-tolylphosphine or triphenylphosphine and a palladium catalyst such as bis(dibenzylideneacetone)palladium or tris(dibenzylideneacetone)-dipalladium (0), with a solvent such as tetrahydrofuran, dioxane, toluene or benzene, and at a temperature from −78° C. to 80° C.

Amines of formula (IIIa3) can be converted to compounds of formula (IIIa4) by reaction with isocyanates of formula (LII) in a solvent such as toluene, benzene or dioxane, and at a temperature from room temperature to the boiling point of the solvent.

Saponification of compounds of formula (IIIa4) gives compounds of formula (IIIa5). The reaction can be carried out with a base such as sodium hydroxide or potassium hydroxide, with a solvent such as methanol, ethanol, water or a mixture of them, and at a temperature from room temperature to the boiling point of the solvent.

Compounds of formula (IIIa6) can be obtained by cyclization of compounds of formula (IIIa5) with an acid such as hydrochloric acid or acetic acid, with a solvent such as methanol, acetic acid, ethanol or water or a mixture of them, and at a temperature from room temperature to the boiling point of the solvent.

Compounds of formula (IIIa6) can be modified to the corresponding alcohol, bromoderivative, mesylate, aldehyde or aminoderivative, following the same pathway shown in Scheme 2.

Compounds wherein $R^4$, m, n, p, q, r and s are as hereinabove defined and $R^3$ is an amido group and $G^2$ is either a —$CH_2$—Br group (IIId) or a benzyloxymethyl (IIIa) can be obtained as shown in Scheme 17.

Scheme 17

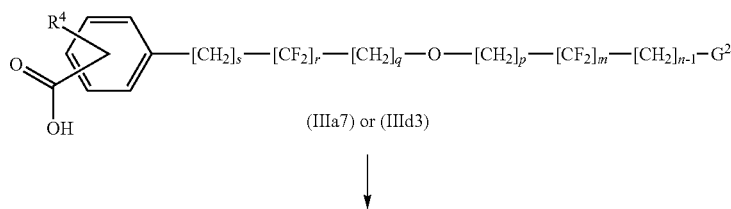

-continued

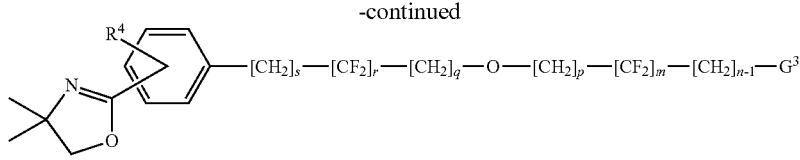

(IIIa8) or (IIId4)

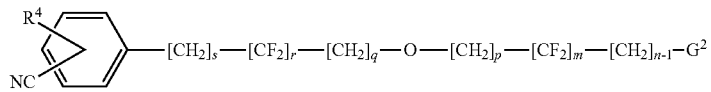

(IIIa9) or (IIId5)

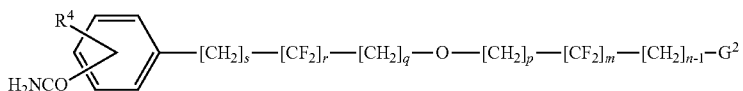

(IIIa10) or (IIId6)

Compounds of formula (IIIa8) or (IIId4) can be obtained from compounds of formula (IIIa7) or (IIId3) by procedures know described in the literature (Meyers A. I., Temple D. L., Haidukewych E. D., *J Org Chem,* 1974, 39(18), 2787; Svenson R. Gronowitz S., *Chem Ser,* 1982, 19, 149; Meyers A. I., Lutomski K. A., *Synthesis,* 1983, 105).

The reaction of compounds of formula (IIIa8) or (IIId4) with phosphorus oxychloride gives nitriles of formula (IIIa9) or (IIId5). The reaction can be carried out in the presence of a base such as pyridines, triethylamine or diisopropylethylamine, with a solvent such as pyridine, benzene or toluene, and at temperature from room temperature to the boiling point of the solvent.

The synthesis of amides of formula (IIIa10) or (IIId6) from nitriles of formula (IIIa9) or (IIId5) can be achieved by reaction with hydrogen in the presence of a catalyst such as Nickel-Raney, palladium on charcoal or platinum dioxide, with a solvent such as methanol, ethanol, isopropyl alcohol or ethyl acetate, at a temperature from room temperature to 60° C., and at a pressure from $1.38 \cdot 10^5$ Pa to $2.76 \cdot 10^5$ Pa.

Nitriles of formula (IIIa9) or (IIId5) can also react with concentrated sulfuric acid to give amides of formula (IIIa10) or (IIId6). The reaction can be carried out without solvent or with a solvent such as methanol, ethanol or isopropyl alcohol, and at a temperature from room temperature to 150° C.

The reaction of nitriles of formula (IIIa9) or (IIId5) with hydrogen peroxide can also afford amides of formula (IIIa10) or (IIId6). The reaction can be carried out in the presence of a base such as sodium hydroxide, potassium hydroxide or potassium carbonate, in a solvent such as methanol, ethanol, isopropyl alcohol, dimethylsulfoxide or acetone, and at a temperature from −20° to 120° C.

Derivatives of formula (IIIa10) can be converted to the corresponding alcohol, mesylate, aldehyde or amino derivative, following the same pathway shown in Scheme 2.

Compounds of formula (I) wherein $R^3$ is an ureic group, $P^1$ is an oxygen protecting group such as benzyl group, $R^4$ is a hydrogen atom or a $C_{1-4}$ alkyl group and $R^1$, $R^2$, n, m, p, q, r, and s are as hereinabove defined, can be obtained as shown in Scheme 18.

Scheme 18

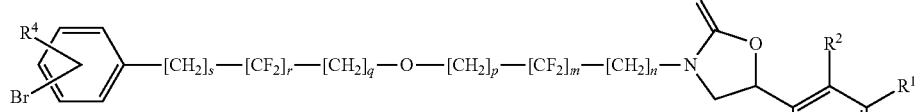

(LIII)

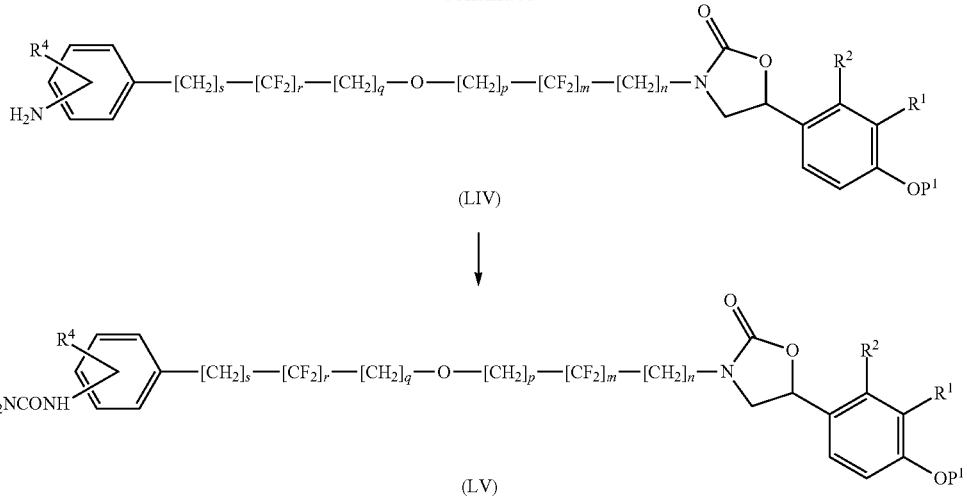

Amines of formula (LIV) can be obtained from compounds of formula (LIII) by reaction with lithium bis(trimethylsilyl)amide, sodium bis(trimethylsilyl)amide or tert-butyl carbamate, with a base such as sodium ethoxide, potassium carbonate or sodium phenoxide, with a catalytic amount of a phosphine such as ditert-butylphosphine, tri-o-tolylphosphine or triphenylphosphine and a palladium catalyst such as bis(dibenzylideneacetone)palladium or tris(dibenzylideneacetone)-dipalladium(0), with a solvent such as tetrahydrofuran, dioxane, toluene or benzene, and at temperature from −78° C. to 80° C.

Amines of formula (LIV) can be converted to ureas of formula (LV) by reaction with potassium cyanate in the presence of an acid such as hydrochloric acid or acetic acid in water, and at a temperature from 0° C. to 100° C.

Compounds of formula (III) wherein $R^3$ is a group $R^5$—SO— or $R^6$—$SO_2$— and $G^2$, $R^4$, n, m, p, q, r, and s are as hereinabove defined, can be obtained as shown in Scheme 19.

Scheme 19

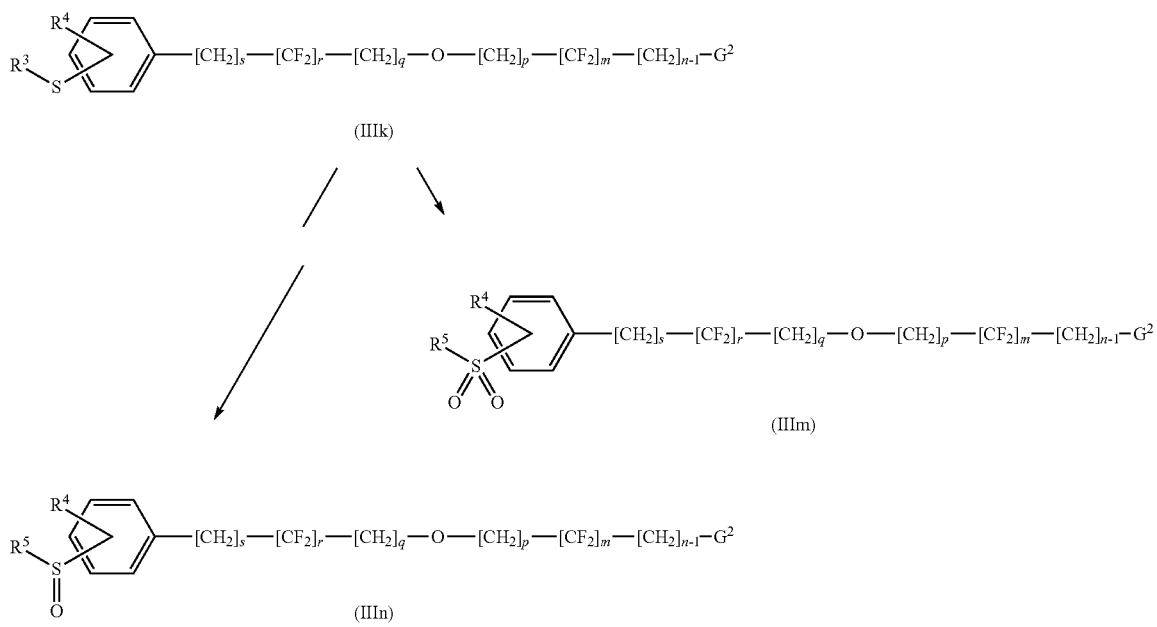

Thioethers of general formula (IIIk) can be converted to sulfoxides of general formula (IIIm) and to sulfones of general formula (IIIn) by reaction with an oxidizing agent such as 3-chloroperoxybenzoic acid, magnesium monoperoxyphthalate or potassium peroxymonosulfate, in a solvent such as acetone, methylene chloride, methanol or ethanol, or a mixture of them, and at a temperature of from 10° C. to 40° C.

Scheme 20

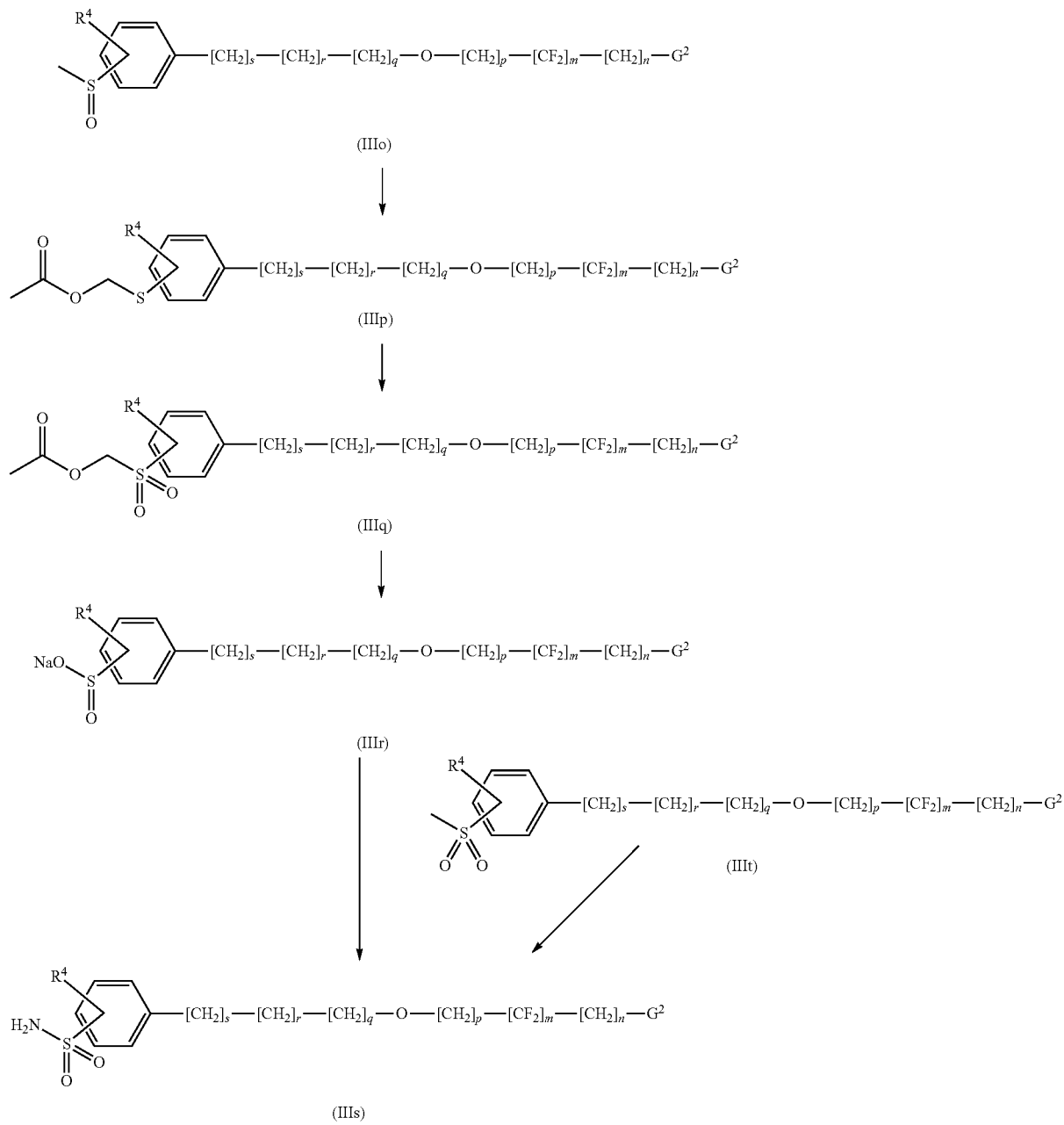

Compounds of formula (III) wherein $R^3$ is a group $R^5R^6$—$NSO_2$— and $G^2$, $R^4$, n, m, p, q, r and s are as hereinabove defined, can be obtained as shown in Scheme 20.

The sulfoxides of formula (IIIo) or (IIIn) and the sulfones of formula (IIIt) or (IIIm) can be converted to sulfonamides of formula (IIIs) only when $R^5$ is a methyl group.

Conversion of sulfoxides of formula (IIIo) into compounds of formula (IIIp) can be carried out with sodium acetate and acetic anhydride, at a temperature from 100° to 160° C.

Oxidation of compounds of formula (IIIp) gives sulfones of formula (IIIq). The reaction can be achieved using an oxidizing agent such as 3-chloroperoxybenzoic acid, magnesium monoperoxyphthalate or potassium peroxymonosulfate, in a solvent such as acetone, methylene chloride, methanol or ethanol, or a mixture of them, and at a temperature of from 10° C. to 40° C.

Sulfones of formula (IIIq) can be converted to compounds of formula (IIIr). The reaction can be carried out with a base such as sodium hydroxide or potassium hydroxide, in a solvent such as tetrahydrofuran, methanol or ethanol, or a mixture of them, and at a temperature from 0° C. to 80° C.

Reaction of compounds of formula (IIIr) with hydroxylamine-o-sulfonic acid gives sulfonamides of formula (IIIs). The process can be carried out in a solvent such as acetic acid or water, in the presence of sodium acetate, and at a temperature from 0° C. to 100° C.

Sulfonamides of formula (IIIs) can also be obtained from sulfones of formula (IIIt). In a first step, sulfones of formula (IIIt) react with a magnesium derivative such as methylmagnesium chloride or ethyl magnesium chloride in the presence of a borane such as triethyl or tributylborane and at room temperature. The final sulfonamide is achieved in a solvent such as acetic acid or water, in the presence of sodium acetate, and at a temperature from 0° C. to 100° C.

EXAMPLES

General. Reagents, starting materials, and solvents were purchased from commercial suppliers and used as received. Concentration refers to evaporation under vacuum using a Büchi rotatory evaporator. Reaction products were purified, when necessary, by flash chromatography on silica gel (40-63 µm) with the solvent system indicated. Spectroscopic data were recorded on a Varian Gemini 300 spectrometer and a Varian Inova 400 spectrometer. Melting points were recorded on a Büchi 535 apparatus.

Intermediate 1. Ethyl 2,2-difluoro-4-phenylbutanoate

To a cooled solution of ethyl 2-oxo-4-phenylbutanoate (1.0 g, 4.85 mmol) in methylene chloride (10 mL) was added DAST (1.6 ml, 12.1 mmol). The mixture was stirred at room temperature overnight. The crude reaction was diluted with methylene chloride (10 mL), washed with saturated solution of sodium bicarbonate (2×10 mL) and water (10 mL), dried ($Na_2SO_4$), and the solvent removed under reduced pressure. The title compound was obtained as brown oil (1.02 g, 91%).

Intermediate 2. 2,2-Difluoro-4-phenylbutan-1-ol

To a cooled solution of intermediate 1 (1.0 g, 4.45 mmol) in tetrahydrofuran (15 mL) was added lithium aluminum hydride (0.22 g, 5.78 mmol). The mixture was stirred at room temperature overnight. To the crude reaction was added water (0.3 mL), 4N sodium hydroxide (0.3 mL) and water (0.9 mL). The resulting solid was filtered through Celite and the solvent removed under reduced pressure. The residue was diluted with methylene chloride (20 mL) and washed with water (10 mL), 2N hydrochloric acid (2×10 mL) and water (10 mL), dried ($Na_2SO_4$), and concentrated. The title compound was obtained as brown oil (0.6 g, 72%).
$^1$H-NMR (300 MHz, $CDCl_3$): 2.10-2.35 (m, 2H); 2.75-2.85 (m, 2H): 3.75 (t, $J_{F-H}$=14.0 Hz, 2H); 7.15-7.25 (m, 3H); 7.25-7.35 (m, 2H).

Intermediate 3. {4-[(6-Bromohexyl)oxy]-3,3-difluorobutyl}benzene

To a solution of Intermediate 2 (0.60 g, 3.22 mmol) in 1,6-dibromohexane (1.74 mL, 11.27 mmol) was added tetrabutylammonium bromide (21 mg, 0.064 mmol) and 50% sodium hydroxide (1.2 mL). The mixture was stirred at room temperature overnight. The crude reaction was diluted with n-hexane (20 mL), washed with water (2×10 mL), dried ($Na_2SO_4$), and the solvent removed under reduced pressure. The title compound was obtained (2.1 g, 52% purity) and was used in the next step without further purification.
$^1$H-NMR (300 MHz, $CDCl_3$): 1.30-1.50 (m, 4H); 1.50-1.65 (m, 2H): 1.70-1.90 (m, 2H); 2.15-2.35 (m, 2H); 2.75-2.90 (m, 2H); 3.35-3.45 (m, 2H); 3.45-3.70 (m, 4H); 7.15-7.25 (m, 3H); 7.25-7.35 (m, 2H).

Intermediate 4. (R,S)-2-{[6-(2,2-Difluoro-4-phenyl-butoxy)hexyl]amino}-1-(2,2-dimethyl-4H-1,3-benzodioxin-6-yl)ethanol To a solution of Intermediate 3 (0.385 g, 0.57 mmol of pure compound) in dimethylformamide (15 mL) was added potassium carbonate (0.31 g, 2.28 mmol) and (R,S)-2-amino-1-(2,2-dimethyl-4H-1,3-benzodioxin-6-yl)ethanol (0.26 g, 1.14 mmol). The mixture was stirred at 80° C. for 66 hours. The crude reaction was filtered and the solvent removed under reduced pressure. The residue was purified by column chromatography with silica gel, eluting with methylene chloride/methanol (from 982 to 95:5), to give (R,S)-2-{[6-(2,2-difluoro-4-phenylbutoxy)hexyl]amino}-1-(2,2-dimethyl-4H-1, 3-benzodioxin-6-yl)ethanol (0.2 g, 71%) as brown oil.
MS (M+): 491

Example 1

(R,S)-4-(2-{[6-(2,2-Difluoro-4-phenylbutoxy)hexyl] amino}-1-hydroxy-ethyl)-2-(hydroxymethyl)phenol

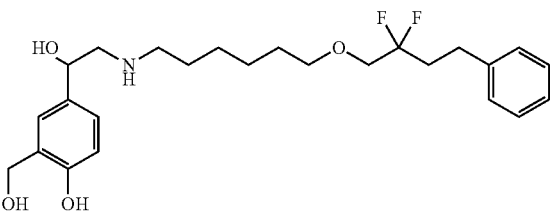

A solution of Intermediate 4 (0.20 g, 0.4 mmol) in a mixture of acetic acid (10 mL) and water (2 mL) was heated at 70° C. for 3 hours. The solvent was removed under reduced pressure. The resulting oil was purified by column chromatography with silica gel, eluting with methylene chloride/methanol/ammonium hydroxide (80:15:1.5) to give (R,S)-4-(2-{[6-(2,2-difluoro-4-phenylbutoxy)hexyl]amino}-1-hydroxy-ethyl)-2-(hydroxymethyl)phenol (104 mg, 57%) as oil.
$^1$H-NMR (400 MHz, dimethylsulfoxide-D6), 1.25-1.31 (m, 4H); 1.34-1.41 (m, 2H): 1.47-1.54 (m, 2H); 2.12-2.25 (m, 2H); 2.54-2.57 (m, 4H); 2.71-2.75 (m, 2H); 3.47 (t, J=6.4 Hz, 2H); 3.66 (t, $J_{F-H}$=13.3 Hz, 2H); 4.45-4.50 (m, 4H); 4.90-4.92 (m, 1H); 4.99 (bs, 1H); 6.68 (d, J=8.3 Hz, 1H); 6.97 (dd, $J_1$=8.3 Hz, $J_2$=2.1 Hz, 1H); 7.17-7.31 (m, 6H); 9.14 (bs, 1H).
MS (M+): 451.

Intermediate 6. Ethyl difluoro(phenyl)acetate

Obtained from ethyl(phenyl)(oxo)acetate (7.5 mL, 47 mmol) by the procedure described in Intermediate 1. Purification by column chromatography with silica gel and n-hexane/ethyl acetate (from pure n-hexane to 10:1) as eluent gave the title compound (13.2 g, 70%) as oil.
$^1$H-NMR (300 MHz, $CDCl_3$): 1.30 (t, J=7.1 Hz, 3H); 4.3 (q, J=7.1 Hz, 2H); 7.43-7.51 (m, 3H); 7.61-7.63 (m, 2H).

Intermediate 6. 2,2-Difluoro-2-phenylethanol

Obtained from Intermediate 5 (13.2 g, 66 mmol) by the procedure described in Intermediate 2. The title compound was obtained (6.88 g, 66%) as oil.
$^1$H-NMR (300 MHz, $CDCl_3$): 4.00 (t, $J_{F-H}$=13.5 Hz, 2H); 7.45-7.48 (m, 3H); 7.50-7.54 (m, 2H), Intermediate 7. {2-[(6-Bromohexyl)oxy]-1,1-difluoroethyl}benzene Obtained from Intermediate 6 (6.88 g, 43.5 mmol) by the procedure described in Intermediate 3. Purification by column chromatography with silica gel and n-hexane/ethyl acetate (10:1) as eluent gave the title compound (10.9 g, 78%) as oil.

$^1$H-NMR (300 MHz, CDCl$_3$):1.40-1.60 (m, 2H); 1.78-1.90 (m, 4H); 3.36-3.44 (m, 4H); 3.52 (t, J=6.5 Hz, 2H); 3.84 (t, J$_{F-H}$=13.2 Hz, 2H); 7.43-7.46 (m, 3H); 7.50-7.54 (m, 2H).

Intermediate 8. 2-[6-(2,2-Difluoro-2-phenylethoxy)hexyl]-1H-isoindole-1,3(2H)-dione To a solution of Intermediate 7 (10.9 g, 34 mmol) in dimethylformamide (23 mL) was added potassium phthalimide (7.56 g, 40.8 mmol) and a catalytic amount of (n-hexadecyl)tri-n-butylphosphonium bromide. The mixture was heated at 70° C. for 3 hours. The solvent was removed under reduced pressure. Purification by column chromatography with silica gel, eluting with methylene chloride yielded the title compound (6.41 g, 49%) as oil.

$^1$H-NMR (300 MHz, CDCl$_3$): 1.28-1.33 (m, 4H); 1.51-1.56 (m, 2H); 1.62-1.66 (m, 2H); 3.50 (t, J=6.5 Hz, 2H); 3.63-3.68 (m, 2H); 3.82 (t, J$_{F-H}$=13.2 Hz, 2H); 7.42-7.44 (m, 3H); 7.49-7.52 (m, 2H); 7.69-7.72 (m, 2H); 7.83-7.86 (m, 2H).

Intermediate 9. [6-(2,2-Difluoro-2-phenylethoxy)hexyl]amine

To a solution of Intermediate 8 (6.41 g, 16.5 mmol) in ethanol (50 ml) was added hydrazine monohydrate (12 mL, 247 mmol). The mixture was stirred at room temperature overnight, concentrated, and the residue was triturated with isopropyl alcohol. The resulting solid was filtered and the solvent removed under reduced pressure. The residue was purified by column chromatography with silica gel, eluting with methylene chloride/ethanol/ammonium hydroxide (80:8:1) to give the title compound (2.31 g, 54%) as oil.

$^1$H-NMR (300 MHz, CDCl$_3$): 1.27-1.32 (m, 4H); 1.39-1.44 (m, 2H); 1.53-1.58 (m, 2H); 2.66 (t, J=6.9 Hz, 2H); 3.52 (t, J=6.5 Hz, 2H); 3.84 (t, J$_{F-H}$=13.2 Hz, 2H); 7.43-7.46 (m, 3H); 7.51-7.54 (m, 2H).

Intermediate 10. (R,S)-1-[4-(Benzyloxy)-3-(hydroxymethyl)phenyl]-2-{[6-(2,2-difluoro-2-phenylethoxy)hexyl]amino}ethanol A solution of Intermediate 9 (0.71 g, 2.77 mmol) and 4-(benzyloxy)-3-(hydroxymethyl)phenyl](oxo)acetaldehyde (0.75 g, 2.77 mmol) in tetrahydrofuran (8 mL) and methanol (8 mL) was stirred at room temperature for 1 hour. The solution was cooled to 0° C. and sodium borohydride (0.25 g, 6.65 mmol) was slowly added. The reaction mixture was stirred at room temperature for 2.5 hours. Water was added (2 mL) and the solvent removed under reduced pressure. The residue was treated with methylene chloride (20 mL) and water. The organic layer was washed with water (2×10 mL), saturated solution of sodium bicarbonate (2×10 mL) and brine (10 mL), dried (Na$_2$SO$_4$) and the solvent removed under reduced pressure. (R,S)-1-[4-(Benzyloxy)-3-(hydroxymethyl)phenyl)-2-{[6-(2,2-difluoro-2-phenylethoxy)hexyl]amino}ethanol was obtained (1.43 g, 100%) as oil.

$^1$H-NMR (300 MHz, CDCl$_3$): 1.25-1.35 (m, 4H); 1.40-1.60 (m, 5H); 2.57-2.64 (m, 3H); 2.82-2.84 (m, 1H); 3.53 (d, J=5.2 Hz, 2H); 3.79-3.88 (m, 2H); 4.60-4.70 (m, 1H); 4.73 (s, 2H); 5.12 (s, 2H); 5.30-5.32 (m, 1H); 6.92 (d, J=8.2 Hz, 1H); 7.26-7.50 (m, 10H).

Example 2

(R,S)-4-(2-{[6-(2,2-Difluoro-2-phenylethoxy)hexyl]amino}-1-hydroxy-ethyl)-2-(hydroxymethyl)phenol

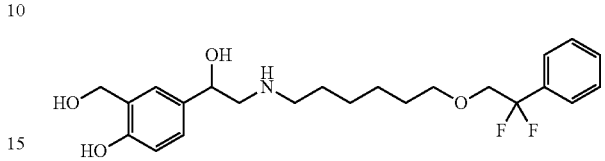

To a solution of Intermediate 10 (1.43 g, 2.78 mmol) in methanol (100 mL) was added palladium on charcoal (150 mg). The mixture was hydrogenated at 20 psi for 6 hours. The catalyst was filtered through Celite and the solvent removed under reduced pressure. The resulting oil was purified by column chromatography eluting with methylene chloride/ethanol/ammonium hydroxide (40:8:1) to give (R,S)-4-(2-{[6-(2,2-difluoro-2-phenylethoxy)hexyl]amino}-hydroxy-ethyl)-2-(hydroxymethyl)phenol (0.75 g, 64%) as oil.

$^1$H-NMR (400 MHz, Cl$_3$CD): 1.25-1.33 (m, 4H); 1.41-1.47 (m, 2H); 1.50-1.56 (m, 2H); 2.51-2.74 (m, 4H); 3.51 (t, J=6.7 Hz, 2H); 3.79 (bs, 4H); 3.84 (t, J$_{F-H}$=13.1 Hz, 2H); 4.54 (dd, J$_1$=8.8 Hz, J$_2$=3.7 Hz, 1H); 4.72 (s, 2H); 6.77 (d, J=8.2 Hz, 1H); 6.93 (s, 1H); 7.08 (dd, J$_1$=8.2 Hz, J$_2$=2.0 Hz, 1H); 7.42-7.44 (m, 3H); 7.50-7.52 (m, 2H).

MS (M+): 423.

Intermediate 11. [4-(Allyloxy)butyl]benzene

To a solution of 4-phenylbutan-1-ol (0.60 g, 3.99 mmol) in 1,3-dibromopropane (2.14 mL, 10.60 mmol) was added tetrabutylammonium bromide (20 mg, 0.064 mmol) and 50% sodium hydroxide (1.5 mL). The mixture was stirred at room temperature overnight. The crude reaction was diluted with n-hexane (20 mL) and washed with water (2×10 mL), dried (Na$_2$SO$_4$), and the solvent removed under reduced pressure. The title compound (1.90 g, 92% purity) was obtained by distillation of the residue under reduced pressure and was used in the next step without further purification.

$^1$H-NMR (300 MHz, CDCl$_3$): 1.50-1.80 (m, 4H); 2.50-2.70 (m, 2H); 3.35-3.45 (m, 2H); 3.90-4.00 (m, 2H); 5.10-5.35 (m, 2H); 5.80-6.00 (m, 1H); 7.15-7.20 (m, 3H); 7.20-7.35 (m, 2H).

Intermediate 12. 3-(4-Phenylbutoxy)propan-1-ol

A solution of Intermediate 11 (0.40 g, 2.10 mmol) in THF (5 mL) was cooled to 0° C. A 0.5 M solution of BBN (5 mL, 2.52 mmol) in THF was added, and the resulting mixture was stirred 1 hour at 0° C. and 2 hours at room temperature. A solution of 2M NaOH (1 mL) and hydrogen peroxide (1 mL, 35%) was successively added and the mixture stirred 1 hour at room temperature. The solution was then concentrated and the residue dissolved in ether (25 mL), washed with water (2×15 mL) and brine (5 mL), dried (Na$_2$SO$_4$) and the solvent removed under reduced pressure. Purification of the residue by column chromatography on silica gel (hexane/AcOEt, 6:1) afforded the title compound (0.24 g, 55%) as oil.

$^1$H-NMR (300 MHz, CDCl$_3$): 1.50-1.75 (m, 4H); 1.75-1.90 (m, 2H); 2.55-2.70 (m, 2H); 3.35-3.50 (m, 2H); 3.60 (t, J=6.0 Hz, 2H); 3.70-3.85 (m, 2H); 7.15-7.20 (m, 3H); 7.20-7.35 (m, 2H).

Intermediate 13.
3-(4-Phenylbutoxy)propionaldehyde

To a solution of Intermediate 12 (1.0 g, 4.8 mmol) in $CH_2Cl_2$ (20 mL) was added Dess-Martin periodinane (2.4 g, 5.76 mmol) and the reaction was stirred 2 hours at room temperature. The solution was then diluted with $CH_2Cl_2$ (40 mL), washed with water (2×20 mL), saturated solution of sodium bicarbonate (2×20 mL), and water (20 mL), dried ($Na_2SO_4$), and concentrated. The residue was purified by column chromatography (methylene chloride/acetone, 20:1) to afford the title compound (550 mg, 58%) as oil.

$^1$H-NMR (300 MHz, $CDCl_3$): 1.50-1.75 (m, 4H); 2.55-2.75 (m, 4H); 3.35-3.50 (m, 2H); 3.70-3.80 (m, 2H); 7.15-7.20 (m, 3H); 7.20-7.35 (m, 2H); 9.80 (bs, 1H).

Intermediate 14. 1-(4-Phenylbutoxy)hept-6-en-3-ol

A solution of Intermediate 13 (0.55 g, 2.66 mmol) in THF (5 mL) was cooled to –30° C. To this solution a 0.5 M solution of 3-butenylmagnesium bromide (5.8 mL, 2.92 mmol) in THF was added, and the resulting mixture was stirred 2 hours at –30° C. The reaction was allowed to reach room temperature; acetic acid (0.1 mL) was added and concentrated. Purification by column chromatography with silica gel and methylene chloride/acetone (20:1) as eluent afforded the title compound (410 mg, 54%) as oil.

$^1$H-NMR (300 MHz, $CDCl_3$): 1.40-1.80 (m, 8H); 2.00-2.15 (m, 2H); 2.55-2.70 (m, 2H); 3.15-3.25 (bs, 1H); 3.35-3.50 (m, 2H); 3.75-3.85 (m, 1H); 4.90-5.10 (m, 2H); 5.75-2.95 (m, 1H); 7.15-7.20 (m, 3H); 7.20-7.35 (m, 2H).

Intermediate 15. 1-(4-Phenylbutoxy)hept-6-en-3-one

Obtained from Intermediate 14 (0.41 g, 1.56 mmol) by the procedure described for the Intermediate 13. Purification by column chromatography with silica gel and methylene chloride/acetone (20:1) as eluent gave the title compound (0.36 g, 88%) as oil.

Intermediate 16. {4-[(3,3-Difluorohept-6-en-1-yl)oxy]butyl}benzene

To a cooled solution of Intermediate 15 (0.36 g, 1.36 mmol) in methylene chloride (1 mL) was added DAST (0.8 ml, 6.0 mmol). The mixture was stirred at room temperature overnight. The crude reaction was diluted with methylene chloride (10 mL), washed with saturated solution of sodium bicarbonate (2×5 mL) and water (5 mL), dried ($Na_2SO_4$), and the solvent removed under reduced pressure. The residue was purified by column chromatography on silica gel using methylene chloride/acetone (20:1) as eluent. The title compound was obtained (110 mg, 27%) as brown oil.

Intermediate 17.
4,4-Difluoro-6-(4-phenylbutoxy)hexanal

Intermediate 16 (110 mg, 0.39 mmol) was dissolved in a mixture of THF (3 mL) and water (1 mL). To this solution was added sodium metaperiodate (272 mg, 1.27 mmol) and osmium tetroxide (4% water solution, 0.15 ml). The suspension was stirred 12 hours at room temperature, filtered and concentrated. The residue was purified by column chromatography on silica gel using methylene chloride/acetone (10:1) as eluent, to afford the title compound (89 mg, 81%) as oil.

$^1$H-NMR (300 MHz, $CDCl_3$): 1.50-1.75 (m, 4H); 2.00-2.30 (m, 4H); 2.55-2.70 (m, 4H); 3.40 (t, J=6.0 Hz, 2H); 3.55 (t, J=9.0 Hz, 2H); 7.15-7.20 (m, 3H); 7.20-7.35 (m, 2H); 9.80 (bs, 1H).

Intermediate 18. (R,S)-2-{[4,4-Difluoro-6-(4-phenylbutoxy)hexyl]amino}-1-(2,2-dimethyl-4H-1,3-benzodioxin-8-yl)ethanol To a solution of intermediate 17 (60 mg, 0.28 mmol) in MeOH (5 mL) was added acetic acid (0.1 molecular sieves (150 mg) and (R,S)-2-amino-1-(2,2-dimethyl-4H-1,3-benzodioxin-6-yl)ethanol (125 mg, 0.56 mmol). The mixture was stirred 12 hours at room temperature, then sodium cyanoborohydride (21 mg, 0.33 mmol) was added, and the mixture was further stirred for 1 hour. The mixture was filtered and concentrated. The residue was dissolved in methylene chloride (10 mL) and washed with brine (3×2 mL), water (2×2 mL), dried ($Na_2SO_4$), and concentrated. The residue (200 mg) was used without further purification in the next step.

MS (M+): 491

Example 3

(R,S)-4-(2-{[4,4-Difluoro-6-(4-phenylbutoxy)hexyl]amino}-1-hydroxy-ethyl)-2-(hydroxymethyl)phenol

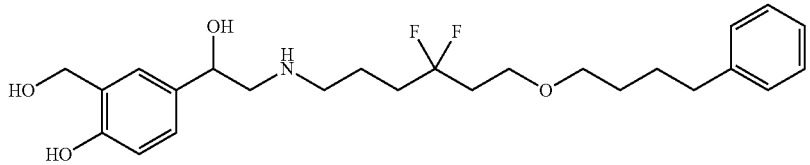

Obtained from Intermediate 18 (0.20 g, 0.4 mmol) by the procedure described in Example 1. Purification by column chromatography with silica gel, eluting with methylene chloride/methanol/ammonium hydroxide (80:15:1.5) gave (R,S)-4-(2-{[4,4-difluoro-6-(4-phenylbutoxy)hexyl]amino}-1-hydroxy-ethyl)-2-(hydroxymethyl)phenol (69 mg, 38%) as oil.

$^1$H-NMR (400 MHz, dimethylsulfoxide-D6), 1.26-1.31 (m, 4H); 1.35-1.41 (m, 2H); 1.46-1.55 (m, 2H); 2.12-2.25 (m, 2H); 2.54-2.58 (m, 4H); 2.71-2.75 (m, 2H); 3.47 (d, J=6.4 Hz, 2H); 3.65 (t, $J_{F-H}$=13.5 Hz, 2H); 4.45-4.50 (m, 4H); 4.91 (bs, 1H); 5.00 (bs, 1H); 6.7 (d, J=8.3 Hz, 1H); 6.97 (dd, $J_1$=7.9 Hz, $J_2$=1.7 Hz, 1H); 7.19-7.31 (m, 6H); 9.17 (bs, 1H).

MS (M+): 452.

Intermediate 19. Difluoro(phenyl)acetaldehyde

Obtained from Intermediate 6 (1.0 g, 6.3 mmol) by the procedure described for the Intermediate 13. The title compound was obtained (0.88 g, 86%) as oil.

Intermediate 20. Ethyl (2E)-4,4-difluoro-4-phenylbut-2-enoate

Intermediate 19 (0.88 g, 5.64 mmol) was dissolved in THF (12 mL) and (carbethoxymethylene)triphenylphosphorane (1.96 g, 5.64 mmol) was then added. The solution was stirred at 50° C. for 12 hours. The mixture was concentrated and the residue was purified by column chromatography on silica gel using n-hexane/AcOEt (5:1) as eluent. The title compound was obtained (1.10 g, 89%) as pale yellow oil.

$^1$H-NMR (300 MHz, CDCl$_3$): 1.45 (t, J=7.1 Hz, 3H); 4.45 (q, J=7.1 Hz, 2H); 6.45 (d, J$_{F-H}$=18 Hz, 1H); 7.15-7.30 (m, 1H); 7.60-7.70 (m, 3H); 7.70-7.75 (m, 2H).

Intermediate 21, Ethyl 4,4-difluoro-4-phenylbutanoate

A solution of Intermediate 20 (1 g, 4.42 mmol) in methanol (20 mL) was hydrogenated in the presence of palladium on charcoal (10 mg, 10%) for 3 hours. The mixture was then filtered over Celite and the solvent removed under reduced pressure. The residue (0.91 g) was used in the next step without further purification.

Intermediate 22. 4,4-Difluoro-4-phenylbutan-1-ol

Obtained from intermediate 21 (0.9 g, 4.1 mmol) by the procedure described in Intermediate 2. The title compound was obtained as oil (0.65 g, 85%).

$^1$H-NMR (300 MHz, CDCl$_3$): 1.50-1.75 (m, 2H); 2.10-2.30 (m, 2H); 3.55-3.65 (m, 2H); 7.15-7.45 (m, 5H).

Intermediate. 23. {4-[(6-Bromohexyl)oxy]-1,1-difluorobutyl}benzene

Obtained from Intermediate 22 (0.6 g, 3.22 mmol) by the procedure described in Intermediate 3. The title compound was obtained (1.98 g, 63% purity) as oil.

Intermediate 24. (R,S)-2-{[6-(4,4-Difluoro-4-phenyl-butoxy)hexyl]amino}-1-(2,2-dimethyl-4H-1,3-benzodioxin-6-yl)ethanol Obtained from Intermediate 23 (0.4 g, 0.6 mmol) by the procedure described in Intermediate 4. The title compound was obtained (0.21 g, 70%) as oil.
MS (M+): 491

Example 4

(R,S)-4-(2-{[6-(4,4-Difluoro-4-phenylbutoxy)hexyl]amino}-1-hydroxy-ethyl)-2-(hydroxymethyl)phenol

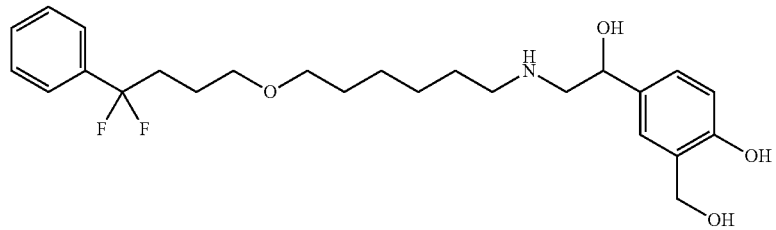

Obtained from Intermediate 24 (0.2 g, 0.4 mmol) by the procedure described in Example 1. The title compound was obtained (98 mg, 51%) as oil.

$^1$H-NMR (400 MHz, dimethylsulfoxide-D6); 1.25-1.31 (m, 4H); 1.34-1.41 (m, 2H); 1.47-1.54 (m, 2H); 2.12-2.25 (m, 2H); 2.54-2.57 (m, 4H); 2.71-2.75 (m, 2H); 3.47 (t, J=6.4 Hz, 2H); 3.66 (t, J$_{F-H}$=13.3 Hz, 2H); 4.45-4.50 (m, 4H); 4.90-4.92 (m, 1H); 4.99 (bs, 1H); 6.68 (d, J=8.3 Hz, 1H); 6.97 (dd, J$_1$=8.3 Hz, J$_2$2.1 Hz, 1H); 7.17-7.31 (m, 6H); 9.14 (bs, 1H).
MS (M+): 451

Intermediate 25. (R,S)-8-(Benzyloxy)-5-(1-{[tert-butyl(dimethyl)silyl]oxy}-2-{[6-(2,2-difluoro-2-phenylethoxy)hexyl]amino}ethyl)quinolin-2(1H)-one To a solution of (R,S)-8-(benzyloxy)-5-(2-bromo-1-{[tert-butyl(dimethyl)silyl]oxy}ethyl)quinolin-2(1H)-one (1.58 g, 3.25 mmol) and Intermediate 9 (1.0 g, 3.9 mmol) in dimethylsulfoxide (4.5 mL) was added sodium bicarbonate (0.82 g, 9.7 mmol) and sodium iodide (0.73 m, 4.87 mmol). The mixture was heated at 140° C. for 2 hours. After cooling, the reaction was diluted with water (20 mL) and extracted with diethyl ether (2×10 mL). The combined organic extracts were washed with water (2×5 mL) and brine (10 mL), dried (Na$_2$SO$_4$), and the solvent removed under reduced pressure. The title compound was obtained (2.14 g, 99%) as oil.
MS (M+): 664

Intermediate 26. (R,S)-8-(Benzyloxy)-5-(2-{[6-(2,2-difluoro-2-phenylethoxy)hexyl]-amino}-1-hydroxy-ethyl)quinolin-2(1H)-one To a solution of Intermediate 25 (2.14 g, 3.21 mmol) in tetrahydrofuran (20 mL) was added tetra-n-butyl ammonium fluoride (1.68 g, 6.42 mmol). The mixture was stirred at room temperature overnight. The solvent was removed under reduced pressure. Purification by column chromatography using methylene chloride/methanol (from 95:5 to 85:15) as eluent gave (R,S)-8-(benzyloxy)-5-(2-{[6-(2,2-difluoro-2-phenylethoxy)hexyl]-amino}-1-hydroxyethyl)quinolin-2(1H)-one (1.27 g, 72%) as oil.
MS (m+): 550

Example 5

(R,S)-5-(2-{[6-(2,2-Difluoro-2-phenylethoxy)hexyl]amino}-1-hydroxy-ethyl)-8-hydroxyquinolin-2(1H)-one

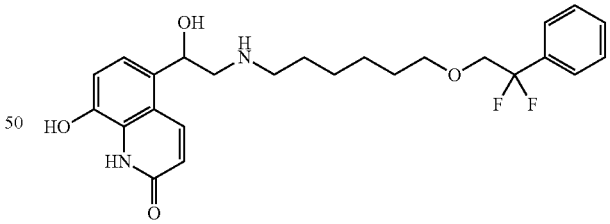

To a solution of Intermediate 26 (1.27 g, 2.3 mmol) in methanol (50 mL) was added 20% palladium on charcoal (300 mg). The mixture was hydrogenated at 30 psi for 3 hours. The catalyst was filtered through Celite and the solvent concentrated. The resulting oil was purified by column chromatography with silica gel eluting with methylene chloride/ethanol/ammonium hydroxide (from 80:8:1 to 40:8:1) to give (R,S)-5-(2-{[6-(2,2-difluoro-2-phenylethoxy)hexyl]amino}-1-hydroxy-ethyl)-8-hydroxyquinolin-2(1H)-one (0.44 g, 41%) as oil.

$^1$H-NMR (400 MHz, dimethylsulfoxide-D6): 1.14-1.21 (m, 2H); 1.28-1.65 (m, 6H); 2.61-2.72 (m, 2H); 3.14-3.18 (m, 2H); 3.90 (t, $J_{F-H}$=13.9 Hz, 2H); 4.96 (dd, $J_1$=8.2 Hz, $J_2$=4.3 Hz, 1H); 6.55 (d, J=9.8 Hz, 1H); 6.80 (d, J=8.2 Hz, 1H); 7.00 (d, J=8.2 Hz, 1H); 7.47-7.54 (m, 5H); 8.16 (d, J=9.8 Hz, 1H).
MS (M+): 496

Intermediate 27. Ethyl (3-methylphenyl)(oxo)acetate

A suspension of selenium dioxide (6.82 g, 61.4 mmol) in ethanol (60 mL) was refluxed for 10 minutes and then, 2-bromo-1-m-tolylethanone (13.1 g, 61.4 mmol) was added. The mixture was refluxed overnight. The cooled reaction was filtered through Celite and the solvent removed under reduced pressure. The residue was diluted with methylene chloride (50 mL), washed with water (2×25 mL), dried (Na$_2$SO$_4$), and concentrated. Purification by column chromatography with silica gel using methylene chloride as eluent gave the title compound (9.6 g, 81%) as oil.

$^1$H NMR (300 MHz, CDCl$_3$): 1.43 (t, J=7.1 Hz, 3H); 2.43 (s, 3H); 4.46 (q, J=7.1 Hz, 2H); 7.38-7.49 (m, 2H); 7.79-7.81 (d, J=6.6 Hz, 2H).

Intermediate 28. Ethyl difluoro(3-methylphenyl)acetate

Obtained from Intermediate 27 (9.6 g, 50 mmol) by the procedure described in Intermediate 1. Ethyl difluoro(3-methylphenyl)acetate was obtained (3.55 g, 80%) as oil.

$^1$H NMR (300 MHz, CDCl$_3$): 1.43 (t, J=7.1 Hz, 3H); 2.43 (s, 3H); 4.46 (q, J=7.1 Hz, 2H); 7.25-7.61 (m, 4H).

Intermediate 29. 2,2-Difluoro-2-(3-methylphenyl)ethanol

Obtained from Intermediate 28 (9.5 g, 40 mmol) by the procedure described in Intermediate 2. The title compound was obtained (5.55 g, 80%) as oil.

$^1$H NMR (300 MHz, CDCl$_3$): 2.43 (s, 3H); 4.00 (t, $J_{F-H}$=13.5 Hz, 2H); 7.25-7.35 (m, 4H).

Intermediate 30. 1-{2-[(6-Bromohexyl)oxy]-1,1-difluoroethyl}-3-methylbenzene Obtained from Intermediate 29 (5.55 g, 32.2 mmol) by the procedure described in Intermediate 3. Purification by column chromatography with silica gel and n-hexane/ethyl acetate (from pure n-hexane to 10:1) as eluent gave the title compound (10.99 g, 100%) as oil.

$^1$H-NMR (300 MHz, CDCl$_3$):1.40-1.60 (m, 2H); 1.81-1.91 (m, 4H); 2.39 (s, 3H); 3.36-3.43 (m, 4H); 3.53 (t, J=6.5 Hz, 2H); 3.82 (t, $J_{F-H}$=13.2 Hz, 2H); 7.24-7.26 (m, 1H); 7.31-7.32 (m, 3H)

Intermediate 31. 2-{6-[2,2-Difluoro-2-(3-methylphenyl)ethoxy]hexyl}-1H-isoindole-1,3(2H)-dione Obtained from intermediate 30 (8.77 g, 26.2 mmol) by the procedure described in Intermediate 8. Purification by column chromatography with silica gel and methylene chloride as eluent gave the title compound (4.0 g, 40%) as oil, $^1$H-NMR (300 MHz, CDCl$_3$): 1.28-1.33 (m, 4H); 1.51-1.56 (m, 2H); 1.62-1.66 (m, 2H); 2.39 (s, 3H); 3.51 (t, J=6.5 Hz, 2H); 3.63-3.68 (m, 2H); 3.81 (t, $J_{F-H}$=13.2 Hz, 2H); 7.30-7.31 (m, 4H); 7.70-7.73 (m, 2H); 7.83-7.86 (m, 2H).

Intermediate 32. {6-[2,2-Difluoro-2-(3-methylphenyl)ethoxy]hexyl}amine

Obtained from Intermediate 31 (4.0 g, 14.4 mmol) by the procedure described in intermediate 9. {6-[2,2-Difluoro-2-(3-methylphenyl)ethoxy]hexyl}amine was obtained (1.93 g, 50%) as oil.

$^1$H-NMR (300 MHz, CDCl$_3$): 1.29-1.32 (m, 4H); 1.37-1.44 (m, 2H); 1.52-1.58 (m, 2H); 2.39 (s, 3H); 2.66 (t, J=6.9 Hz, 2H); 3.53 (t, J=6.5 Hz, 2H); 3.83 (t, $J_{F-H}$=13.2 Hz, 2H): 7.30-7.32 (m, 4H).
MS (M+): 271

Intermediate 33. (R,S)-1-[4-(Benzyloxy)-3-(hydroxymethyl)phenyl]-2-({6-[2,2-difluoro-2-(3-methylphenyl)ethoxy]hexyl}amino)ethanol Obtained from Intermediate 32 (0.50 g, 1.85 mmol) by the procedure described in Intermediate 10. (R,S)-1-[4-(Benzyloxy)-3-(hydroxymethyl)phenyl]-2-({6-[2,2-difluoro-2-(3-methylphenyl)ethoxy]hexyl}amino)ethanol was obtained (0.98 g, 100%) as oil.

$^1$H-NMR (300 MHz, CDCl$_3$): 1.31-1.33 (m, 4H); 1.43-1.56 (m, 5H); 2.39 (s, 3H); 2.61-2.67 (m, 3H); 2.83-2.88 (m, 1H); 3.53 (t, J=6.5 Hz, 2H); 3.82 (t, $J_{F-H}$=13.3 Hz, 2H); 4.62-4.66 (m, 1H); 4.74 (s, 2H); 5.12 (s, 2H); 6.92 (d, J=8.2 Hz, 1H); 7.31-7.43 (m, 11H).

Example 6

(R,S)-4-[2-({6-[2,2-Difluoro-2-(3-methylphenyl)ethoxy]hexyl}amino)-1-hydroxyethyl]-2-(hydroxymethyl)phenol

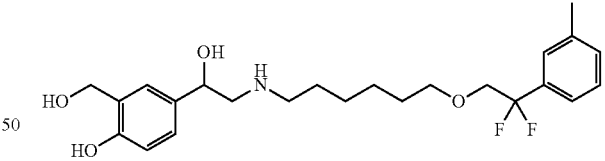

Obtained from Intermediate 33 (0.98 g, 1.85 mmol) by the procedure described in Example 2. Purification by column chromatography with silica gel, using with methylene chloride/ethanol/ammonium hydroxide (40:8:1) as eluent gave (R,S)-4-[2-({6-[2,2-difluoro-2-(3-methylphenyl)ethoxy] hexyl}amino)-1-hydroxyethyl]-2-(hydroxymethyl)phenol (0.44 g, 55%) as oil.

$^1$H-NMR (300 MHz, Cl$_3$CD), 1.25-1.33 (m, 4H); 1.43-1.56 (m, 4H); 2.39 (s, 3H); 2.58-2.70 (m, 4H); 2.76-2.82 (m, 2H); 2.98 (m, 4H); 3.52 (t, J=6.5 Hz, 2H); 3.82 (t, $J_{F-H}$=13.5 Hz, 2H); 4.57-4.60 (d, J=8.0 Hz, 1H); 4.77 (s, 2H); 6.81 (d, J=9.1 Hz, 2H); 7.0 (s, 1H); 7.12 (d, J=9.1 Hz, 1H); 7.26-7.27 (m, 1H); 7.30-7.32 (m, 3H).
MS (M+): 437.

Intermediate 34. (R)-5-(2,2-Dimethyl-4H-1,3-benzodioxin-6-yl)-1,3-oxazolidin-2-one To a solution of (R)-2-amino-1-(2,2-dimethyl-4H-1,3-benzodioxin-6-yl)ethanol (2.53 g, 11.3 mmol) in chloroform (12 mL) was added carbonyldiimidazol (2.75 g, 17 mmol) and triethylamine (2.37 mL, 17 mmol). The mixture was stirred at room temperature overnight. The solvent was removed under reduced pressure and the residue diluted with ethyl acetate (25 mL). The organic layer was washed with water (2×10 mL), brine (10 mL), dried (Na$_2$SO$_4$), and the solvent reduced under reduced pressure. Purification by column chromatography with silica gel and n-hexane/ethyl acetate (1:2) as eluent yielded the title compound (1.63 g, 51%).

1H NMR (300 MHz, CDCl$_3$): 1.55 (s, 6H); 3.54 (t, J=8.1 Hz, 1H); 3.94 (t, J=8.7 Hz, 1H); 4.86 (s, 2H); 5.10 (bs, 1H); 5.56 (t, J=8.1 Hz, 1H); 6.85 (d, J=8.5 Hz, 1H); 7.04-7.07 (m, 1H); 7.15-7.18 (m, 1H).

Intermediate 35. (R)-3-[6-(2,2-Difluoro-2-phenylethoxy)hexyl]-5-(2,2-dimethyl-4H-1,3-benzodioxin-6-yl)-1,3-oxazolidin-2-one To a cooled suspension of 60% sodium hydride (0.37 g, 9.27 mmol) in dimethylformamide (7.5 mL) was added a solution of intermediate 34 (1.65 g, 6.62 mmol) in dimethylformamide (15 mL). The mixture was stirred at 0° C. for 1 hour. Then, a solution of intermediate 7 (3.19 g, 9.93 mmol) in dimethylformamide (9 mL) was added at the same temperature. The mixture was heated to room temperature and stirred for 2 hours, The crude reaction was cooled to 0° C. and then 2N HCl (1.5 mL) and water (20 mL) were added. The solution was extracted with ethyl ether (2×20 mL). The organic layer was washed with water (2×10 mL), dried (Na$_2$SO$_4$), and the solvent removed under reduced pressure. Purification by column chromatography with silica gel eluting with n-hexane/ethyl acetate (1:1) gave (R)-3-[6-(2,2-difluoro-2-phenylethoxy)hexyl]-5-(2,2-dimethyl-4H-1,3-benzodioxin-6-yl)-1,3-oxazolidin-2-one (1.5 g, 46%) as oil.

$^1$H NMR (300 MHz, CDCl$_3$): 1.26-1.53 (m, 6H); 1.55 (s, 6H); 3.18-3.44 (m, 5H); 3.52 (t, J=6.3 Hz, 1H); 3.79-3.9 (m, 3H); 4.12 (q, J=7.1 Hz, 1H); 4.84 (s, 2H); 5.37-5.44 (m, 1H); 6.84 (d, J=8.5 Hz, 1H); 7.00 (s, 1H); 7.12 (d, J=8.5 Hz, 1H); 7.41-7.46 (m, 3H); 7.50-7.53 (m, 2H).

Intermediate 36. (1R)-2-{[6-(2,2-Difluoro-2-phenylethoxy)hexyl]amino}-1-(2,2-dimethyl-4H-1,3-benzodioxin-6-yl)ethanol To a solution of Intermediate 35 (1.5 g, 3.0 mmol) in tetrahydrofuran (60 mL) was added potassium trimethylsilanolate (1.54 g, 12 mmol). The mixture was stirred at 70° C. under inert atmosphere for 2 hours. To the cooled reaction mixture was added saturated solution of ammonium chloride (60 mL). The suspension was extracted with methylene chloride (2×30 mL). The organic layer was washed with water (2×25 mL) and brine (25 mL), dried (Na$_2$SO$_4$) and the solvent removed under reduced pressure. The residue was purified by column chromatography with silica gel and methylene chloride/ethanol/ammonium hydroxide (100:8:1) as eluent. The title compound was obtained (900 mg, 65%) as oil.

$^1$H NMR (300 MHz, CDCl$_3$): 1.2-1.32 (m, 6H): 1.53 (s, 6H); 2.58-2.69 (m, 5H); 2.83-2.88 (m, 1H); 3.52 (t, J=6.5 Hz, 2H); 3.84 (t, J$_{F-H}$=13.2 Hz, 2H); 4.09-4.13 (m, 1H); 4.58-4.61 (m, 1H); 4.84 (s, 2H); 6.78 (d, J=8.5 Hz, 1H); 7.01 (s, 1H); 7.12 (d, J=8.5 Hz, 1H); 7.42-7.44 (m, J$_1$=4.9 Hz, J$_2$=2.2 Hz, 3H); 7.50-7.51 (m, J=3.3 Hz, 2H)

Example 7

4-((1R)-2-{[6-(2,2-Difluoro-2-phenylethoxy)hexyl]amino}-1-hydroxyethyl)-2-(hydroxymethyl)phenol

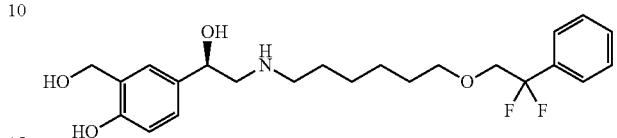

Obtained from Intermediate 35 (0.90 g, 1.94 mmol) by the procedure described in Example 1. Purification by column chromatography with silica gel and methylene chloride/ethanol/ammonium hydroxide (40:8:1) as eluent gave 4-((1R)-2-{[6-(2,2-difluoro-2-phenylethoxy)hexyl]amino}-1-hydroxyethyl)-2-(hydroxymethyl)phenol (0.44 g, 55%) as oil.

$^1$H-NMR (300 MHz, Cl$_3$CD), 1.27-1.31 (m, 4H); 1.41-1.57 (m, 4H); 2.18 (bs, 2H); 2.55, 2.68 (m, 4H); 2.77-2.82 (m, 1H); 3.50 (s, 1H); 3.52 (t, J=6.3 Hz, 2H); 3.84 (t, J$_{F-H}$=13.3 Hz, 2H); 4.58 (dd, J$_1$=9.2 Hz, J$_2$=3.4 Hz, 1H); 4.83 (d, 2H); 6.84 (d, J=8.2 Hz, 1H); 7.02 (d, J=2.0 Hz, 1H); 7.16 (dd, J$_1$=8.4 Hz, J$_2$=2.1 Hz, 1H); 7.42-7.44 (m, 3H); 7.50-7.54 (m, 2H),

MS (M+): 423.

Intermediate 37. 2,2,3,3-Tetrafluoro-4-{[(2E)-3-phenylprop-2-en-1-yl]oxy}butan-1-ol To a solution 2,2,3,3-tetrafluoro-1,4-butanediol (2.0 g, 12.3 mmol) in dimethylformamide (30 mL) was added 60% sodium hydride (0.140 g, 18.4 mmol). The mixture was stirred at room temperature for 1.30 hours. Then, a solution of cinnamyl bromide (3.2 g, 12.3 mmol) in dimethylformamide (40 mL) was added. The mixture was stirred at room temperature overnight and concentrated. The residue was dissolved with ethyl acetate (50 mL), washed with water (2×25 mL) and brine (25 mL), dried (Na$_2$SO$_4$), and the solvent removed under reduced pressure. Purification by column chromatography with silica gel and n-hexane/ethyl acetate (from pure n-hexane to 5:1) gave the title compound (1.8 g, 54%) as oil.

$^1$H NMR (300 MHz, CDCl$_3$): 2.78-3.18 (bs, 1H); 3.80-4.05 (m, 4H); 4.28 (d, J=9 Hz, 2H); 6.18-6.32 (m, 1H); 6.58-6.62 (m, 1H); 7.20-7.35 (m, 5H).

Intermediate 38. 2,2,3,3-Tetrafluoro-4-{[(2E)-3-phenylprop-2-en-1-yl]oxy}butanal Obtained from intermediate 37 (1.80 g, 6.47 mmol) by the procedure described in Intermediate 13. 2,2,3,3-Tetrafluoro-4-{[(2E)-3-phenylprop-2-en-1-yl]oxy}butanal was obtained (1.37 g, 77%) as oil.

$^1$H NMR (300 MHz, CDCl$_3$): 3.80-4.05 (m, 4H); 4.20-4.40 (m, 2H); 6.18-6.32 (m, 1H); 6.58-6.62 (t, J$_{F-H}$=18 Hz, 1H); 7.20-7.35 (m, 5H); 9.50 (bs, 1H).

Intermediate 39. Ethyl (2E)-4,4,5,5-tetrafluoro-6-{[(2E)-3-phenylprop-2-en-1-yl]oxy}-hex-2-enoate Obtained from Intermediate 38 (1.37 g, 4.96 mmol) by the procedure described in Intermediate 20. Purification by column chromatography with silica gel using n-hexane/ethyl acetate (15:1) as eluent gave the title compound (1.2 g, 70%) as oil.

¹H NMR (300 MHz, CDCl₃): 1.20-1.35 (m, 3H); 3.80-4.05 (m, 2H); 4.20-4.40 (m, 4H); 5.90-6.10 (q, $J_{F-H}$=13.5 Hz, 1H); 6.20-6.38 (m, 2H); 6.60-6.70 (m, 1H); 7.21-7.31 (m, 5H).

Intermediate 40. Ethyl 4,4,5,5-tetrafluoro-6-(3-phenylpropoxy)hexanoate

Obtained from Intermediate 39 (1.2 g, 3.46 mmol) by the procedure described in intermediate 21. Ethyl 4,4,5,5-tetrafluoro-6-(3-phenylpropoxy)hexanoate was obtained (1.0 g, 82%) as oil.

¹H NMR (300 MHz, CDCl₃): 1.22 (t, J=9 Hz, 3H); 1.83-1.95 (m, 2H) 2.30-2.55 (m, 2H); 2.70-2.63 (m, 2H); 2.85-2.80 (m, 2H); 3.50-3.60 (m, 2H); 3.80-3.95 (q, $J_{F-H}$=18.0 Hz, 2H); 4.10-4.20 (m, 2H); 7.15-7.25 (m, 3H); 7.25-7.41 (m, 2H).

Intermediate 41. 4,4,5,5-Tetrafluoro-6-(3-phenylpropoxy)hexan-1-ol

Obtained from Intermediate 40 (1.0 g, 2.85 mmol) by the procedure described in Intermediate 2. Purification by column chromatography with silica gel and n-hexane/ethyl acetate (from 10:1 to 5:1) as eluent gave the title compound (0.68 g, 82%) as oil, ¹H NMR (300 MHz, CDCl₃): 1.70-2.01 (m, 4H); 2.05-2.15 (m, 2H); 2.65-2.75 (m, 2H); 3.50-3.60 (m, 2H); 3.62-3.75 (m, 2H); 3.78-3.95 (t, $J_{F-H}$=18.0 Hz, 2H); 7.05-7.20 (m, 3H); 7.20-7.35 (m, 2H).

Intermediate 42. 4,4,5,5-Tetrafluoro-6-(3-phenylpropoxy)hexanal

Obtained from intermediate 41 (0.68 g, 2.20 mmol) by the procedure described in Intermediate 13. 4,4,5,5-Tetrafluoro-6-(3-phenylpropoxy)hexanal was obtained (0.32 g, 47%) as oil.

¹H NMR (300 MHz, CDCl₃): 1.80-2.00 (m, 2H); 2.25-2.55 (m, 2H); 2.65-2.85 (m, 4H); 3.50-3.65 (m, 2H); 3.75-3.95 (t, $J_{F-H}$=18.0 Hz, 2H); 7.05-7.20 (m, 3H); 7.20-7.35 (m, 2H); 9.80 (bs, 1H).

Intermediate 43. (R,S)-1-(2,2-Dimethyl-4H-1,3-benzodioxin-6-yl)-2-{[4,4,5,5-tetrafluoro-6-(3-phenylpropoxy)hexyl]amino}ethanol Obtained from intermediate 42 (0.32 g, 1.05 mmol) by the procedure described in Intermediate 18. Purification by column chromatography with silica gel and methylene chloride/triethylamine (100:1) as eluent gave the title compound (0.17 g, 32%) as oil.

MS (M+): 513

Example 8

(R,S)-2-(Hydroxymethyl)-4-(1-hydroxy-2-{[4,4,5,5-tetrafluoro-6-(3-phenylpropoxy)hexyl]amino}ethyl)phenol

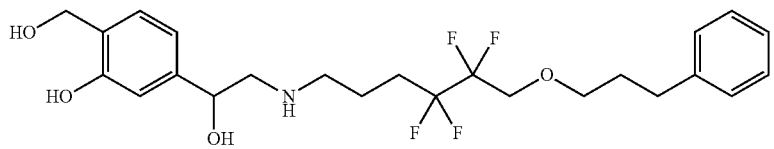

Obtained from Intermediate 43 (0.17 g, 0.33 mmol) by the procedure described in Example 1. Purification by column chromatography with silica gel and methylene chloride/methanol/ammonium hydroxide (40:4:0.2) as eluent gave (R,S)-2-(hydroxymethyl)-4-(1-hydroxy-2-{[4,4,5,5-tetrafluoro-6-(3-phenylpropoxy)hexyl]amino}ethyl)phenol (0.15 g, 96%) as oil.

¹H-NMR (400 MHz, dimethylsulfoxide-D6): 1.57-1.64 (m, 2H); 1.78-1.86 (m, 2H); 2.05-2.17 (m, 2H); 2.56-2.63 (m, 4H); 3.54 (d, J=6.4 Hz, 2H); 3.91 (d, $J_{F-H}$=14.9 Hz, 3H); 4.45-4.51 (m, 3H); 4.91 (t, J=5.6 Hz, 1H); 5.01 (d, J=3.7 Hz, 1H); 6.68 (d, J=7.9 Hz, 1H); 6.97 (dd, $J_1$=8.3 Hz, $J_2$=2.1 Hz, 1H); 7.15-7.20 (m, 3H); 7.25-7.30 (m, 3H); 9.15 (bs, 1H),

MS (M+): 473

Intermediate 44. N-Benzyl-6-(2,2-difluoro-2-phenylethoxy)hexan-1-amine

A solution of Intermediate 7 (5.0 g, 15.6 mmol) and benzyl amine (3.4 mL, 31.1 mmol) was heated at 120° C. for two hours. The crude reaction was treated with ethyl ether and the resulting solid was filtered. The solvent was concentrated and the resulting oil was purified by column chromatography with silica gel and methylene chloride/methanol (from 99:1 to 95:5) as eluent, to yield N-benzyl-6-(2,2-difluoro-2-phenylethoxy)hexan-1-amine (3.2 g, 59%) as oil.

¹H NMR (300 MHz, CDCl₃): 1.24-1.32 (m, 2H); 1.46-1.63 (m, 4H); 2.58-2.64 (m, 4H); 3.49-3.53 (t, J=6.5 Hz, 2H); 3.79-3.88 (m, 4H); 7.30-7.33 (m, 5H); 7.42-7.44 (m, 3H); 7.50-7.54 (m, 2H).

Intermediate 45. (R,S)-2-{Benzyl[6-(2,2-difluoro-2-phenylethoxy)hexyl]amino}-1-[4-(benzyloxy)-3-nitrophenyl]ethanol A solution of Intermediate 44 (3.2 g, 9.22 mmol) and 2-(3-nitro-4-phenoxyphenyl)-oxirane (2.27 g, 8.38 mmol) was heated at 120° C. for 2 hours. An HPLC-MS analysis of the crude reaction revealed that there were two main products: (R,S)-2-{benzyl[6-(2,2-difluoro-2-phenylethoxy)hexyl]amino}-1-[4-(benzyloxy)-3-nitrophenyl]ethanol and the corresponding isomer (R,S)-1-{benzyl[6-(2,2-difluoro-2-phenylethoxy)hexyl]amino}-1-[4-(benzyloxy)-3-nitrophenyl]ethanol (60:40). The reaction was cooled and the resulting oil (5.18 g) was used in the next step without further purification.

Intermediate 46. (R,S)-1-[3-Amino-4-(benzyloxy)phenyl]-2-{benzyl[6-(2,2-difluoro-2-phenylethoxy)hexyl]amino}ethanol To a solution of Intermediate 45 (5.18 g, 8.38 mmol) in ethanol (110 mL) was added tin dichloride (6.34 g, 33.5 mmol). The mixture was refluxed for 2 hours. The reaction was cooled and the solvent was removed under reduced pressure. The resulting oil (3.92 g) was used in the next step without further purification.

Example 9

(R,S)-[5-(2-{[6-(2,2-Difluoro-2-phenylethoxy)hexyl]amino}-1-hydroxy-ethyl)-2-hydroxyphenyl]formamide

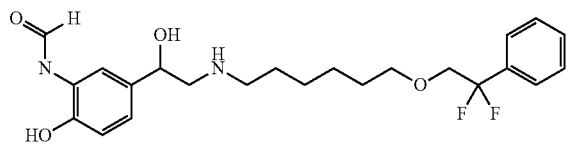

A mixture of formic acid (0.62 mL, 13.32 mmol) and acetic anhydride (0.78 g, 7.65 mmol) were heated at 50° C. for 15 minutes. The mixture was cooled to 10° C. and a solution of intermediate 46 (3.2 g) in tetrahydrofuran (18 mL) and toluene (18 mL) was added dropwise. The mixture was stirred at room temperature for 20 minutes. The solvent was removed under reduced pressure. The resulting oil was purified by column chromatography with silica gel and methylene chloride/methanol (from 98:2 to 95:5) as eluent to give crude dibenzylated (R,S)-[5-(2-{[6-(2,2-difluoro-2-phenylethoxy)hexyl]-amino}-1-hydroxy-ethyl)-2-hydroxyphenyl]formamide (2.44 g) as oil. A solution of this oil in ethanol (150 mL) was hydrogenated in the presence of palladium on charcoal (0.3 g) for 4 hours. The mixture was then filtered over Celite and the solvent removed under reduced pressure. The residue was purified by column chromatography with silica gel and methylene chloride/ethanol/ammonium hydroxide (80:8:1) as eluent to give (R,S)-[5-(2-{[6-(2,2-difluoro-2-phenylethoxy)hexyl]amino}-1-hydroxy-ethyl)-2-hydroxyphenyl]formamide (464 mg, 14% three step overall yield) as oil.

$^1$H-NMR (400 MHz, dimethylsulfoxide-D6): 1.17-1.18 (m, 4H); 1.26-1.33 (m, 2H); 1.36-1.44 (m, 2H); 2.44-2.47 (m, 2H); 2.50-2.57 (m, 2H); 3.41-3.45 (d, J=6.5 Hz, 2H); 3.90 (d, J=13.7 Hz, 2H); 4.42-4.48 (m, 1H); 6.77 (d, J=8.2 Hz, 1H); 6.85 (dd, J$_1$=8.2 Hz, J$_2$=2.0 Hz, 1H); 7.45-7.53 (m, 5H); 7.99 (d, J=2.0 Hz, 1H); 8.24 (s, 1H); 9.51 (bs, 1H).

MS (M+): 436

Intermediate 47. Ethyl (3-bromophenyl)(oxo)acetate

Obtained from 2-bromo-1-m-bromophenylethanone (27.7 g, 0.10 mol) by the procedure described in Intermediate 27. Purification by column chromatography with silica gel using methylene chloride as eluent gave the title compound (20.7 g, 81%) as oil.

$^1$H-NMR (300 MHz, CDCl$_3$): 1.40 (t, J=7.1 Hz, 3H); 4.45 (q, J=7.1 Hz, 2H); 7.40 (t, J=9.0 Hz, 1H); 7.80 (d, J=9.0 Hz, 1H); 7.98 (d, J=9.0 Hz, 1H); 8.20 (s, 1H).

Intermediate 48. Ethyl(3-bromophenyl)difluoroacetate

Obtained from intermediate 47 (28.80 g, 0.112 mol) by the procedure described in Intermediate 1. Purification by column chromatography with silica gel and n-hexane/ethyl acetate (4:1) as eluent gave the title compound (26.3 g, 84%) as oil.

$^1$H-NMR (300 MHz, CDCl$_3$): 1.30 (t, J=7.1 Hz, 3H); 4.30 (q, J=7.1 Hz, 2H); 7.30 (t, J=9.0 Hz, 1H); 7.55 (d, J=9.0 Hz, 1H); 7.65 (d, J=9.0 Hz, 1H); 7.78 (s, 1H).

Intermediate 49. 2-(3-Bromopheny)-2,2-difluoroethanol

Obtained from Intermediate 48 (21.1 g, 75.8 mmol) by the procedure described in Intermediate 2. The title compound was obtained (17.2 g, 96%) as oil.

$^1$H-NMR (300 MHz, CDCl$_3$): 3.95 (t, J$_{F-H}$=13.5 Hz, 2H); 7.30 (t, J=9.0 Hz, 1H); 7.55 (d, J=9.0 Hz, 1H); 7.65 (d, J=9.0 Hz, 1H); 7.70 (s, 1H).

Intermediate 50. 1-Bromo-3-{2-[(6-bromohexyl)oxy]-1,1-difluoroethyl}benzene

Obtained from Intermediate 49 (17.6 g, 74 mmol) by the procedure described in Intermediate 3. The crude oil was purified by distillation to yield the title compound as oil of 60% of purity (9.5 g). The distillation residue was purified by column chromatography with silica gel and methylene chloride as eluent to yield a second batch of 1-bromo-3-{2-[(6-bromohexyl)oxy]-1,1-difluoroethyl}benzene of 65% of purity (15.2 g) (overall yield: 53%).

$^1$H NMR (300 MHz, CDCl$_3$): 1.25-1.55 (m, 8H); 1.81-1.88 (m, 1H); 3.37-3.41 (m, 1H); 3.46-3.53 (m, 2H); 3.78-3.86 (m, 2H); 7.30-7.34 (m, 1H); 7.44-7.46 (m, 1H); 7.58 (d, J=8.0 Hz, 1H); 7.67 (s, 1H).

Intermediate 51. (R,S)-5-(2,2-Dimethyl-4H-1,3-benzodioxin-6-yl)-1,3-oxazolidin-2-one To a solution of (R,S)-2-amino-1-(2,2-dimethyl-4H-1,3-benzodioxin-6-yl)ethanol (5.0 g, 22.3 mmol) in methylene chloride (100 mL) was added ditertbutyl dicarbonate (5.35 g, 24.5 mmol) and triethylamine (3.4 mL, 24.5 mmol). The mixture was stirred at room temperature for 2 hours. The organic layer was washed with water (2×10 mL), brine (10 mL), dried (Na$_2$SO$_4$), and the solvent reduced under reduced pressure. Trituration with ethyl ether gave the protected starting amine (6.8 g, 94%) as an off-white solid. A solution of this solid in dimethylformamide (30 mL) was added dropwise to a cooled suspension of sodium hydride (1.07 g, 27 mmol) in dimethylformamide (30 mL). The mixture was allowed to reach room temperature and then was stirred at 40° C. overnight. The solvent was removed under reduced pressure. The residue was diluted with ethyl acetate (60 mL) and the organic layer was acidified with 2N HCl, washed with water (2×30 mL), brine (2×30 mL), dried (Na$_2$SO$_4$), and the solvent reduced under reduced pressure. The title compound was obtained (4.4 g, 85%) as oil.

$^1$H NMR (300 MHz, CDCl$_3$): 1.52-1.61 (m, 6H); 3.55 (t, J=8.2 Hz, 1H); 3.94 (t, J=8.7 Hz, 1H); 4.86 (s, 2H); 5.42 (bs, 1H); 5.55 (t, J=8.1 Hz, 1H); 6.85 (d, J=8.5 Hz, 1H); 7.04 (d, J=1.6 Hz, 1H); 7.17 (dd, J$_1$=8.4 Hz, J$_2$=2.3 Hz, 1H)

Intermediate 52. (R,S)-3-{6-[2-(3-Bromophenyl)-2,2-difluoroethoxy]hexyl}-5-(2,2-dimethyl-4H-1,3-benzodioxin-6-yl)-1,3-oxazolidin-2-one Obtained from Intermediate 50 (4.6 g of 50% purity, 5.7 mmol) and intermediate 51 (1.14 g, 4.56 mmol) by the procedure described in Intermediate 35. Purification by column chromatography with silica gel and methylene chloride/methanol (from pure methylene chloride to 98:2) as eluent gave the title compound (2.06 g, 80%) as oil.

$^1$H NMR (300 MHz, CDCl$_3$): 1.30-1.32 (m, 4H); 1.52-1.58 (m, 3H); 1.54 (s, 6H); 3.18-3.43 (m, 4H); 3.48-3.54 (m, 2H); 3.77-3.88 (m, 3H); 4.84 (s, 2H); 5.40 (t, J=8.0 Hz, 1H); 6.84 (d, J=8.5 Hz, 1H); 7.00 (d, J=1.6 Hz, 1H); 7.12 (dd, J$_1$=8.4 Hz, $J_2$ 2.3 Hz, 1H); 7.31-7.34 (m, 1H); 7.44-7.46 (m, 1H); 7.56-7.59 (d, J=8.0 Hz, 1H); 7.67 (s, 1H).

Intermediate 53. (R,S)-2-({6-[2-(3-bromophenyl)-2,2-difluoroethoxy]hexyl}amino)-1-(2,2-dimethyl-4H-1,3-benzodioxin-6-yl)ethanol Obtained from intermediate 52 (1.24 g, 2.18 mmol) by the procedure described in Intermediate 36. Purification by column chromatography with silica gel and methylene chloride/methanol/ammonium hydroxide (100:8:1) as eluent gave the title compound (0.9 g, 76%) as oil.

1H NMR (300 MHz, CDCl$_3$): 1.23-1.32 (m, 6H); 1.54 (s, 6H); 2.58-2.70 (m, 3H); 2.84-2.89 (m, 1H); 3.49-3.53 (m, 2H); 3.69-3.86 (m, 4H); 4.59-4.64 (dd, $J_1$=9.2 Hz, $J_2$=3.4 Hz, 1H); 4.85 (s, 2H); 6.79 (d, J=8.5 Hz, 1H); 7.01 (s, 1H); 7.11-7.14 (m, 1H); 7.32 (d, J=7.7 Hz, 1H); 7.44-7.47 (m, 1H); 7.58 (d, J=8.0 Hz, 1H); 7.67 (s, 1H).

Example 10

(R,S)-4-[2-({6-[2-(3-Bromophenyl)-2,2-difluoroethoxy]hexyl}amino)-1-hydroxyethyl]-2-(hydroxymethyl)phenol

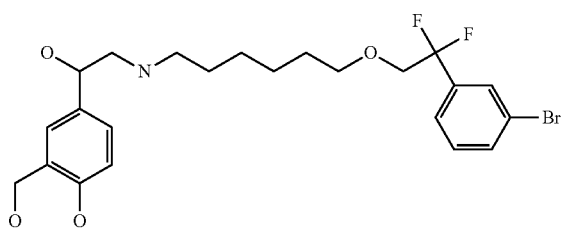

Obtained from Intermediate 53 (0.90 g, 1.66 mmol) by the procedure described in Example 1. Purification by column chromatography with silica gel, using methylene chloride/ethanol/ammonium hydroxide (40:8:1) as eluent gave (R,S)-4-[2-({6-[2-(3-bromophenyl)-2,2-difluoroethoxy]hexyl}amino)-1-hydroxyethyl]-2-(hydroxymethyl)phenol (0.36 g, 55%) as an off-white solid.

$^1$H-NMR (300 MHz. Cl$_3$CD): 1.27-1.30 (m, 4H); 1.41-1.56 (m, 4H); 2.51-2.77 (m, 4H); 3.51 (t, J=6.3 Hz, 2H); 3.53 (bs, 4H); 3.82 (t, $J_{F-H}$=12.8 Hz, 2H); 4.53-4.57 (m, 1H); 4.76 (s, 2H); 6.80 (d, J=8.2 Hz, 1H); 6.96 (d, J=1.9 Hz, 1H); 7.11 (dd, $J_1$=8.0, $J_2$=1.9 Hz, 1H); 7.32 (d, J=8.0 Hz, 1H); 7.44-7.47 (m, 1H); 7.56-7.59 (m, 1H); 7.67 (s, 1H).
MS (M+): 502.

Intermediate 54. (R,S)-3-{6-[2-(3-Aminophenyl)-2,2-difluoroethoxy]hexyl}-5-(2,2-dimethyl-4H-1,3-benzodioxin-6-yl)-1,3-oxazolidin-2-one To a solution of Intermediate 52 (4.65 g, 8.18 mmol) in toluene (20 mL) was added bis(dibenzylideneacetone)palladium (230 mg, 0.4 mmol), tri-tert-butylphosphine (83 □L, 0.4 mmol) and lithium bis(trimethylsilyl)amide, 1M solution in hexane (9 mL, 9 mmol) under inert atmosphere. The mixture was stirred at room temperature overnight. The reaction was diluted with ethyl ether (20 mL) and 2N HCl was added (0.25 mL). The organic layer was washed with 2N sodium hydroxide (2×20 mL), water (20 mL) and brine (20 mL), dried (Na$_2$SO$_4$); and the solvent removed under reduced pressure. Purification by column chromatography with silica gel and methylene chloride/methanol (from pure methylene chloride to 98:2) as eluent gave the title compound (2.71 g, 66%) as oil.

1H NMR (300 MHz, CDCl$_3$): 1.30-1.38 (m, 4H); 1.48-1.58 (m, 3H); 1.55 (s, 6H); 3.23-3.43 (m, 3H); 3.52 (t, J=6.3 Hz, 2H); 3.76-3.89 (m, 4H); 4.85 (s, 2H); 5.40 (t, J=8.0 Hz, 1H); 6.72-6.76 (m, 1H); 6.82-6.89 (m, 3H); 7.01 (d, J=1.1 Hz, 1H); 7.11-7.22 (m, 2H).

Intermediate 55. (R,S)—N-{3-[2-((6-[5-(2,2-Dimethyl-4H-1,3-benzodioxin-6-yl)-2-oxo-1,3-oxazolidin-3-yl]hexyl}oxy)-1,1-difluoroethyl]phenyl}urea To a solution of Intermediate 54 (2.71 g, 5.4 mmol) in acetic acid (20 ml) and water (10 ml) was added a solution of potassium cyanide (0.87 g, 10.7 mmol) in water (20 mL). The mixture was stirred overnight under inert atmosphere. The crude reaction was diluted with water and extracted with ethyl acetate (3×15 mL). The combined organic extracts were washed with water (2×15 mL) and brine (20 mL), dried (Na$_2$SO$_4$), and concentrated. Purification by column chromatography with silica gel and ethyl acetate as eluent gave the title compound (2.2 g, 73%) as oil.

$^1$H NMR (300 MHz, CDCl$_3$): 1.30-1.38 (m, 4H); 1.47-1.58 (m, 3H); 1.55 (s, 6H); 3.25-3.41 (m, 3H); 3.45-3.51 (m, 2H); 3.79-3.93 (m, 4H); 4.85 (s, 2H); 5.15 (bs, 2H); 5.46 (t, J=8.2 Hz, 1H); 6.87 (d, J=8.5 Hz, 1H); 7.00 (d, J=1.9 Hz, 1H); 7.12-7.16 (m, 2H); 7.30-7.38 (m, 2H): 7.88-7.90 (m, 1H); 8.00 (bs, 1H).

Intermediate 56. (R,S)—N-(3-{2-[(6-{[2-(2,2-Dimethyl-4H-1,3-benzodioxin-6-yl)-2-hydroxyethyl]amino}hexyl)oxy]-1,1-difluoroethyl}phenyl)urea Obtained from Intermediate 55 (2.2 g, 4 mmol) by the procedure described in Intermediate 36. Purification by column chromatography with silica gel and methylene chloride/ethanol/ammonium hydroxide (100:8:1) as eluent gave the title compound (1.12 g, 54%) as oil.

1H NMR (300 MHz, CDCl$_3$): 1.22-1.28 (m, 4H); 1.39-1.49 (m, 4H); 1.53 (s, 6H); 2.56-2.87 (m, 3H); 3.48 (t, J=6.0 Hz, 2H); 3.69-3.86 (m, 4H): 4.68 (dd, $J_1$=9.2 Hz, $J_2$=3.7 Hz, 1H); 4.82 (s, 2H); 4.95 (bs, 2H); 6.79 (d, J=8.2 Hz, 1H); 7.00 (d, J=1.6 Hz, 1H); 7.11-7.20 (m, 2H); 7.33-7.39 (m, 2H); 7.58-7.61 (m, 1H).

Example 11

(R,S)—N-[3-(1,1-Difluoro-2-{[6-({2-hydroxy-2-[4-hydroxy-3-(hydroxymethyl)phenyl]ethyl}amino)hexyl]oxy}ethyl)phenyl]urea

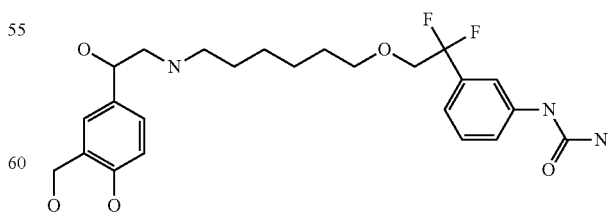

Obtained from Intermediate 56 (1.12 g, 2.15 mmol) by the procedure described in Example 1. Purification by column chromatography with silica gel, using methylene chloride/ethanol/ammonium hydroxide (40:8:1) as eluent gave (R,S)—N-[3-(1,1-difluoro-2-{[6-({2-hydroxy-2-[4-hydroxy-3-hydroxymethyl)phenyl]ethyl}amino)hexyl]oxy}ethyl)phenyl]-urea (0.49 g, 46%) as an off-white solid.

$^1$H-NMR (300 MHz, DMSO-D6): 1.20-1.26 (m, 4H); 1.32-1.47 (m, 4H); 2.54-2.57 (m, 4H); 3.45 (t, J=6.6 Hz, 2H); 3.86 (t, $J_{F-H}$=13.9 Hz, 2H); 4.46-4.51 (m, 3H); 4.94 (bs, 1H); 5.04 (bs, 1H); 5.92 (s, 2H); 6.68 (d, J=8.2 Hz, 1H); 6.98 (dd, $J_1$=8.0, $J_2$=1.9 Hz, 1H); 7.03 (d, J=8.0 Hz, 1H); 7.25 (d, J=1.9 Hz, 1H); 7.32 (t, J=7.8 Hz, 1H); 7.44-7.47 (m, 1H); 7.65 (s, 1H); 8.74 (s, 1H).

MS (M+): 481.

Intermediate 57. 1-bromo-3-{2-[(6-bromohexyl)oxy]-1,1-difluoroethyl}benzene

A solution of benzyl alcohol (3.2 mL, 30.9 mmol) in dimethylformamide (100 mL) was cooled to 0° C. and 60% sodium hydride (1.23 g, 30.9 mmol) was slowly added. The mixture was stirred at room temperature for 0.5 hours, then cooled to 0° C. again and a solution of Intermediate 50 (12.72 g, 20.6 mmol) in dimethylformamide (65 mL) was slowly added. The mixture was stirred 4 hours at room temperature. The crude reaction was cooled to 0° C. and water (3 mL) was added and then was concentrated. The residue was dissolved with methylene chloride (150 mL), washed with water (2×75 mL) and brine (1×50 mL), dried ($Na_2SO_4$), and the solvent removed under reduced pressure. Purification by column chromatography with silica gel and methylene chloride as eluent gave the title compound (5.1 g, 57%) as oil.

$^1$H NMR (300 MHz, $CDCl_3$): 1.25-1.36 (m, 4H); 1.50-1.62 (m, 4H); 3.43-3.52 (m, 4H); 3.81 (t, J=12.8 Hz, 2H); 4.50 (s, 2H); 7.26-7.35 (m, 6H); 7.43-7.46 (m, 1H); 7.57 (d, J=8.0 Hz, 1H); 7.68 (d, J=1.6 Hz, 1H).

Intermediate 58. [3-(2-{[6-(benzyloxy)hexyl]oxy}-1,1-difluoroethyl)phenyl]amine Obtained from Intermediate 57 (5.04 g, 11.88 mmol) by the procedure described in Intermediate 54. Purification by column chromatography with silica gel and methylene chloride/methanol (from pure methylene chloride to 99:1) as eluent gave the title compound (3.9 g, 90%) as oil.

$^1$H NMR (300 MHz, $CDCl_3$): 1.28-1.38 (m, 4H); 1.52-1.66 (m, 4H); 3.43-3.54 (m, 4H); 3.80 (t, J=13.5 Hz, 2H); 4.50 (s, 2H); 6.73 (dd, $J_1$=8.0 Hz, $J_2$=1.6 Hz, 1H); 6.81-6.82 (m, 1H); 6.87 (d, J=7.7 Hz, 1H); 7.19 (t, J=7.8 Hz, 1H); 7.27-7.31 (m, 1H); 7.32-7.38 (m, 4H).

Intermediate 59. Ethyl N-({[3-(2-{[6-(benzyloxy)hexyl]oxy}-1,1-difluoroethyl)phenyl]amino}carbonyl)glycinate To a solution of Intermediate 58 (3.9 g, 10.7 mmol) in methylene chloride (35 mL) was added ethyl isocyanatoacetate (1.38 mL, 12.3 mmol). The mixture was stirred at room temperature for 5 hours. The crude reaction was cooled to 0° C. and then methanol (2.3 mL) was added. The mixture was stirred at room temperature for 0.5 hours and the solvent was removed under reduced pressure. Purification by column chromatography using methylene chloride/methanol (from pure methylene chloride to 98:2) as eluent gave the title compound (5.1 g, 95%) as oil.

$^1$H NMR (300 MHz, $CDCl_3$): 1.27-1.36 (m, 7H); 1.49-1.65 (m, 4H); 3.51 (m, 4H); 3.80 (t, $J_{F-H}$=12.9 Hz, 2H); 4.02 (s, 2H); 4.22 (q, J=7.2 Hz, 2H); 4.53 (s, 2H); 7.13-7.18 (m, 2H); 7.30-7.36 (m, 6H); 7.58 (d, J=8.0 Hz, 1H).

Intermediate 60. N-({[3-(2-{[6-(benzyloxy)hexyl]oxy)-1,1-difluoroethyl)phenyl]amino}carbonyl)glycine To a solution of intermediate 59 (5.09 g, 10 mmol) in ethanol (30 mL) was added 2N NaOH (18 mL, 35 mmol). The mixture was stirred at room temperature for 3 hours. The crude reaction was concentrated and the residue was diluted with ethyl acetate (50 mL) and washed with water (2×25 mL). The aqueous layer was acidified to pH 2 with HCl and then extracted with ethyl acetate (2×50 mL). The organic layers were dried ($Na_2SO_4$) and the solvent removed under reduced pressure. The titled compound was obtained (4.23 g, 88%).

$^1$H NMR (300 MHz, $CDCl_3$): 1.25-1.34 (m, 4H); 1.49-1.58 (m, 4H); 3.49 (t, J=6.6 Hz, 4H); 3.80 (t, $J_{F-H}$=12.9 Hz, 2H); 3.92 (s, 2H); 4.52 (s, 2H); 5.81 (bs, 1H); 7.15 (d, J=7.4 Hz, 1H); 7.29-7.34 (m, 6H); 7.40 (d, J=1.9 Hz, 2H); 7.66 (bs, 1H).

Intermediate 61. 3-[3-(2-{[6-(benzyloxy)hexyl]oxy}-1,1-difluoroethyl)phenyl]imidazolidine-2,4-dione A solution of Intermediate 60 (3.42 g, 7.4 mmol), water (20 mL) and concentrated HCl (5.5 mL) was heated at 140° C. for 12 hours. The reaction was cooled. The crude was extracted with ethyl acetate (50 mL) and washed with saturated solution of sodium bicarbonate (2×20 mL), water (2×20 mL) and brine (1×20 mL), dried ($Na_2SO_4$) and concentrated. The titled compound was obtained (2.52 g, 76%) as oil.

1H NMR (300 MHz, $CDCl_3$): 1.33 (bs, 4H); 1.58 (bs, 4H); 3.43-3.54 (m, 4H); 3.84 (t, $J_{F-H}$=13.0 Hz, 2H); 4.13 (s, 2H); 4.49 (s, 2H); 5.56 (bs, 1H); 7.34 (bs, 6H); 7.53 (bs, 3H); 7.61 (s, 1H).

Intermediate 62. 3-(3-{1,1-difluoro-2-[(6-hydroxyhexyl)oxy]ethyl}phenyl)imidazolidine-2,4-dione To a solution of Intermediate 61 (2.52 g, 5.65 mmol) in ethanol (120 mL) was added palladium on charcoal (300 mg). The mixture was bidrogenated at 40 psi for 4 hours. The catalyst was filtered through Celite and the solvent removed under pressure to give the title compound (1.94 g, 96%) as oil.

$^1$H NMR (300 MHz, $CDCl_3$): 1.23-1.32 (m, 4H); 1.50-1.59 (m, 3H); 3.50-3.62 (m, 4H); 3.73 (q, J=7.1 Hz, 1H); 3.86 (t, $J_{F-H}$=12.8 Hz, 2H); 4.17 (s, 2H); 5.99 (bs, 1H); 7.52-7.56 (m, 4H); 7.61 (bs, 1H).

Intermediate 63. 6-{2-[3-(2,5-dioximidazolidin-1-yl)phenyl]-2,2-difluoroethoxy}hexyl methanesulfonate Intermediate 62 (1.94 g, 5.45 mmol) was dissolved in methylene chloride (15 mL) and triethylamine (1.21 mL, 8.72 mmol) was then added. The mixture was cooled to 0° C. and a solution of methanesulfonyl chloride (0.680 mL, 8.72 mmol) in methylene chloride (5 mL) was slowly added at the same temperature. The mixture was stirred at room temperature for 16 hours. The crude reaction was cooled to 0° C. and then 50% solution water/ammonium hydroxide (40 mL) was added. The organic layer was washed with water (2×40 mL), brine (1×40 mL), dried ($Na_2SO_4$) and concentrated. The title compound was obtained (2.4 g, 100%) as oil.

$^1$H NMR (300 MHz, $CDCl_3$): 1.34-1.43 (m, 4H); 1.54-1.72 (m, 6H); 3.0 (s, 3H); 3.53 (t, J=6.2 Hz, 2H); 3.86 (t, $J_{F-H}$=12.8 Hz, 2H); 4.17 (s, 2H); 5.88 (bs, 1H); 7.54 (bs, 4H); 7.62 (bs, 1H).

Intermediate 64. 3-(3-{2-[(6-{[2-(2,2-dimethyl-4H-1,3-benzodioxin-6-yl)-2-hydroxyethyl]amino}hexyl) oxy]-1,1-difluoroethyl}phenyl)imidazolidine-2,4-dione To a solution of Intermediate 63 (2.4 g, 5.4 mmol) in dimethylformamide (30 mL) was added (R,S)-2-amino-1-(2, 2-dimethyl-4H-1,3-benzodioxin-6-yl)ethanol (1.64 g, 7.33 mmol) and tetrabutylammonium bromide (1.74 g, 5.4 mmol). The mixture was stirred at room temperature for 98 hours. The crude reaction was concentrated and the residue was diluted with methylene chloride (50 mL) and washed with water (2×25 mL). The organic layer was dried (Na$_2$SO$_4$) and the solvent removed under reduced pressure. Purification by column chromatography using methylene chloride/ethanol/ ammonium hydroxide (100:8:1) as eluent gave the title compound (0.67 g, 22%) as oil.

$^1$H NMR (300 MHz, CDCl$_3$): 1.22-1.33 (m, 3H); 1.54 (s, 6H); 2.57-2.67 (m, 3H); 2.82-2.87 (m, 1H); 3.52 (t, J=6.5 Hz, 2H); 3.69-3.76 (m, 2H); 3.81-3.90 (m, 2H); 4.13 (s, 2H); 4.64 (dd, J$_1$=9.2 Hz, J$_2$=3.4 Hz, 1H); 4.85 (s, 2H); 6.79 (d, J=8.5 Hz, 1H); 7.01 (s, 1H); 7.13 (dd, J$_1$=8.4 Hz, J$_2$=2.1 Hz, 1H); 7.28 (m, 1H); 7.51-7.56 (m, 2H); 7.62 (bs, 1H).

Example 12

(R,S-)3-[3-(1,1-difluoro-2-{[6-({2-hydroxy-2-[4-hydroxy-3-(hydroxymethyl)phenyl]ethyl}amino) hexyl]oxy}ethyl)phenyl]imidazolidine-2,4-dione

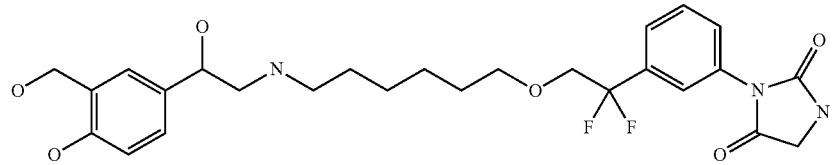

Obtained from Intermediate 64 (0.67 g, 1.20 mmol) by the procedure described in Example 1. Purification by column chromatography with silica gel and methylene chloride/ethanol/ammonium hydroxide (40:8:1) as eluent gave 3-[3-(1,1-difluoro-2-{[6-({2-hydroxy-2-[4-hydroxy-3-(hydroxymethyl)phenyl]ethyl}amino)hexyl]oxy}ethyl)phenyl] imidazolidine-2,4-dione (0.04 g, 10%) as oil.

$^1$H NMR (300 MHz, dimethylsulfoxide-D6): 1.15-1.30 (m, 4H); 1.35-1.45 (m, 4H); 2.60-2.80 (m, 4H); 3.46-3.50 (m, 2H); 3.95 (t, J=13.9 Hz, 2H); 4.07 (s, 2H); 4.47 (s, 2H); 4.60-4.70 (m, 1H); 6.72 (d, J=7.9 Hz, 1H); 7.01 (d, J=8.2 Hz, 1H); 7.29 (s, 1H); 7.51-7.61 (m, 4H); 8.34 (bs, 1H).

Intermediate 65. 2-bromo-1-(3-methoxyphenyl)ethanone

To a solution of 1-(3-methoxyphenyl)ethanone (5.5 mL, 40 mmol) in chloroform (100 mL) was added dropwise a solution of bromine (2.05 mL, 40 mmol) in chloroform (20 mL). The mixture was stirred at room temperature overnight. The solvent was removed under reduced pressure. The residue was diluted in methylene chloride (50 mL) and washed with water (2×25 mL). The organic layer was dried (Na$_2$SO$_4$) and the solvent removed under reduced pressure. Purification by column chromatography using methylene chloride as eluent gave the title compound (8.44 g, 84%) as oil.

$^1$H NMR (300 MHz, CDCl$_3$): 3.9 (s, 3H); 4.5 (s, 2H); 7.14-7.18 (dd, J=7.8, 3.2 Hz, 1H); 7.43 (t, J=8.0 Hz, 1H); 7.51-7.58 (m, 2H).

Intermediate 66. Ethyl(3-methoxyphenyl)(oxo)acetate

A suspension of selenium dioxide (4.08 g, 37 mmol) in ethanol (35 mL) was refluxed for 10 minutes and then, Intermediate 65 (8.44 g, 37 mmol) was added. The mixture was refluxed overnight. The cooled reaction was filtered through Celite and the solvent removed under reduced pressure. The residue was diluted with methylene chloride (50 mL), washed with water (2×25 mL), dried (Na$_2$SO$_4$), and concentrated. Purification by column chromatography with silica gel using methylene chloride as eluent gave the title compound (4.12 g, 53%) as oil.

$^1$H NMR (300 MHz, CDCl$_3$): 1.43 (t, J=7.1 Hz, 3H); 3.87 (s, 3H); 4.46 (q, J=7.3 Hz, 2H); 7.21 (dd, J=8.2, 2.7 Hz, 1H); 7.42 (t, J=8.0 Hz, 1H); 7.54-7.59 (m, 2H).

Intermediate 67. Ethyl difluoro(3-methoxyphenyl)acetate

Obtained from Intermediate 66 (4.12 g, 20 mmol) by the procedure described in Intermediate 1. Ethyl difluoro(3-methoxyphenyl)acetate was obtained (4.35 g, 94%) as oil.

$^1$H NMR (300 MHz, CDCl$_3$): 1.31 (t, J=7.1 Hz, 3H); 3.84 (s, 3H); 4.29 (q, J=7.1 Hz, 2H); 7.02 (dd, J=8.2, 1.6 Hz, 1H); 7.13 (s, 1H); 7.19 (d, J=7.7 Hz, 1H); 7.37 (t, J=8.0 Hz, 1H).

Intermediate 68. 2,2-difluoro-2-(3-methoxyphenyl)ethanol

Obtained from Intermediate 67 (4.35 g, 19 mmol) by the procedure described in Intermediate 2. The title compound was obtained (3.19 g, 90%) as oil.

$^1$H NMR (300 MHz, CDCl$_3$): 3.84 (s, 3H); 3.97 (t, J=13.5 Hz, 2H); 6.99-7.11 (m, 3H); 7.37 (t, J=8.0 Hz, 1H).

Intermediate 69. 1-{2-[(6-bromohexyl)oxy]-1,1-difluoroethyl}-3-methoxybenzene

To a cooled solution of Intermediate 68 (3.19 g, 16.95 mmol) in dimethylformamide (20 mL) was added 60% sodium hydride (1.36 g, 33.9 mmol) and 1,6-dibromohexane (5.2 mL, 33.9 mmol). The mixture was stirred at room temperature for 2 hours. The crude was diluted with methylene chloride (50 mL) and washed with water (3×50 mL), dried (MgSO$_4$) and concentrated. The excess of 1,6-dibromohexane was eliminated by distillation at reduced pressure (P=0.15-0.18 mmHg, T=60-65° C.) and the crude was purified by column chromatography with silica gel using methylene chloride as eluent. The title compound was obtained (3.41 g, 57%) as oil.

$^1$H NMR (300 MHz, CDCl$_3$): 1.22-1.48 (m, 4H); 1.50-1.64 (m, 2H); 1.76-1.90 (m, 2H); 3.38 (t, J=6.87 Hz, 2H); 3.52 (t,

J=6.457 Hz, 2H); 3.78-3.87 (m, 5H); 6.98 (dd, J=8.24 Hz. J=1.92 Hz, 1H); 7.05-7.10 (m, 2H); 7.34 (t, J=7.97 Hz, 1H).

Intermediate 70. 3-{6-[2,2-difluoro-2-(3-methoxyphenyl)ethoxy]hexyl}-5-(2,2-dimethyl-4H-1,3-benzodioxin-6-yl)-1,3-oxazolidin-2-one Obtained from Intermediate 69 (3.41 g, 9.7 mmol) and intermediate 51 (1.37 g, 5.49 mmol) by the procedure described in Intermediate 35. Purification by column chromatography with silica gel and hexane/ethyl acetate (1:2) as eluent gave the title compound (1.96 g, 69%) as oil.
$^1$H NMR (300 MHz, CDCl$_3$): 1.22-1.41 (m, 4H); 1.49-1.63 (m, 4H); 1.54 (s, 6H); 3.16-3.45 (m, 4H); 3.50-3.54 (m, 2H); 3.81-3.84 (m, 5H); 4.84 (s, 2H); 5.40 (t, J=8.0 Hz, 1H); 6.84 (d, J=8.5 Hz, 1H); 6.96-7.14 (m, 5H); 7.34 (t, J=7.9 Hz, 1H).

Intermediate 71. (R,S)-2-({6-[2,2-difluoro-2-(3-methoxyphenyl)ethoxy]hexyl}amino)-1-(2,2-dimethyl-4H-1,3-benzodioxin-6-yl)ethanol Obtained from Intermediate 70 (1.96 g, 3.77 mmol) by the procedure described in Intermediate 36. The title compound was obtained (1.78 g, 96%) as oil.
1H NMR (300 MHz, CDCl$_3$): 1.22-1.38 (m, 4H); 1.49-1.63 (m, 4H); 1.53 (s, 6H); 2.53-2.74 (m, 4H); 2.81-2.90 (m, 1H); 3.46-3.57 (m, 2H); 3.81-3.84 (m, 5H); 4.60-4.70 (m, 1H); 4.84 (s, 2H); 6.79 (d, J=8.5 Hz, 1H); 6.96-7.14 (m, 5H); 7.34 (t, J=7.9 Hz, 1H).

Example 13

(R,S)-4-[2-({6-[2,2-difluoro-2-(3-methoxyphenyl) ethoxy]hexyl}amino)-1-hydroxyethyl]-2-(hydroxymethyl)phenol

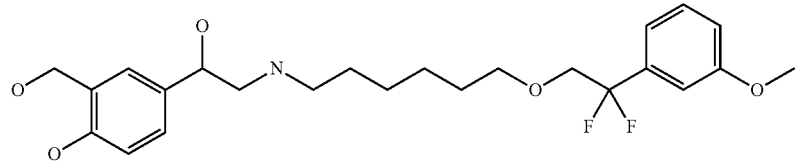

Obtained from Intermediate 71 (1.78 g, 3.61 mmol) by the procedure described in Example 1. Purification by column chromatography with silica gel and methylene chloride/methanol/triethylamine (91:8:1) as eluent gave (R,S)-4-[2-({6-[2,2-difluoro-2-(3-methoxyphenyl)ethoxy] hexyl}amino)-1-hydroxyethyl]-2-(hydroxymethyl)phenol (1.52 g, 93%) as oil.
1H NMR (300 MHz, CDCl$_3$): 1.18-1.34 (m, 4H); 1.43-1.50 (m, 2H); 1.56-1.69 (m, 2H); 2.85 (d, J=20.1 Hz, 4H); 3.48 (t, J=6.3 Hz, 2H); 3.72-3.87 (m, 5H); 4.49 (s, 2H); 4.80 (bs, 1H); 6.70 (d, J=8.2 Hz, 1H); 6.87-7.32 (m, 5H); 7.34 (t, J=7.8 Hz, 1H); 8.04 (bs, 1H).

Intermediate 72. 8-(benzyloxy)-5-((1R)-1-{[tert-butyl(dimethyl)silyl]oxy}-2-{[6-(2,2-difluoro-2-phenylethoxy)hexyl]amino}ethyl)quinolin-2(1H)-one To a solution of (8-(benzyloxy)-5-((1R)-2-bromo-1-{[tert-butyl(dimethyl)silyl]oxy}ethyl)quinolin-2(1H)-one (4.80 g, 9.83 mmol) and Intermediate 9 (3.04 g, 11.8 mmol) in dimethylsulfoxide (13.5 mL) was added sodium bicarbonate (2.49 g, 29.4 mmol) and sodium iodide (2.22 g, 14.8 mmol). The mixture was heated at 140° C. for 2 hours. After cooling, the reaction was diluted with water (40 mL) and extracted with diethyl ether (2×20 mL). The combined organic extracts were washed with water (2×10 mL) and brine (20 mL), dried (Na$_2$SO$_4$), and the solvent removed under reduced pressure. The title compound was obtained (6.40 g, 98%) as oil.
1H NMR (300 MHz, CDCl$_3$): 0.20-0.31 (m, 5H): 1.03-1.11 (m, 10H); 1.38-1.49 (m, 5H); 1.63-1.80 (m, 5H); 2.75-2.95 (m, 2H); 3.08-3.15 (m, H); 3.66-3.73 (m, 2H); 3.98-4.07 (m, 2H); 5.35 (s, 2H); 6.85 (d, J=9.9 Hz, 1H); 7.19 (d, J=8.5 Hz, 1H), 7.31-7.34 (m, 1H); 7.45 (s, 2H); 7.58-7.65 (m, 6H); 7.69-7.71 (m, 2H); 8.50 (d, J=9.9 Hz, 1H).

Intermediate 73. 8-(benzyloxy)-5-((1R)-2-{[6-(2,2-difluoro-2-phenylethoxy)hexyl]amino}-1-hydroxyethyl)quinolin-2(1H)-one To a solution of intermediate 72 (6.4 g, 9.63 mmol) in tetrahydrofuran (60 mL) was added tetra-n-butyl ammonium fluoride (5.02 g, 19.26 mmol). The mixture was stirred at room temperature overnight. The solvent was removed under reduced pressure. Purification by column chromatography using methylene chloride/methanol (from 95:5 to 85:15) as eluent gave 8-(benzyloxy)-5-((1R)-2-{[6-(2,2-difluoro-2-phenylethoxy)hexyl]amino}-1-hydroxyethy)quinolin-2 (1H)-one (1.1 g, 20%) as oil.
MS (M+): 550

Example 14

5-((1R)-2-{[6-(2,2-difluoro-2-phenylethoxy)hexyl] amino}-1-hydroxyethyl)-8-hydroxyquinolin-2(1H)-one

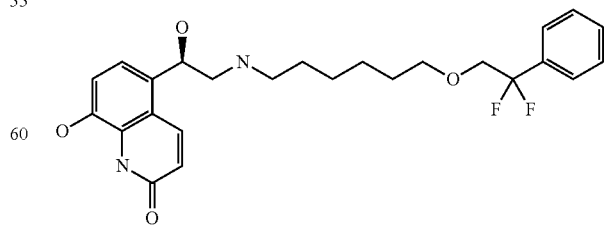

Obtained from intermediate 73 (1.10 g, 2.0 mmol) by the procedure described in Example 5. The resulting oil was purified by column chromatography with silica gel eluting with methylene chloride/methanol (95:5) to give the title compound (0.50 g, 54%) as oil.

$^1$H-NMR (300 MHz, dimethylsulfoxide-D6); 1.15-1.35 (m, 5H); 1.40-1.50 (m, 3H); 1.55-1.65 (m, 2H); 2.80-3.02 (m, 6H): 3.88-3.98 (m, 2H); 5.35-5.45 (m, 1H): 6.55 (d, J=9.4 Hz, 1H); 7.00 (d, J=7.7 Hz, 1H); 7.15 (d, J=7.4 Hz, 1H): 7.45-7.62 (m, 5H); 8.26 (d, J=9.6 Hz, 1H).

Intermediate 74. (1R)-2-{[4,4-Difluoro-6-(4-phenyl-butoxy)hexyl]amino}-1-(2,2-dimethyl-4H-1,3-benzodioxin-6-yl)ethanol Obtained from Intermediate 17 (0.39 g, 1.38 mmol) and (R)-2-amino-1-(2,2-dimethyl-4H-1,3-benzodioxin-6-yl)ethanol (0.62 g, 2.77 mmol) by the procedure described in Intermediate 18. The title compound was obtained (0.42 g, 60%) as oil and was used in the next step without further purification.

Example 15

4-((1R)-2-{[4,4-Difluoro-6-(4-phenylbutoxy)hexyl]amino}-1-hydroxy-ethyl)-2-(hydroxymethyl)phenol

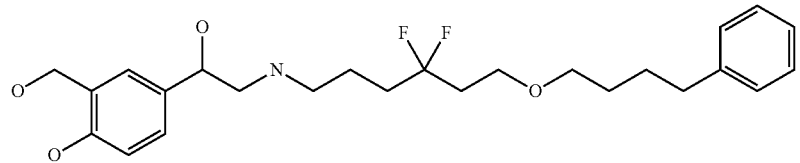

Obtained from Intermediate 74 (0.41 g, 0.83 mmol) by the procedure described in Example 1. The resulting oil was purified by semi-preparative HPLC to give the title compound (0.12 g, 31%) as oil.

$^1$H-NMR (300 MHz, Cl$_3$CD): 1.54-1.63 (m, 4H); 1.82-1.90 (m, 4H); 2.01-2.12 (m, 4H); 2.55-2.61 (m, 4H); 3.37 (t, J=6.0 Hz, 2H); 3.50 (t, J=6.0 Hz, 2H); 4.38 (bs, 2H); 4.78 (bs, 1H); 6.64 (bs, 1H); 6.83 (bs, 1H); 6.95 (bs, 1H); 7.12-7-26 (m, 5H); 8.34 (bs, 1H).

MS (M+): 451.

Intermediate 75. 3-Oxo-3-phenylpropyl acetate

To a solution of 3-chloro-1-phenylpropan-1-one (1.0 g, 5.93 mmol) in acetic acid (8 mL) was added sodium acetate (2.43 g, 29.7 mmol) and potassium iodide (100 mg). The mixture was heated in a sealed tube at 130° C. overnight. After cooling, the reaction was diluted with water (20 mL) and extracted with methylene chloride (3×20 mL). The combined organic extracts were washed with water (2×50 mL), saturated solution of sodium bicarbonate (2×50 mL) and brine (20 mL), dried (Na$_2$SO$_4$), and the solvent removed under reduced pressure. The title compound was obtained (1.0 g, 88%) as an orange solid.

$^1$H-NMR (300 MHz, Cl$_3$CD): 2.03 (s, 3H), 3.32 (t, J=6.0 Hz, 2H); 4.52 (t, J=6.0 Hz, 2H); 7.40-7.63 (m, 3H); 7.89-8.02 (m, 2H).

MS (M+): 192.

Intermediate 76. 3,3-Difluoro-3-phenylpropyl acetate

To a suspension of Intermediate 75 (1.0 g, 5.20 mmol) in bis(2-methoxyethyl)aminosulfur trifluoride (Deoxofluor®) (1.7 mL, 7.80 mmol) was added boron trifluoride dimethyl ether complex (99 µL, 0.78 mmol). The mixture was heated overnight at 85° C. and under argon. After cooling to 0° C., the reaction was diluted with methylene chloride (10 mL) and then, saturated solution of sodium bicarbonate (20 mL) was added very slowly. The mixture was extracted with methylene chloride (3×20 mL). The combined organic phase was washed with water (2×20 mL), dried (Na$_2$SO$_4$), and the solvent removed under reduced pressure. Purification by column chromatography with silica gel eluting with n-hexanetethyl acetate (from pure n-hexane to 6:4) gave the title compound (0.30 g, 30%) as orange oil.

$^1$H-NMR (300 MHz, Cl$_3$CD): 1.94 (s, 3H): 2.47-2.57 (m, 2H); 4.22 (t, J=6.0 Hz, 2H); 7.42-7.48 (m, 5H).

Intermediate 77. 3,3-Difluoro-3-phenylpropan-1-ol

To a suspension of Intermediate 76 (0.30 g, 1.40 mol) in ethanol (4 mL) was added a solution of 35% sodium hydroxide (1 mL). The mixture was stirred at room temperature for 2 hours. The crude reaction was diluted with methylene chloride (50 mL), washed with water (1×30 ML) and 1N hydrochloric acid (2×30 mL), dried (Na$_2$SO$_4$), and the solvent removed under reduced pressure. The title compound was obtained (0.22 g, 89%) as orange oil, and was used in the next step without further purification.

$^1$H-NMR (300 MHz, Cl$_3$CD): 2.36-2.52 (m, 2H); 3.85 (t, J=6.0 Hz, 2H); 7.44-7.51 (m, 5H).

Intermediate 78. 6-Bromohexyl 3,3-difluoro-3-phenylpropyl ether

Obtained from Intermediate 77 (0.41 g, 0.83 mmol) by the procedure described in Intermediate 69. The resulting oil was purified by column chromatography with silica gel eluting with n-hexane/ethyl acetate (from pure n-hexane to 9:1) to give the title compound (0.85 g of 66% purity, 64%) as oil.

$^1$H-NMR (300 MHz, Cl$_3$CD): 1.42-1.47 (m, 4H); 1.81-1.89 (m, 4H); 2.46-2.51 (m, 2H); 3.32-3.43 (m, 4H); 3.54 (t, J=6.0 Hz, 2H); 7.42-7.47 (m, 5H).

Intermediate 79. (R,S)-3-[6-(3,3-Difluoro-3-phenyl-propoxy)hexyl]-5-(2,2-dimethyl-4H-1,3-benzodioxin-6yl)-1,3-oxazolidin-2-one Obtained from Intermediate 78 (0.85 g, of 66% purity, 1.86 mmol) and Intermediate 51 (0.93 g, 3.72 mmol) by the procedure described in Intermediate 35. Purification by column chromatography with silica gel eluting with n-hexane/ethyl acetate (from pure n-hexane to 1:1) gave the title compound (0.44 g, 47%) as oil.

$^1$H-NMR (300 MHz, Cl$_3$CD): 1.32-1.61 (m, 8H); 1.54 (s, 6H); 2.46 (h, J=9.0 Hz, 2H), 3.32-3.44 (m, 4H); 3.54 (t, J=6.0 Hz, 2H); 3.73 (q, J=6.0 Hz, 2H); 4.84 (s, 2H); 5.37-5.43 (m, 1H); 6.83 (d, J=9.0 Hz, 1H); 7.00 (s, 1H); 7.12 (d, J=9.0 Hz, 1H); 7.41-7.47 (m, 5H).

MS (M+): 503.

Example 16

(R,S)-4-(2-{[6-(3,3-Difluoro-3-phenylpropoxy)hexyl]amino}-1-hydroxy ethyl)-2-(hydroxymethyl)phenol

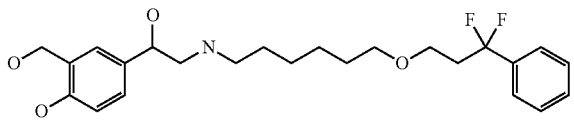

Obtained from Intermediate 79 (0.44 g, 1.0 mmol) by the procedures described in Intermediate 36 and Example 1. The resulting oil was purified by semi-preparative HPLC to give the title compound (44 mg, 10%) as oil.

$^1$H-NMR (300 MHz, Cl$_3$CD): 1.22-1.66 (m, 8H); 1.87-2.03 (m, 4H); 2.40-2.54 (m, 4H); 3.29-3.38 (m, 2H); 3.50-3.56 (m, 2H); 4.49 (bs, 2H); 4.83 (bs, 1H); 6.68-6.89 (m, 1H); 6.91-6.93 (m, 1H); 7.01 (bs, 1H); 7.38-7.49 (m, 5H).

MS (M+): 437.

Intermediate 80. Allyl 2,2-difluoro-2-phenylethyl ether

Obtained from Intermediate 6 (10.0 g, 63 mmol) and allyl bromide (6.5 mL, 76 mmol) by the procedure described in Intermediate 11. Purification by column chromatography with silica gel eluting with methylene chloride gave the title compound (11.2 g, 89%) as oil.

$^1$H-NMR (400 MHz, Cl$_3$CD): 3.76-3.90 (m, 2H); 3.98-4.12 (m, 2H); 5.14-5.32 (m, 2H); 5.70-5.90 (m, 1H); 7.35-7.59 (m, 5H).

Intermediate 81. 3-(2,2-Difluoro-2-phenylethoxy)propan-1-ol

Obtained from intermediate 80 (10.6 g, 53 mmol) by the procedure described in Intermediate 12. Purification by column chromatography with silica gel eluting with ethyl acetate/n-hexane (from 1:4 to pure ethyl acetate) gave the title compound (10.7 g, 96%) as oil.

$^1$H-NMR (200 MHz, Cl$_3$CD): 1.80 (qt, J=5.8 Hz, 2H), 3.66-3.73 (m, 4H); 3.86 (t, J$_{F-H}$=12.9 Hz, 2H), 7.43-7.54 (m, 5H).

Intermediate 82. 3-(2,2-Difluoro-2-phenylethoxy)propanal

Obtained from Intermediate 81 (3.0 g, 14.4 mmol) by the procedure described in Intermediate 13. Purification by column chromatography with silica gel eluting with methylene chloride gave the title compound (1.86 g, 60%) as oil.

$^1$H-NMR (200 MHz, Cl$_3$CD): 2.67 (td, J1=6.0 Hz, J2=1.8 Hz, 2H); 3.89 (t, J$_{F-H}$=13.3 Hz, 2H); 3.89 (t, J=6.0 Hz, 2H); 7.40-7.53 (m, 5H); 9.72 (t, J=1.8 Hz, 1H).

Intermediate 83. 1-(2,2-Difluoro-2-phenylethoxy)hept-6-en-3-ol

Obtained from Intermediate 82 (1.86 g, 8.7 mmol) by the procedure described in Intermediate 14. Purification by column chromatography with silica gel eluting with ethyl acetate/n-hexane (1:6) gave the title compound (1.24 g, 53%) as oil.

$^1$H-NMR (200 MHz, Cl$_3$CD): 1.46-1.88 (m, 4H); 2.06-2.20 (m, 2H); 3.63-3.83 (m, 3H); 3.86 (t, J$_{F-H}$=12.9 Hz, 2H); 4.92-5.07 (m, 2H); 5.75-5.92 (m, 1H); 7.43-7.55 (m, 5H).

Intermediate 84. 1-(2,2-Difluoro-2-phenylethoxy)hept-6-en-3-one

Obtained from Intermediate 83 (4.3 g, 15.8 mmol) by the procedure described in Intermediate 13. Purification by column chromatography with silica gel eluting with ethyl acetate/n-hexane (1:5) gave the title compound (1.82 g, 43%) as oil.

$^1$H-NMR (200 MHz, Cl$_3$CD): 2.25-2.34 (m, 2H); 2.48 (dt, J1=6.6 Hz, J2=1.6 Hz, 2H); 2.64 (t, J=6.0 Hz, 2H); 3.81 (t, J=6.0 Hz, 2H); 3.87 (t, J$_{F-H}$=13.3 Hz, 2H); 4.94-5.06 (m, 2H); 5.67-5.87 (m, 1H); 7.41-7.52 (m, 5H).

Intermediate 85. 3,3-Difluorohept-6-en-1-yl 2,2-difluoro-2-phenylethyl ether To a cooled solution of Intermediate 84 (1.6 g, 10 mmol) in methylene chloride (8 mL) was added CAST (4.70 ml, 40 mmol). The mixture was stirred overnight at 40° C. and under argon. The crude reaction was diluted with methylene chloride (50 mL), washed with cool water (25 mL) and saturated solution of sodium bicarbonate (2×25 mL), dried (Na$_2$SO$_4$), and the solvent removed under reduced pressure. The residue was purified by column chromatography on silica gel using ethyl acetate/n-hexane (from 1:8 to 1:6) as eluent. The title compound was obtained (600 mg, 21%) as oil.

$^1$H-NMR (300 MHz, Cl$_3$CD): 1.80-1.94 (m, 2H); 2.08-2.24 (m, 4H); 3.71 (t, J=6.5 Hz, 2H); 3.85 (t, J$_{F-H}$=13.0 Hz, 2H); 4.97-5.06 (m, 2H); 5.70-5.81 (m, 1H) 7.44-7.50 (m, 5H).

Intermediate 86. 6-(2,2-Difluoro-2-phenylethoxy)-4,4-difluorohexanal

Obtained from Intermediate 85 (0.80 g, 2.7 mmol) by the procedure described in Intermediate 17. Purification by column chromatography with silica gel eluting with ethyl acetate/n-hexane (1:5) gave the title compound (0.48 g, 60%) as oil.

$^1$H-NMR (300 MHz, Cl$_3$CD): 2.05-2.19 (m, 4H), 2.61 (t, J=7.6 Hz, 2H); 3.71 (t, J=6.2 Hz, 2H); 3.86 (t, J$_{F-H}$=13.0 Hz, 2H); 7.44-7.52 (m, 5H); 9.72 (s, 1H).

Intermediate 87. (R)-2-{[6-(2,2-Difluoro-2-phenylethoxy)-4,4-difluorohexyl]amino}-1-(2,2-dimethyl-4H-1,3-benzodioxin-6-yl)ethanol Obtained from Intermediate 86 (0.49 g, 1.66 mmol) and (R)-2-amino-1-(2,2-dimethyl-4H-1,3-benzodioxin-6-yl)ethanol (0.74 g, 3.31 mmol) by the procedure described in Intermediate 18. The title compound was obtained (0.50 g, 83%) as oil and was used in the next step without further purification.

Example 17

(R)-4-(2-{[6-(2,2-Difluoro-2-phenylethoxy)-4,4-difluorohexyl]amino}-1-hydroxyethyl)-2-(hydroxymethyl)phenol

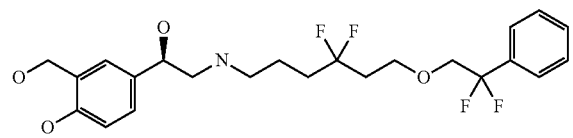

Obtained from Intermediate 87 (0.50 g, 1.0 mmol) by the procedure described in Example 1. Purification by column chromatography with silica gel, eluting with methylene chloride/methanol/ammonium hydroxide (from 200:20:1 to 150:20:1) gave (R)-4-(2-{[6-(2,2-difluoro-2-phenylethoxy)-4,4-difluorohexyl]amino}-1-hydroxyethyl)-2-(hydroxymethyl)phenol (0.12 g, 26% overall yield) as oil.

$^1$H-NMR (300 MHz, Cl$_3$CD): 1.59-1.90 (m, 4H); 2.03-2.18 (m, 2H); 2.58-2.79 (m, 4H); 3.70 (t, J=6.3 Hz, 2H); 3.84 (t, J$_{F-H}$=13.3 Hz, 2H); 4.28 (bs, 4H), 4.55-4.59 (m, 1H); 4.69 (s, 2H); 6.78 (d, J=8.0 Hz, 1H); 6.95 (s, 1H); 7.05 (d, J=8.0 Hz, 1H); 7.32-7.50 (m, 5H).

MS (M+): 459.

Intermediate 88. Ethyl 2,2-difluoro-3-hydroxy-3-phenylpropanoate

To a solution of benzaldehyde (3.0 g, 28 mmol) in anhydrous tetrahydrofuran (80 mL) was added zinc (2.4 g, 36 mmol). The mixture was heated at 75° C. under inert atmosphere and ethyl 2-bromo-2,2-difluoroacetate (4.4 mL, 34 mmol) was slowly added. The mixture was heated under the same conditions for 2 hours. After cooling, 2N hydrochloric acid (25 mL) was added until the complete consumption of unreacted zinc. The solvent was removed under reduced pressure. The crude reaction was dissolved in ethyl ether (150 mL) and washed with brine (2×100 mL), dried (Na$_2$SO$_4$), and the solvent removed under reduced pressure. The title compound was obtained (6.4 g, 99%) as yellow oil and was used in the next step without further purification.

$^1$H-NMR (300 MHz, Cl$_3$CD): 1.28 (t, J=7.1 Hz, 3H); 3.22 (bs, 1H); 4.29 (q, J=7.1 Hz, 2H); 5.15 (dd, J$_{1(F-H)}$=15.7 Hz, J$_2$=8.0 Hz, 1H); 7.37-7.44 (m, 5H).

Intermediate 89. Ethyl 2,2-difluoro-3-{[(methylthio)carbonothioyl]oxy}-3-phenyl propanoate To a solution of intermediate 88 (6.4 g, 28 mmol) in dimethylformamide (50 mL) was added 1,5-diazabicyclo(5,4,0)undec-5-ene (DBU) (17.0 mL, 0.11 mol) and carbon disulfide (16.9 mL, 0.28 mol). The mixture was stirred under inert atmosphere and at room temperature for 1 hour and 30 minutes. Then, methyl iodide was added (17.5 mL, 280 mmol) and the mixture stirred under the same conditions for 1 hour and 30 minutes. The solvent was eliminated under reduced pressure. The crude was treated with water (200 mL) and extracted with ethyl acetate (3×100 mL). The combined organic phase was washed with brine (2×100 mL), dried (Na$_2$SO$_4$), and the solvent removed under reduced pressure. Purification by column chromatography with silica gel eluting with ethyl acetate/n-hexane (from pure n-hexane to 1:9) gave the title compound (6.8 g, 76%) as oil.

$^1$H-NMR (300 MHz, Cl$_3$CD): 1.30 (t, J=7.1 Hz, 3H); 2.57 (s, 3H); 4.33 (q, J=7.1 Hz, 2H); 6.97 (dd, J$_{1(F-H)}$=16.5 Hz, J$_2$=8.0 Hz, 1H); 7.38-7.44 (m, 5H).

Intermediate 90. Ethyl 2,2-difluoro-3-phenylpropanoate

To a solution of intermediate 89 (8.0 g, 25 mmol) in dioxane (100 mL) were added diphenylphospine oxide (5.0 g, 25 mmol) and tert-butyl peroxide (2.0 mL, 11 mmol). The mixture was heated at 110° C. under inert atmosphere for 48 hours. After cooling, the solvent was removed under reduced pressure. Purification by column chromatography with silica gel eluting with ethyl acetate/n-hexane (1:8) gave the title compound (2.2 g, 42%) as oil.

$^1$H-NMR (300 MHz, Cl$_3$CD): 1.26 (t, J=7.1 Hz, 3H): 3.38 (t, J$_{F-H}$=16.3 Hz, 2H); 4.24 (q, J=7.1 Hz, 2H); 7.24-7.33 (m, 5H).

Intermediate 91. 2,2-Difluoro-3-phenylpropan-1-ol

To a cooled solution of Intermediate 90 (2.2 g, 10.3 mmol) in methanol (30 mL) was added sodium borohydride (1.94 g, 51 mmol). The mixture was stirred at 5° C. for 20 minutes and at room temperature for 2 hours. To the crude reaction was added water (1 mL) and the solvents reduced under reduced pressure. The residue was dissolved in ethyl acetate (50 mL) and washed with brine (2×25 mL), dried (Na$_2$SO$_4$), and concentrated. Purification by column chromatography with silica gel eluting with ethyl acetate/n-hexane 1:5 gave the title compound (0.75 g, 42%) as oil $^1$H-NMR (300 MHz, Cl$_3$CD): 1.87 (bs, 1H); 3.25 (t, J$_{F-H}$=16.5 Hz, 2H); 3.67 (t, J$_{F-H}$=12.5 Hz, 2H); 7.27-7.36 (m, 5H).

Intermediate 92. 6-Bromohexyl 2,2-difluoro-3-phenylpropyl ether

Obtained from Intermediate 91 (0.75 g, 4.36 mmol) by the procedure described in Intermediate 69. Purification by column chromatography with silica gel eluting with n-hexane/ethyl acetate (from pure n-hexane to 40:1) gave the title compound (0.53 g, 36%) as oil.

$^1$H-NMR (300 MHz, Cl$_3$CD): 1.40-1.52 (m, 4H); 1.57-1.68 (m, 2H); 1.83-1.94 (m, 2H); 3.23 (t, J$_{F-H}$=16.5 Hz, 2H); 3.39-3.53 (m, 6H); 7.28-7.40 (m, 5H).

Intermediate 93. (R,S)-3-[6-(2,2-Difluoro-3-phenylpropoxy)hexyl]-5-(2,2-dimethyl-4H-1,3-benzodioxin-6-yl)-1,3-oxazolidin-2-one Obtained from Intermediate 92 (0.53 g, 1.58 mmol) and Intermediate 51 (0.38 g, 1.52 mmol) by the procedure described in Intermediate 35. Purification by column chromatography with silica gel eluting with n-hexane/ethyl acetate (from 5:1 to 1:1) gave the title compound (0.30 g, 39%) as oil.

$^1$H-NMR (300 MHz, Cl$_3$CD): 1.33-1.44 (m, 4H); 1.52-1.67 (m, 4H); 1.54 (s, 6H); 3.23 (t, J=16.8 Hz, 2H); 3.31-3.52 (m, 7H); 3.87 (t, J=8.0 Hz, 1H); 4.84 (s, 2H); 5.40 (t, J=8.0 Hz, 1H); 6.82 (d, J=8.5 Hz, 1H); 7.01 (s, 1H); 7.12 (dd, J1=8.5 Hz, J2=1.9 Hz, 1H); 7.27-7.33 (m, 5H).

MS (M+): 503.

Example 18

(R,S)-4-(2-{[6-(2,2-difluoro-3-phenylpropoxy)hexyl]amino}-1-hydroxy ethyl)-2-(hydroxymethyl)phenol, hydrochloride

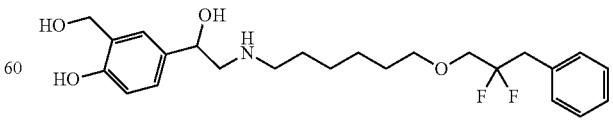

A solution of Intermediate 93 (30 mg, 0.06 mmol) in dioxane (1 mL) and concentrated hydrochloric acid (0.1 mL) was stirred at room temperature for 2 hours. The solvent was removed under reduced pressure. Purification by column chromatography with silica gel eluting with methylene chloride/methanol (from 15:1 to 10:1) gave the title compound (5 mg, 19%) as oil.

$^1$H-NMR (300 MHz, Cl$_3$CD): 1.21-1.44 (m, 4H); 1.48-1.68 (m, 4H); 2.66-2.76 (m, 4H); 3.21 (t, J$_{F-H}$=16.5 Hz, 2H); 3.41-3.50 (m, 4H); 4.58 (bs, 8H); 6.72 (d, J=7.7 Hz, 1H); 6.93-6.98 (m, 2H); 7.23-7.36 (m, 5H).

MS (M+): 437

Pharmaceutical Compositions

The pharmaceutical formulations may conveniently be presented in unit dosage form and may be prepared by any of the methods well known in the art of pharmacy. All methods include the step of bringing the active ingredient(s) into association with the carrier. In general the formulations are prepared by uniformly and intimately bringing into association the active ingredient with liquid carriers or finely divided solid carriers or both and then, if necessary, shaping the product into the desired formulation.

Formulations of the present invention suitable for oral administration may be presented as discrete units such as capsules, cachets or tablets each containing a predetermined amount of the active ingredient; as a powder or granules; as a solution or a suspension in an aqueous liquid or a non-aqueous liquid: or as an oil-in-water liquid emulsion or a water-in-oil liquid emulsion. The active ingredient may also be presented as a bolus, electuary or paste.

A syrup formulation will generally consist of a suspension or solution of the compound or salt in a liquid carrier for example, ethanol, peanut oil, olive oil, glycerine or water with flavouring or colouring agent.

Where the composition is in the form of a tablet, any pharmaceutical carrier routinely used for preparing solid formulations may be used. Examples of such carriers include magnesium stearate, talc, gelatine, acacia, stearic acid, starch, lactose and sucrose. A tablet may be made by compression or moulding, optionally with one or more accessory ingredients. Compressed tablets may be prepared by compressing in a suitable machine the active ingredient in a free-flowing form such as a powder or granules, optionally mixed with a binder, lubricant, inert diluent, lubricating, surface active or dispersing agent.

Moulded tablets may be made by moulding in a suitable machine a mixture of the powdered compound moistened with an inert liquid diluent. The tablets may optionally be coated or scored and may be formulated so as to provide slow or controlled release of the active ingredient therein.

Where the composition is in the form of a capsule, any routine encapsulation is suitable, for example using the aforementioned carriers in a hard gelatine capsule. Where the composition is in the form of a soft gelatine capsule any pharmaceutical carrier routinely used for preparing dispersions or suspensions may be considered, for example aqueous gums, celluloses, silicates or oils, and are incorporated in a soft gelatine capsule. Dry powder compositions for topical delivery to the lung by inhalation may, for example, be presented in capsules and cartridges of for example gelatine or blisters of for example laminated aluminium foil, for use in an inhaler or insufflator. Formulations generally contain a powder mix for inhalation of the compound of the invention and a suitable powder base (carrier substance) such as lactose or starch. Use of lactose is preferred.

Each capsule or cartridge may generally contain between 2 µg and 150 µg of each therapeutically active ingredient. Alternatively, the active ingredient (s) may be presented without excipients.

Packaging of the formulation may be suitable for unit dose or multi-dose delivery. In the case of multi-dose delivery, the formulation can be pre-metered or metered in use. Dry powder inhaler's are thus classified into three groups: (a) single dose, (b) multiple unit dose and (c) multi dose devices.

For inhalers of the first type, single doses have been weighed by the manufacturer into small containers, which are mostly hard gelatine capsules. A capsule has to be taken from a separate box or container and inserted into a receptacle area of the inhaler. Next, the capsule has to be opened or perforated with pins or cutting blades in order to allow part of the inspiratory air stream to pass through the capsule for powder entrainment or to discharge the powder from the capsule through these perforations by means of centrifugal force during inhalation. After inhalation, the emptied capsule has to be removed from the inhaler again. Mostly, disassembling of the inhaler is necessary for inserting and removing the capsule, which is an operation that can be difficult and burdensome for some patients.

Other drawbacks related to the use of hard gelatine capsules for inhalation powders are (a) poor protection against moisture uptake from the ambient air, (b) problems with opening or perforation after the capsules have been exposed previously to extreme relative humidity, which causes fragmentation or indenture, and (c) possible inhalation of capsule fragments. Moreover, for a number of capsule inhalers, incomplete expulsion has been reported (e. g. Nielsen at al, 1997).

Some capsule inhalers have a magazine from which individual capsules can be transferred to a receiving chamber, in which perforation and emptying takes place, as described in WO 92/03175. Other capsule inhalers have revolving magazines with capsule chambers that can be brought in line with the air conduit for dose discharge (e.g. WO91/02558 and GB 2242134). They comprise the type of multiple unit dose inhalers together with blister inhalers, which have a limited number of unit doses in supply on a disk or on a strip.

Blister inhalers provide better moisture protection of the medicament than capsule inhalers. Access to the powder is obtained by perforating the cover as well as the blister foil, or by peeling off the cover foil. When a blister strip is used instead of a disk, the number of doses can be increased, but it is inconvenient for the patient to replace an empty strip. Therefore, such devices are often disposable with the incorporated dose system, including the technique used to transport the strip and open the blister pockets.

Multi-dose inhalers do not contain pre-measured quantities of the powder formulation, They consist of a relatively large container and a dose measuring principle that has to be operated by the patient. The container bears multiple doses that are isolated individually from the bulk of powder by volumetric displacement. Various dose measuring principles exist, including rotatable membranes (e. g. EP0069715) or disks (e. g. GB 2041763; EP 0424790; DE 4239402 and EP 0674533), rotatable cylinders (e. g. EP 0166294; GB 2165159 and WO 92/09322) and rotatable frustums (e. g. WO 92/00771), all having cavities which have to be filled with powder from the container. Other multi dose devices have measuring slides (e. g. U.S. Pat. No. 5,201,308 and WO 97/00703) or measuring plungers with a local or circumferential recess to displace a certain volume of powder from the container to a delivery chamber or an air conduit e. g. EP 0505321, WO 92/04068 and WO 92/04928.

Reproducible dose measuring is one of the major concerns for multi dose inhaler devices. The powder formulation has to exhibit good and stable flow properties, because filling of the dose measuring cups or cavities is mostly under the influence of the force of gravity. For reloaded single dose and multiple unit dose inhalers, the dose measuring accuracy and reproducibility can be guaranteed by the manufacturer. Multi dose inhalers on the other hand, can contain a much higher number of doses, whereas the number of handlings to prime a dose is generally lower.

Because the inspiratory air stream in multi-dose devices is often straight across the dose measuring cavity, and because the massive and rigid dose measuring systems of multi dose inhalers can not be agitated by this inspiratory air stream, the powder mass is simply entrained from the cavity and little de-agglomeration is obtained during discharge.

Consequently, separate disintegration means are necessary. However in practice, they are not always part of the inhaler design. Because of the high number of doses in multi-dose devices, powder adhesion onto the inner walls of the air conduits and the de-agglomeration means must be minimized and/or regular cleaning of these parts must be possible, without affecting the residual doses in the device. Some multi dose inhalers have disposable drug containers that can be replaced after the prescribed number of doses has been taken (e. g. WO 97/000703). For such semi-permanent multi dose inhalers with disposable drug containers, the requirements to prevent drug accumulation are even more strict.

Apart from applications through dry powder inhalers the compositions of the invention can be administered in aerosols which operate via propellant gases or by means of so-called atomisers, via which solutions of pharmacologically-active substances can be sprayed under high pressure so that a mist of inhalable particles results. The advantage of these atomisers is that the use of propellant gases can be completely dispensed with. Such atomisers are described, for example, in PCT Patent Application No. WO 91/14468 and international Patent Application No. WO 97/12687, reference here being made to the contents thereof.

Spray compositions for topical delivery to the lung by inhalation may for example be formulated as aqueous solutions or suspensions or as aerosols delivered from pressurised packs, such as a metered dose inhaler, with the use of a suitable liquefied propellant. Aerosol compositions suitable for inhalation can be either a suspension or a solution and generally contain the active ingredient (s) and a suitable propellant such as a fluorocarbon or hydrogen-containing chlorofluorocarbon or mixtures thereof, particularly hydrofluoroalkanes, e. g. dichlorodifluoromethane, trichlorofluoromethane, dichlorotetrafluoroethane, especially 1,1,1,2-tetrafluoroethane, 1,1,1,2,3,3,3-heptafluoro-n-propane or a mixture thereof. Carbon dioxide or other suitable gas may also be used as propellant.

The aerosol composition may be excipient free or may optionally contain additional formulation excipients well known in the art such as surfactants eg oleic acid or lecithin and cosolvens eg ethanol. Pressurised formulations will generally be retained in a canister (eg an aluminium canister) closed with a valve (eg a metering valve) and fitted into an actuator provided with a mouthpiece.

Medicaments for administration by inhalation desirably have a controlled particle size. The optimum particle size for inhalation into the bronchial system is usually 1-10μ, preferably 2-5μ. Particles having a size above 20μ are generally too large when inhaled to reach the small airways. To achieve these particle sizes the particles of the active ingredient as produced may be size reduced by conventional means eg by micronisation. The desired fraction may be separated out by air classification or sieving. Preferably, the particles will be crystalline.

Achieving a high dose reproducibility with micronised powders is difficult because of their poor flowability and extreme agglomeration tendency. To improve the efficiency of dry powder compositions, the particles should be large while in the inhaler, but small when discharged into the respiratory tract. Thus, an excipient such as lactose or glucose is generally employed. The particle size of the excipient will usually be much greater than the inhaled medicament within the present invention. When the excipient is lactose it will typically be present as milled lactose, preferably crystalline alpha lactose monohydrate. Pressurized aerosol compositions will generally be filled into canisters fitted with a valve, especially a metering valve. Canisters may optionally be coated with a plastics material e. g. a fluorocarbon polymer as described in W096/32150. Canisters will be fitted into an actuator adapted for buccal delivery.

Typical compositions for nasal delivery include those mentioned above for inhalation and further include non-pressurized compositions in the form of a solution or suspension in an inert vehicle such as water optionally in combination with conventional excipients such as buffers, anti-microbials, tonicity modifying agents and viscosity modifying agents which may be administered by nasal pump.

Typical dermal and transdermal formulations comprise a conventional aqueous or non-aqueous vehicle, for example a cream, ointment, lotion or paste or are in the form of a medicated plaster, patch or membrane.

Preferably the composition is in unit dosage form, for example a tablet, capsule or metered aerosol dose, so that the patient may administer a single dose.

Each dosage unit contains suitably from 1 μg to 100 μg, and preferably from 5 μg to 50 μg of a β2-agonist according to the invention.

The amount of each active which is required to achieve a therapeutic effect will, of course, vary with the particular active, the route of administration, the subject under treatment, and the particular disorder or disease being treated.

The active ingredients may be administered from 1 to 6 times a day, sufficient to exhibit the desired activity. Preferably, the active ingredients are administered once or twice a day.

The compositions of the invention can optionally comprise one or more additional active substances which are known to be useful in the treatment of respiratory disorders, such as PDE4 inhibitors, corticosteroids or glucocorticoids and/or anticholinergics.

Examples of suitable PDE4 inhibitors that can be combined with β2-agonists are denbufylline, rolipram, cipamfyiline, arofyiline, filaminast, piciamilast, mesopram, drotaverine hydrochloride, lirimilast, roflumilast, cilomilast, 6-[2-(3,4-Diethoxyphenyl)thiazol-4-yl]pyridine-2-carboxylic acid, (R)-(+)-4-[2-(3-Cyclopentyloxy-4-methoxyphenyl)-2-phenylethyl]pyridine, N-(3,5-Dichloro-4-pyridinyl)-2-[1-(4-fluorobenzyl)-5-hydroxy-1H-indol-3-yl]-2-oxoacetamide, 9-(2-Fluorobenzyl)-N6-methyl-2-(trifluoromethyl)adenine, N-(3,5-Dichloro-4-pyridinyl)-8-methoxyquinoline-5-carboxamide, N-[9-Methyl-4-oxo-1-phenyl-3,4,6,7-tetrahydropyrrolo[3,2,1-jk][1,4]benzodiazepin-3(R)-yl]pyridine-4-carboxamide, 3-[3-(Cyclopentyloxy)-4-methoxybenzyl]-6-(ethylamino)-8-isopropyl-3H-purine hydrochloride, 4-[6,7-Diethoxy-2,3-bis(hydroxymethyl)naphthalen-1-yl]-1-(2-methoxyethyl)pyridin-2(1H)-one, 2-carbomethoxy-4-cyano-4-(3-cyclopropylmethoxy-4-difluroromethoxyphenyl)cyclohexan1-one, cis[4-cyano-4-(3-cyclopropylmethoxy-4-difluoromethoxyphenyl) cyclohexan-1-ol, ONO-6126 (Eur Respir J 2003, 22(Suppl. 45): Abst 2557) and the compounds claimed in the PCT patent applications number WO03/097613 and PCT/EP03/14722 and in the Spanish patent application number P200302613.

Examples of suitable corticosteroids and glucocorticoids that can be combined with β2-agonists are prednisolone, methylprednisolone, dexamethasone, naflocort, deflazacort, halopredone acetate, budesonide, beclomethasone dipropionate, hydrocortisone, triamcinolone acetonide, fluocinolone acetonide, fluocinonide, clocortolone pivalate, methylprednisolone aceponate, dexamethasone palmitoate, tipredane, hydrocortisone aceponate, prednicarbate, alclometasone dipropionate, halometasone, methylprednisolone suleptanate, mometasone furoate, rimexolone, prednisolone farnesylate, ciclesonide, deprodone propionate, fluticasone propionate, halobetasol propionate, loteprednol etabonate, betamethasone butyrate propionate, flunisolide, prednisone, dexamethasone sodium phosphate, triamcinolone, betamethasone 17-valerate, betamethasone, betamethasone dipropionate, hydrocortisone acetate, hydrocortisone sodium succinate, prednisolone sodium phosphate and hydrocortisone probutate.

Examples of suitable M3 antagonists (anticholinergics) that can be combined with β2-agonists are tiotropium salts, oxitropium salts, flutropium salts, ipratropium salts, glycopyrronium salts, trospium salts, revatropate, espatropate, 3-[2-Hydroxy-2,2-bis(2-thienyl)acetoxy]-1-(3-phenoxypropyl)-1-azoniabicyclo[2.2.2]octane salts, 1-(2-Phenylethyl)-3-(9H-xanthen-9-ylcarbonyloxy)-1-azoniabicyclo[2.2.2]octane salts, 2-oxo-1,2,3,4-tetrahydroquinazoline-3-carboxylic acid endo-8-methyl-8-azabicyclo[3.2.1]oct-3-yl ester salts (DAU-5884), 3-(4-Benzylpiperazin-1-yl)-1-cyclobutyl-1-hydroxy-1-phenylpropan-2-one (NPC-14695), N-[1-(6-Aminopyridin-2-ylmethyl)piperidin-4-yl]-2(R)-[3,3-difluoro-1(R)-cydopentyl]-2-hydroxy-2-phenylacetamide (J-104135), 2(R)-Cyclopentyl-2-hydroxy-N-[1-[4(S)-methylhexyl]piperidin-4-yl]-2-phenylacetamide (J-106366), 2(R)-Cyclopentyl-2-hydroxy-N-[1-(4-methyl-3-pentenyl)-4-piperidinyl]-2-phenylacetamide (J-104129), 1-[4-(2-Aminoethyl)piperidin-1-yl]-2(R)-[3,3-difluorocyclopent-1(R)-yl]-2-hydroxy-2-phenylethan-1-one (Banyu-280634), N—[N-[2-[N-[1-(Cyclohexylmethyl)piperidin-3(R)-ylmethyl]carbamoyl]ethyl]carbamoylmethyl]-3,3,3-triphenylpropionamide (Banyu CPTP), 2(R)-Cyclopentyl-2-hydroxy-2-phenylacetic acid 4-(3-azabicyclo[3.1.0]hex-3-yl)-2-butynyl ester (Ranbaxy 364057), UCB-101333, Merck's OrM3, 7-endo-(2-hydroxy-2,2-diphenylacetoxy)-9,9-dimethyl-3-oxa-9-azoniatricyclo[3.3.1.0(2.4)]nonane salts, 7-(2, 2-diphenylpropionyloxy)-7,9,9-trimethyl-3-oxa-9-azoniatricyclo[3.3.1.0*2,4*]nonane salts, 7-hydroxy-7,9,9-trimethyl-3-oxa-9-azoniatricyclo[3.3.1.0*2,4*]nonane 9-methyl-9H-fluorene-9-carboxylic acid ester salts, all of them optionally in the form of their racemates, their enantiomers, their diastereomers and mixtures thereof, and optionally in the form of their pharmacologically-compatible acid addition salts. Among the salts chlorides, bromides, iodides and methanesuiphonates are preferred.

The combinations of the invention may be used in the treatment of respiratory diseases, wherein the use of bronchodilating agents is expected to have a beneficial effect, for example asthma, acute or chronic bronchitis, emphysema, or Chronic Obstructive Pulmonary Disease (COPD).

The active compounds in the combination, i.e. the β2-agonist of the invention and the PDE4 inhibitors, corticosteroids or glucocorticoids and/or anticholinergics may be administered together in the same pharmaceutical composition or in different compositions intended for separate, simultaneous, concomitant or sequential administration by the same or a different route.

It is contemplated that all active agents would be administered at the same time, or very close in time. Alternatively, one or two actives could be taken in the morning and the other(s) later in the day. Or in another scenario, one or two actives could be taken twice daily and the other(s) once daily, either at the same time as one of the twice-a-day dosing occurred, or separately. Preferably at least two, and more preferably all, of the actives would be taken together at the same time. Preferably, at least two, and more preferably all actives would be administered as an admixture.

The active substance compositions according to the invention are preferably administered in the form of compositions for inhalation delivered with the help of inhalers, especially dry powder inhalers, however, any other form or parenteral or oral application is possible. Here, the application of inhaled compositions embodies the preferred application form, especially in the therapy of obstructive lung diseases or for the treatment of asthma.

Additional suitable carriers for formulations of the active compounds of the present invention can be found in Remington: The Science and Practice of Pharmacy, 20th Edition, Lippincott Williams & Wilkins, Philadelphia, Pa., 2000. The following non-limiting examples illustrate representative pharmaceutical compositions of the invention.

Formulation Example 1

Oral Suspension

| Ingredient | Amount |
| --- | --- |
| Active Compound | 3 mg |
| Citric acid | 0.5 g |
| Sodium chloride | 2.0 g |
| Methyl paraben | 0.1 g |
| Granulated sugar | 25 g |
| Sorbitol (70% solution) | 11 g |
| Veegum K | 1.0 g |
| Flavoring | 0.02 g |
| Dye | 0.5 mg |
| Distilled water | q.s. to 100 ml |

Formulation Example 2

Hard Gelatine Capsule for Oral Administration

| Ingredient | Amount |
| --- | --- |
| Active Compound | 1 mg |
| Lactose | 150 mg |
| Magnesium stearate | 3 mg |

Formulation Example 3

Gelatin Cartridge for Inhalation

| Ingredient | Amount |
| --- | --- |
| Active Compound (micronized) | 0.2 mg |
| Lactose | 25 mg |

Formulation Example 4

Formulation for Inhalation with a DPI

| Ingredient | Amount |
|---|---|
| Active Compound (micronized) | 15 mg |
| Lactose | 3000 mg |

Formulation Example 5

Formulation for a MDI

| Ingredient | Amount |
|---|---|
| Active Compound (micronized) | 10 g |
| 1,1,1,2,3,3,3-heptafluoro-n-propane | q.s. to 200 ml |

Biological Assays

The compounds of this invention, and their pharmaceutically-acceptable salts, exhibit biological activity and are useful for medical treatment. The ability of a compound to bind to the β adrenergic receptors, as well as its selectivity, agonist potency, and intrinsic activity can be demonstrated using Tests A to E below, or can be demonstrated using other tests that are known in the art.

Test A

Human Adrenergic β1 and β2 Receptor Birding Assays

The study of binding to human adrenergic β1 and β2 receptors was performed using commercial membranes prepared from Sf9 cells where they are overexpressed (Perkin Elmer).

The membrane suspensions (16 μg/well for β1 and 5 μg/well for β2) in assay buffer, 75 mM Tris/HCl with 12.5 mM $MgCl_2$ and 2 mM EDTA pH=7.4, were incubated with 0.14 nM $^3$H-CGP12177 (Amersham) and different concentrations of the test compounds, in a final volume of 250 μl, in GFC Multiscreen 96 well plates (Millipore) pretreated with +0.3% PEI. Non specific binding was measured in the presence of 1 μM propanolol. Incubation was for 60 minutes at room temperature and with gentle shaking. The binding reactions were terminated by filtration and washing with 2.5 volumes of Tris/HCl 50 mM pH=7.4. The affinity of each test compound to the receptor was determined by using at least six different concentrations ran in duplicate. $IC_{50}$ values were obtained by non-linear regression using SAS.

Exemplified compounds of this invention were found to have $IC_{50}$ values less than 25 nM for β2 receptor and more than 140 nM for β1 receptor Test B Human Adrenergic β3 Receptor Binding Assay Membranes prepared from Human SK-N-MC neurotumor cells from the American Type Culture Collection were used as the source of β3 receptor. The cells were grown, and the membranes prepared following the methods described in P. K. Curran and P. H. Fishman, *Cell. Signal*, 1996, 8 (5), 355-364.

The assay procedure as detailed in the mentioned publication can be summarized as follows: the SK-N-MC cell line expresses both β1 and β3 receptor and for that reason, for selective binding to β3, membranes were incubated with 1 nM $^{125}$I-CYP ((−)-3-[$^{125}$I]Iodocyanopindolol (Amersham)) and 0.3 μM CGP20712A (a β1 antagonist) in 50 mM HEPES, 4 mM $MgCl_2$ and 0.4% bovine serum albumin, pH=7.5 (assay buffer), and different concentrations of the test compounds. The final volume of the assay was 250 μl. Non specific binding was defined by 100 μM alprenolol. The samples were incubated 90 minutes at 30° C. with shaking.

The binding reactions were terminated by filtration through Whatman GF/C membranes, prewet in assay buffer at 4° C., using a BRANDEL M-24 harvester. The filters were washed three times with 4 ml each of 50 mM Tris/HCl and 4 mM $MgCl_2$ pH 7.4, and the radioactivity, retained in the filters, measured.

The affinity of each test compound to the receptor was determined by using at least eight different concentrations ran in duplicate. $IC_{50}$ values were obtained by non-linear regression using SAS. Exemplified compounds of this invention were found to have $IC_{50}$ values more than 1200 nM for β3 receptor.

Test C

Determination of Agonist Activity, Onset and Offset on Electrically-Stimulated Guinea-Pig Trachea Preparation of Isolated Trachea Strip Adult, male guinea pigs (400-500 g) were killed by a blow to the head with subsequent exsanguinations, and tracheas were excised and placed in Krebs solution in a Petri dish. The adherent connective tissue was dissected away and the lumen gently flushed with Krebs solution. Each trachea was dissected into rings containing 3-4 cartilage bands and the rings opened to form strips by cutting through the cartilage on the side opposite to the smooth muscle band. A long, cotton thread was attached to the cartilage at one end of the strip for attachment to the strain gauge, and a cotton loop to the other end for anchoring the tissue in the superfusion chamber containing 2.8 μM indomethacin. Bipolar platinum electrodes were positioned in parallel with and in close proximity to the superfused tissue. Tissues were then left for one hour to stabilize.

Electrical-Stimulation

Electrical stimulation (Coleman & Niels, 1989) was delivered as square wave pulses of 10-second trains every 2 minutes at a frequency of 5 Hz and a duration of 0.1 ms. In each experiment, the voltage was chosen following construction of a voltage-dependent response curve from 8-16 V and selecting a supramaximal dose within 10-15% of the maximum response. To establish a baseline, trachea strips were stimulated for a minimum of 20 minutes (10 peaks) at this supramaximal voltage.

Tissue Superfusion

The superfusion apparatus employed in these experiments has been described previously (Coleman & Niels, 1989). Preparations were mounted under a resting tension of 1 g. For the entire duration of the experiment trachea strips were superfused at a rate of 2 ml min$^{-1}$ with oxygenated (5% $CO_2$ in $O_2$) Krebs Henseleit solution at 37° C.

Drug Preparation

Stock drug solutions were prepared by dissolving the compounds in water. Stock solutions were then diluted in Krebs Henseleit solution to prepare different concentration ranges per each compound.

Determination of Agonist Activity

Agonist activity was determined by sequentially infusing increasing concentrations of drug prepared in the Krebs solution during 30 minutes. The magnitude of each response was measured and expressed as a percentage of inhibition over the electrically-induced contractile response. Potency values for the β-adrenoceptor agonists were expressed in absolute terms (concentration required to induce a 50% inhibition, $EC_{50}$).

Determination of Onset of Action

The time to reach a 50% onset of action ($T_{50}$ onset) is defined as the time spanning from drug agonist administration to 50% attainment the maximum response at an $EC_{50}$ drug concentration.

The time to reach maximum onset of action ($T_{max}$) is defined as the time spanning from drug agonist administration to attainment of a 100% of the maximum response at an $EC_{50}$ concentration of drug.

Determination of Offset of Action

The time to 50% offset of action is defined as the time elapsed from the end of drug administration to attainment of 50% relaxation recovery.

In the same experiment, offset of action was also expressed as the percentage of recovery reached 8 h after drug administration.

Exemplified compounds of this invention that were tested in this assay show $EC_{50}$ values less than 10 nM with more than 500 minutes as time to 50% recovery.

Test D

Histamine-Induced Bronchospasm in Conscious Guinea Pigs

Test Compounds and Products

The test compounds were dissolved in distilled water. Some of them need to be dissolved using 10% polyethylene glycol 300. Histamine HCl was supplied by Sigma (code H 7250) and dissolved in distilled water.

Experimental Procedure

Male guinea-pigs (325-450 g) were supplied by Harlan (Netherlands), and maintained at a constant temperature of 22±2° C., humidity 40-70% with 10 cycles of room air per hour. They were illuminated with artificial light in 12 hour cycles (from 7 h am to 7 h pm), A minimum of 5 days acclimatization period was left before animals were dosed with test compounds. The animals were fasted for 18 hours before the experiment with water ad libitum.

Five animals per session were placed in a methacrylate box (47×27×27 cm) which was connected to an ultrasonic nebuliser (Devilbiss Ultraneb 2000, Somerset, Pa., USA). The test compounds (β2-adrenergic agonists) were administered by aerosol during 30 seconds at concentrations between 0.1 and 1000 μg/ml. Either 5 or 180 min after test compounds administration, 250 μg/ml of histamine were nebulized during 30 s to induce a bronchospasm. The animals were observed during 5 minutes after histamine administration and the time elapsed from administration to first bronchospasm was recorded.

Determination of Activity, Duration of Action and Calculations

For each treatment and dosage the percentage of delay of bronchospasm was calculated using the following formula: % delay bronchospasm=$[(t'-t)/(t_{max}-t)]\times 100$, where $t_{max}$=maximum observation time (5 min), t=time elapsed to first bronchospasm in the animals of control group, and t'=time elapsed to first bronchospasm in compound-treated animals. The $EC_{50}$ was defined as the concentration dose causing a 50% delay of bronchospasm. An $EC_{50}$ was calculated for compounds administered 5 minutes or 180 min before histamine challenge and were named $EC_{50}$ at 5 min and $EC_{50}$ at 180 min, respectively.

Duration of action of test compounds was determined by the ratio $EC_{50}$ 5 min/$EC_{50}$ 180 min. The compounds exhibiting a ratio $EC_{50}$ 5 min/$EC_{50}$ 180 min below 100 were considered long-acting.

Exemplified compounds of this invention show long duration of action.

Test E

Acetylcholine-Induced Bronchoconstriction in Guinea Pig

Test Compounds and Products

The test compounds were dissolved in distilled water. Some of them need to be dissolved using a maximum of 10% polyethylene glycol 300. Acetylcholine HCl was supplied by Sigma (code A 6625) and dissolved in saline solution.

Experimental Procedure

Male guinea-pigs (450-600 g) were supplied by Harlan (Netherlands), and maintained at a constant temperature of 22±2° C., humidity 40-70% with 10 cycles of room air per hour. They were illuminated with artificial light in 12 hour cycles (from 7 h am to 7 h pm). A minimum of 5 days acclimatization period was left before animals were dosed with test compounds. The animals were fasted 18 hours before the experiment with water ad libitum.

Guinea pigs were exposed to an aerosol of a test compound or vehicle. These aerosols were generated from aqueous solutions using a Devilbiss nebuliser (Model Ultraneb 2000, Somerset, Pa., SA). A mixture of gases ($CO_2$=5%, $O_2$=21%, $N_2$=74%) was flown through the nebuliser at 3 L/minute. This nebuliser was connected to a methacrylate box (17×17×25 cm) where the animals were placed one per session. Every guinea pig remained in the box for a total of 10 minutes. Aerosols were generated at 0 and 5 minutes during 60 seconds each one (approximately 5 mL of solution was nebulised).

Aerosol concentrations between 0.1 and 300 μg/ml of the compounds were administered. The bronchoprotective effects of test compounds were evaluated one hour or twenty four hours post-dose with a Mumed PR 800 system.

Determination of Bronchoprotective Effect and Calculations

The guinea pigs were anesthetized with an intramuscular injection of ketamine (43.75 mg/kg), xylazine (83.5 mg/kg), and acepromazine (1.05 mg/kg) at a volume of 1 ml/kg. After the surgical site was shaved, a 2-3 cm midline incision of the neck was made. The jugular vein was isolated and cannulated with a polyethylene catheter (Portex Ld.) to allow an intravenous bolus of acetylcoline (10 and 30 μg/kg iv) at 4-min intervals. The carotid artery was cannulated and the blood pressure was measured by a Bentley Tracer transducer. The trachea was dissected and cannulated with a teflon tube and connected at a pneumotachograph Fleisch for measuring the airflow. Animal was ventilated using an Ugo Basile pump, with a volume of 10 ml/kg at a rate of 60 breaths/min. The transpulmonary pressure was measured with an esophageal cannula (Venocath-14, Venisystems) connected to Celesco transducer. Once the cannulations were completed a Mumed pulmonary measurement computer program enabled the collection of pulmonary values. The baseline values were within the range of 0.3-0.9 mL/cm $H_2O$ for compliance and within the range of 0.1-0.199 cm $H_2O$/mL per second for lung resistance ($R_L$).

The bronchocoprotective effect of inhaled compounds was determined with the concentration of the test compound causing a 50% of inhibition of bronchoconstriction ($EC_{50}$) induced by acetylcholine at 30 μg/kg iv Determination of Duration of Action Exemplified compounds of this invention show long duration of action.

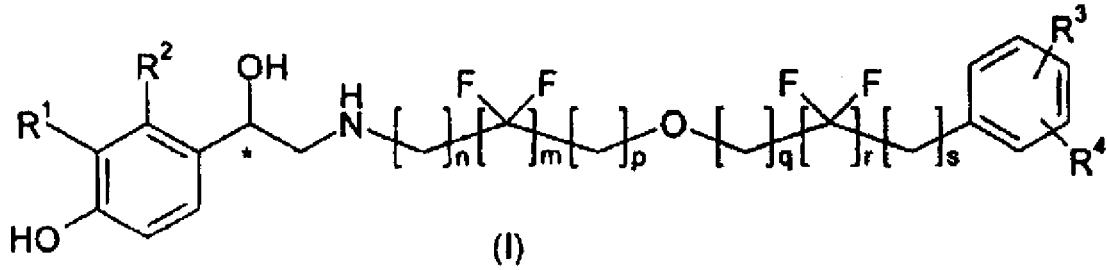

The invention claimed is:
1. A compound of formula (I):

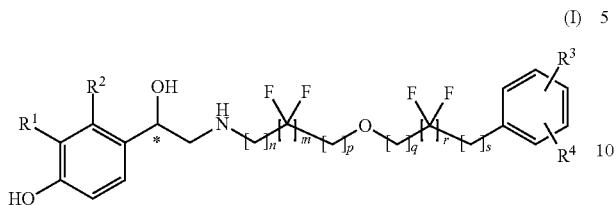

wherein:
R¹ is chosen from —CH₂OH and —NHC(O)H;
R² is a hydrogen atom;
R³ is chosen from a hydrogen atom, halogen atoms, —SO—R⁵, —SO₂—R⁵, —NH—CO—NH₂, CO—NH₂, $C_{1-4}$ alkyl, $C_{1-4}$ alkoxy and —SO₂NR⁵R⁶;
R⁴ is chosen from a hydrogen atom, halogen atoms, and $C_{1-4}$ alkyl groups;
R⁵ is chosen from $C_{1-4}$ alkyl groups and $C_{3-8}$ cycloalkyl groups;
R⁶ is independently chosen from a hydrogen atom and $C_{1-4}$ alkyl groups;
n, p and q are each independently 0, 1, 2, 3 or 4;
m and s are each independently 0, 1, 2 or 3; and
r is 0, 1 or 2
  with the provisos that:
    at least one of m and r is not 0
    the sum n+m+p+q+r+s is 7, 8, 9, 10, 11, 12 or 13
    the sum q+r+s is 2, 3, 4, 5 or 6
or a pharmaceutically-acceptable salt or stereoisomer thereof.

2. The compound according to claim 1, wherein at least one of m and r is 1.

3. The compound according to claim 2, wherein the sum m+r is 1.

4. The compound according to claim 1, wherein the sum n+m+p+q+r+s is 8, 9 or 10.

5. The compound according to claim 1, wherein the sum q+r+s is 2, 3 or 4.

6. The compound according to claim 1, wherein s is an integer chosen from 0 and 1.

7. The compound according to claim 1, wherein the sum n+p is 4, 5 or 6.

8. The compound according to claim 1, wherein the sum q+s is 1, 2, 3 or 4.

9. The compound according to claim 1, wherein R³ is chosen from a hydrogen atom, halogen atoms, and a methyl group.

10. The compound according to claim 9, wherein R³ is a chlorine or fluorine atom.

11. The compound according to claim 9, wherein R³ is a methyl group.

12. The compound according to claim 1, wherein R⁴ is a hydrogen atom.

13. The compound according to claim 1, wherein R⁴ is a chlorine atom.

14. The compound according to claim 1, wherein m and s are each 0, r and q are each 1, the sum of n and p is 6 and R⁵ and R⁶ are both hydrogen atoms.

15. A compound according to claim 1, chosen from:
(R,S)-4-(2-{[6-(2,2-Difluoro-4-phenylbutoxy)hexyl]amino}-1-hydroxy-ethyl)-2-(hydroxymethyl)phenol,
(R,S)-4-(2-{[6-(2,2-Difluoro-2-phenylethoxy)hexyl]amino}-1-hydroxy-ethyl)-2-(hydroxymethyl)phenol,
(R,S)-4-(2-{[4,4-Difluoro-6-(4-phenylbutoxy)hexyl]amino}-1-hydroxy-ethyl)-2-(hydroxymethyl)phenol,
(R,S)-4-(2-{[6-(4,4-Difluoro-4-phenylbutoxy)hexyl]amino}-1-hydroxy-ethyl)-2-(hydroxymethyl)phenol,
(R,S)-4-[2-({6-[2,2-Difluoro-2-(3-methylphenyl)ethoxy]hexyl}amino)-1-hydroxyethyl]-2-(hydroxymethyl)phenol,
4-[(1R)-2-{[6-(2,2-Difluoro-2-phenylethoxy)hexyl]amino}-1-hydroxyethyl)-2-(hydroxymethyl)phenol,
(R,S)-2-(Hydroxymethyl)-4-(1-hydroxy-2-{[4,4,5,5-tetrafluoro-6-(3-phenylpropoxy)hexyl]amino}ethyl)phenol,
(R,S)-[5-(2-{[6-(2,2-Difluoro-2-phenylethoxy)hexyl]amino}-1-hydroxy-ethyl)-2-hydroxyphenyl]formamide,
(R,S)-4-[2-({6-[2-(3-Bromophenyl)-2,2-difluoroethoxy]hexyl}amino)-1-hydroxyethyl]-2-(hydroxymethyl)phenol,
(R,S)—N-[3-(1,1-Difluoro-2-{[6-({2-hydroxy-2-[4-hydroxy-3-(hydroxymethyl)phenyl]ethyl}amino)hexyl]oxy}ethyl)phenyl]urea,
(R,S)-4-[2-({6([2,2-difluoro-2-(3-methoxyphenyl)ethoxy]hexyl}amino)-1-hydroxyethyl]-2-(hydroxymethyl)phenol,
4-((1R)-2-{[4,4-Difluoro-6-(4-phenylbutoxy)hexyl]amino}-1-hydroxy-ethyl)-2-(hydroxymethyl)phenol,
(R,S)-4-(2-{[6-(3,3-Difluoro-3-phenylpropoxy)hexyl]amino}-1-hydroxy ethyl)-2-(hydroxymethyl)phenol,
(R)-4-(2-{[6-(2,2-Difluoro-2-phenylethoxy)-4,4-difluorohexyl]amino}-1-hydroxyethyl)-2-(hydroxymethyl)phenol,
(R,S)-4-(2-{[6-(2,2-difluoro-3-phenylpropoxy)hexyl]amino}-1-hydroxy ethyl)-2-(hydroxymethyl)phenol, hydrochloride,
or a pharmaceutically-acceptable salt thereof.

16. A pharmaceutical composition comprising a therapeutically effective amount of a compound according to claim 1, and a pharmaceutically acceptable carrier.

17. The pharmaceutical composition according to claim 16, wherein the composition further comprises a therapeutically effective amount of at least one therapeutic agent.

18. The pharmaceutical composition according to claim 17, wherein the at least one therapeutic agent is chosen from corticosteroids, antichlolinergic agents, and PDE4 inhibitors.

19. The pharmaceutical composition according to claim 16, formulated for administration by inhalation.

* * * * *

UNITED STATES PATENT AND TRADEMARK OFFICE
CERTIFICATE OF CORRECTION

PATENT NO. : 8,242,177 B2  
APPLICATION NO. : 13/094156  
DATED : August 14, 2012  
INVENTOR(S) : Carlos Puig Duran et al.

Page 1 of 1

It is certified that error appears in the above-identified patent and that said Letters Patent is hereby corrected as shown below:

In the Claims:

Col. 90, line 3 delete claim 14.

Signed and Sealed this  
Sixteenth Day of July, 2013

Teresa Stanek Rea  
*Acting Director of the United States Patent and Trademark Office*

UNITED STATES PATENT AND TRADEMARK OFFICE
CERTIFICATE OF CORRECTION

PATENT NO. : 8,242,177 B2
APPLICATION NO. : 13/094156
DATED : August 14, 2012
INVENTOR(S) : Carlos Puig Duran et al.

Page 1 of 2

It is certified that error appears in the above-identified patent and that said Letters Patent is hereby corrected as shown below:

Delete the Title page and substitute therefore with the attached Title page showing the corrected number of claims in patent.

In the Claims:

Col. 90, lines 3-5 delete claim 14.

This certificate supersedes the Certificate of Correction issued July 16, 2013.

Signed and Sealed this
Thirteenth Day of August, 2013

Teresa Stanek Rea
*Acting Director of the United States Patent and Trademark Office*

(12) United States Patent
Duran et al.

(10) Patent No.: US 8,242,177 B2
(45) Date of Patent: Aug. 14, 2012

(54) DERIVATIVES OF 4-(2-AMINO-1-HYDROXYETHYL)PHENOL AS AGONISTS OF THE β2 ADRENERGIC RECEPTOR

(75) Inventors: Carlos Puig Duran, Barcelona (ES); Maria Isabel Crespo Crespo, Barcelona (ES); Julio Cesar Castro Palomino Laria, Premia de Mar (ES); Silvia Gual Roig, Cabrera de Mar (ES); Eloisa Navarro Romero, Barcelona (ES)

(73) Assignee: Almirall, S.A., Barcelona (ES)

( * ) Notice: Subject to any disclaimer, the term of this patent is extended or adjusted under 35 U.S.C. 154(b) by 0 days.

(21) Appl. No.: 13/094,156

(22) Filed: Apr. 26, 2011

(65) Prior Publication Data

US 2011/0251165 A1 Oct. 13, 2011
US 2012/0101075 A2 Apr. 26, 2012

Related U.S. Application Data

(62) Division of application No. 11/920,561, filed as application No. PCT/EP2006/004680 on May 17, 2006, now Pat. No. 7,964,615.

(30) Foreign Application Priority Data

May 20, 2005 (ES) .................... 200501229

(51) Int. Cl.
*A61K 31/135* (2006.01)
*C07C 213/00* (2006.01)
(52) U.S. Cl. ............... 514/652; 564/346
(58) Field of Classification Search .......... 564/346; 514/312, 652
See application file for complete search history.

(56) References Cited

U.S. PATENT DOCUMENTS

| | | |
|---|---|---|
| 3,007,923 A | 11/1961 | Muller et al. |
| 3,053,865 A | 9/1962 | Metuchen et al. |
| 3,104,246 A | 9/1963 | Amiard et al. |
| 3,678,137 A | 7/1972 | Pfeiffer et al. |
| 3,929,768 A | 12/1975 | Brattsand et al. |

(Continued)

FOREIGN PATENT DOCUMENTS

DE 2 236 272 2/1973

(Continued)

OTHER PUBLICATIONS

Han, J. "Advances in Characterization of Pharmaceutical Hydrates," Trends in Bio/Pharmaceutical Industry, 3:25-29 (2006).

(Continued)

*Primary Examiner* — Taylor Victor Oh
(74) *Attorney, Agent, or Firm* — Finnegan, Henderson, Farabow, Garrett & Dunner, LLP

(57) ABSTRACT

The present disclosure relates to 4-(2-amino-1-hydroxyethyl) phenol derivatives of formula (I) as well as pharmaceutical compositions comprising them, and their use in therapy as agonists of the BETA2 adrenergic receptor.

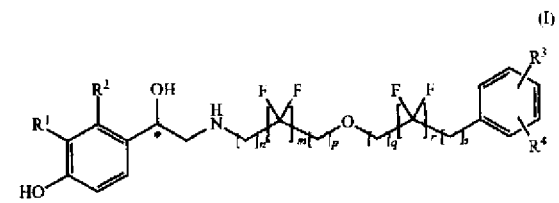

18 Claims, 1 Drawing Sheet